(12) United States Patent
Ahi

(10) Patent No.: US 11,510,586 B2
(45) Date of Patent: Nov. 29, 2022

(54) METHOD AND SYSTEM FOR ENHANCING RESOLUTION OF TERAHERTZ IMAGING AND DETECTION OF SYMPTOMS OF COVID-19, COLD, AND INFLUENZA

(71) Applicant: Kiarash Ahi, San Jose, CA (US)

(72) Inventor: Kiarash Ahi, San Jose, CA (US)

(*) Notice: Subject to any disclaimer, the term of this patent is extended or adjusted under 35 U.S.C. 154(b) by 210 days.

(21) Appl. No.: 17/075,725

(22) Filed: Oct. 21, 2020

(65) Prior Publication Data

US 2021/0038111 A1 Feb. 11, 2021

Related U.S. Application Data

(63) Continuation-in-part of application No. 17/023,356, filed on Sep. 16, 2020, which is a continuation of application No. 16/732,298, filed on Dec. 31, 2019, now Pat. No. 10,783,612, which is a continuation-in-part of application No. 15/721,876, filed on Sep. 30, 2017, now abandoned.

(60) Provisional application No. 62/402,478, filed on Sep. 30, 2016.

(51) Int. Cl.
| | |
|---|---|
| *G06K 9/00* | (2022.01) |
| *A61B 5/0507* | (2021.01) |
| *G06T 3/40* | (2006.01) |
| *A41D 13/11* | (2006.01) |

(52) U.S. Cl.
CPC .......... *A61B 5/0507* (2013.01); *G06T 3/4053* (2013.01); *A41D 13/11* (2013.01); *A61B 2576/00* (2013.01)

(58) Field of Classification Search
CPC ............................................... G01J 2005/0077
See application file for complete search history.

(56) References Cited

U.S. PATENT DOCUMENTS

| | | | |
|---|---|---|---|
| 10,783,612 B2* | 9/2020 | Ahi ....................... | G06T 3/4053 |
| 2004/0065831 A1* | 4/2004 | Federici ................ | G01S 13/887 |
| | | | 250/341.1 |
| 2007/0083114 A1* | 4/2007 | Yang ....................... | A61B 8/00 |
| | | | 600/437 |
| 2008/0116374 A1* | 5/2008 | Ouchi .................... | G01S 13/887 |
| | | | 250/306 |

(Continued)

*Primary Examiner* — Hadi Akhavannik

(57) ABSTRACT

A novel method and system for enhanced-resolution THz imaging whereby an enhanced-resolution THz image is developed by deconvolution of the original THz image that is developed using THz signals that are manipulated in time-domain and/or in frequency-domain and a point spread function (PSF) that is developed according to an equation wherein said THz signals in time-domain and/or frequency-domain are input parameters. By using this method and system, enhanced-resolution THz images are developed for detecting traces of symptoms of COVID-19 as small as a drop of water. Said novel method and system for enhanced-resolution THz imaging is used for developing a device, and method, that is: (a) rapid, (b) economical, (c) able to perform measurements remotely, (d) non-invasive. This device, and method, is capable of detecting symptoms of COVID-19 such as runny nose, congestion, and cough. The person under examination may or may not wear a face covering mask. This device, and method, is capable of performing examination remotely and without needing the person to remove the mask.

23 Claims, 46 Drawing Sheets

(56) References Cited

U.S. PATENT DOCUMENTS

| | | | |
|---|---|---|---|
| 2011/0292472 A1* | 12/2011 | Hiberty | H04N 1/04 358/479 |
| 2014/0002666 A1* | 1/2014 | Eden | G01V 8/005 250/353 |
| 2014/0198973 A1* | 7/2014 | Zhang | G01J 3/42 250/353 |
| 2015/0092063 A1* | 4/2015 | Eden | G01V 3/10 348/164 |
| 2016/0080665 A1* | 3/2016 | Barnes | G06T 7/0012 600/407 |

* cited by examiner

Fig. 1

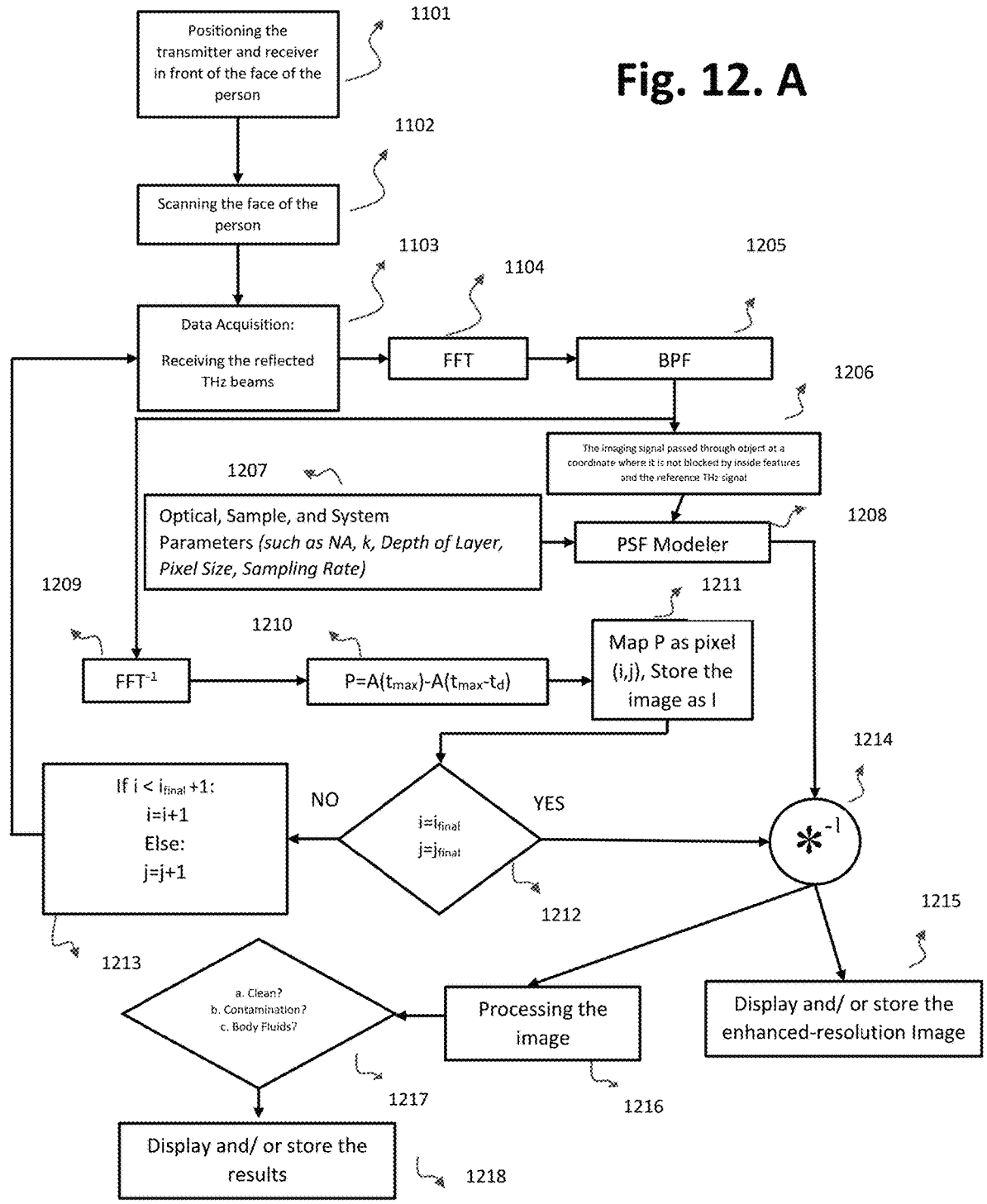
Fig. 12. A

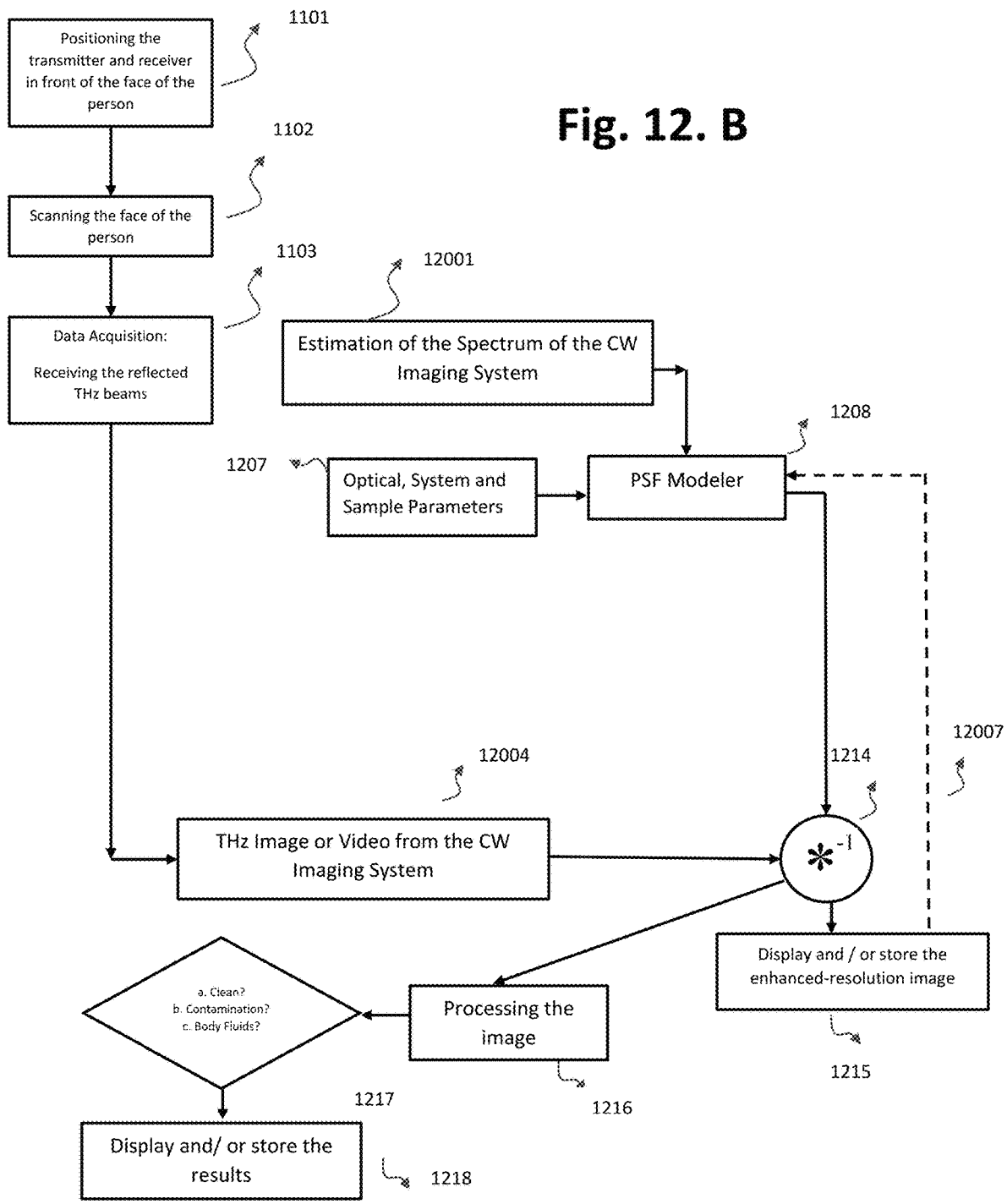
Fig. 12. B

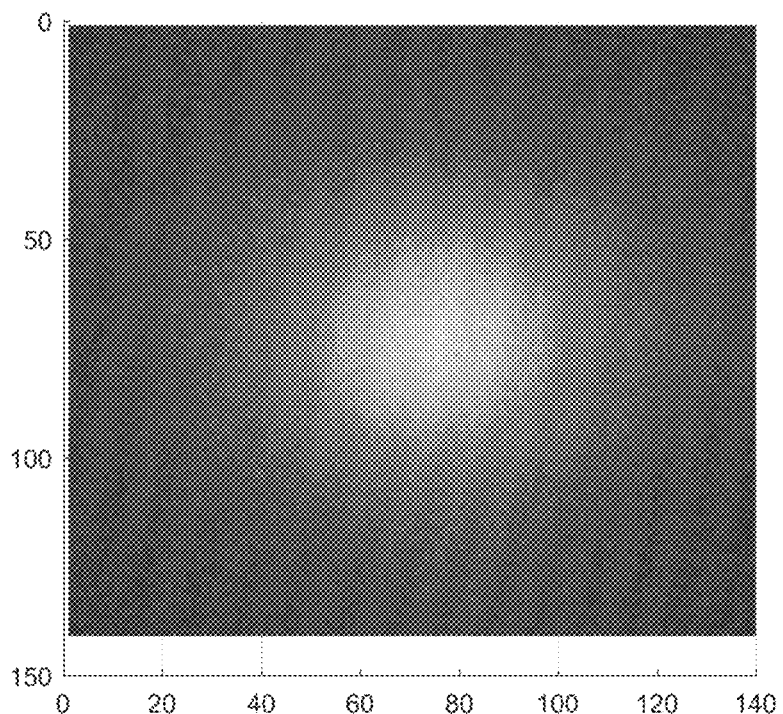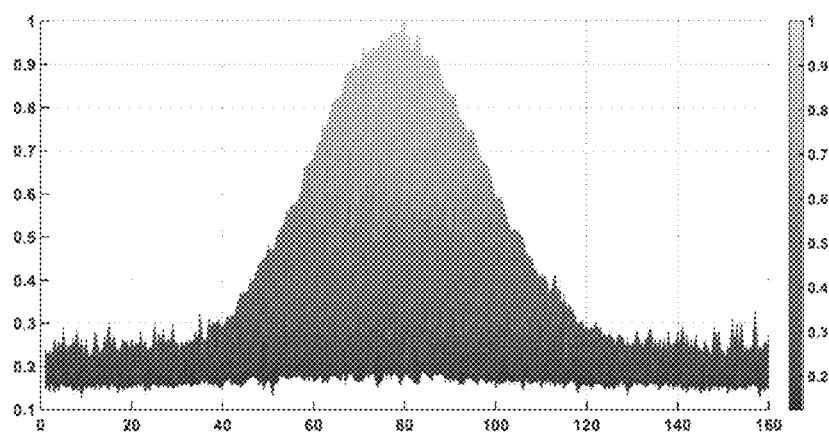
Fig. 14

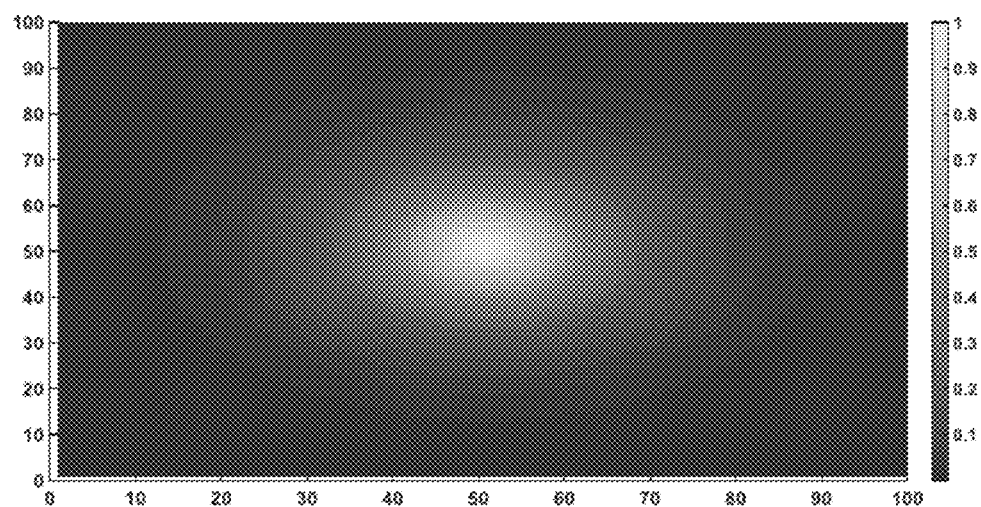
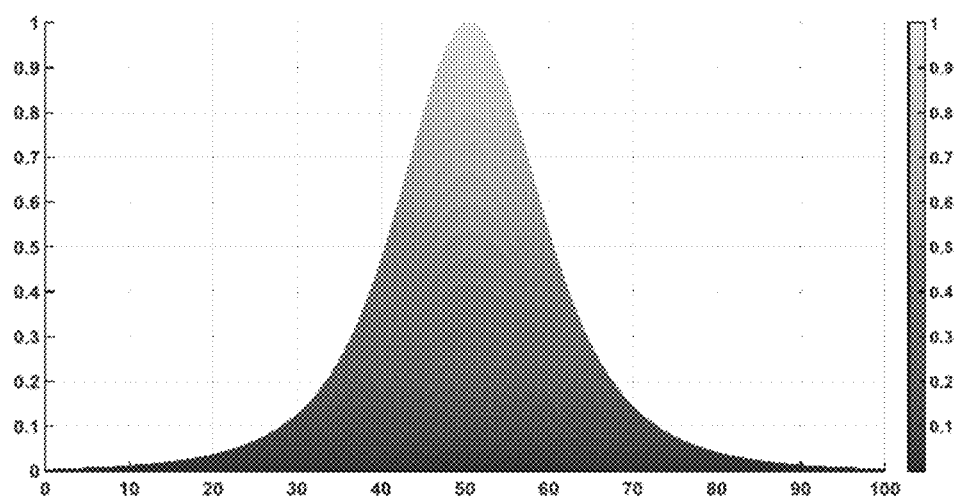
Fig. 17

METHOD AND SYSTEM FOR ENHANCING RESOLUTION OF TERAHERTZ IMAGING AND DETECTION OF SYMPTOMS OF COVID-19, COLD, AND INFLUENZA

CROSS REFERENCES TO RELATED APPLICATIONS

This application is a CIP of U.S. patent application Ser. No. 17/023,356, filed Sep. 16, 2020, which is a continuation of U.S. patent application Ser. No. 16/732,298, filed Dec. 31, 2019, now U.S. Pat. No. 10,783,612, which is CIP of U.S. patent application Ser. No. 15/721,876, filed Sep. 30, 2017, which claims benefit of priority to U.S. Provisional Patent Application Ser. No. 62/402,478, filed Sep. 30, 2016 by the present inventor.

FIELD OF INVENTION

The technology relates to the field of terahertz imaging. Field of Search: 702/28

BACKGROUND

Prior Art

The following is a tabulation of some prior art that presently appears relevant:

| | U.S. Patents | |
|---|---|---|
| Pat. No. | Issue Date | Patentee |
| 5,623,145 | April 1997 | Nuss |
| 5,710,430 | January 1998 | Nuss |
| 5,939,721 | August 1999 | Jacobsen, et al. |

Nonpatent Literature Documents

Ahi K. "A method and system for enhancing the resolution of terahertz imaging, " Meas J Int Meas Confed 2019;138:614-9. doi:10.1016/j.measurement.2018.06.044

K. Ahi, "Mathematical Modeling of THz Point Spread Function and Simulation of THz Imaging Systems," IEEE Trans. Terahertz Sci. Technol., vol. 7, no. 6, 2017.

K. Ahi, et al. "Developing terahertz imaging equation and enhancement of the resolution of terahertz images using deconvolution," in Proc. SPIE 9856, Terahertz Physics, Devices, and Systems X: Advanced Applications in Industry and Defense, 98560N, 2016, p. 98560N.

K. Ahi, et al. "Modeling of terahertz images based on x-ray images: a novel approach for verification of terahertz images and identification of objects with fine details beyond terahertz resolution," in Proc. SPIE 9856, Terahertz Physics, Devices, and Systems X: Advanced Applications in Industry and Defense, 985610, 2016, p. 985610.

K. Ahi, et al. "Quality control and authentication of packaged integrated circuits using enhanced-spatial-resolution terahertz time-domain spectroscopy and imaging," Opt. Lasers Eng., Jul. 2017.

Background Art, Technical Problem, Solution to the Problem

Currently, the global society is highly impacted by COVID-19 pandemic. Billions are dedicated to new spending for public health imaging technology [1].

To prevent spread of COVID-19, people in the society are constantly being tested for symptoms of this disease. As an example, upon entering a person to a building, body temperature of the person is measured by using infrared thermometer handheld devices. However, according to the website of CDC, fever is only one of the symptoms of COVID-19 [2]. It is possible that a person contracted COVID-19 does not show fever at the time of examination [3]. The more symptoms are measured, the higher the probability of detecting if a person has contracted COVID-19. According to the guidelines published by CDC, cough, congestion or runny nose, are among the symptoms of COVID-19. FIG. 1. Illustrates a screenshot captured from the website of CDC on Sep. 28, 2020 (https://www.cdc.gov/coronavirus/2019-ncov/symptoms-testing/symptoms.html). Toward prevention of the spread of Coronavirus and for suppressing the pandemic caused by this outbreak, many local governments, states within the Unites States, and countries around the globe have mandated wearing of face covering masks.

A mask covers the face of the mask wearer and thus, conceals some of the symptoms of COVID-19 such as runny nose or existence of body fluids on the face of the mask wearer. In addition, the inside surface of the mask, that is not visible, while the person is wearing the mask, may be contaminated by the body fluids (as a result of coughing or runny nose).

In other words, although masks are mandated for prevention of the spread of COVID-19, they conceal some of the symptoms of this disease.

In this patent application a hand-held device, and method, is disclosed that is capable of detecting trace of coughing or runny nose on the face of a person who wears a mask, without needing the person to remove the mask. This device, and method, is capable of detecting the trace of cough or runny nose on the inner surface of the mask or on the face of the person whether the part of the face is concealed by the mask or not.

The disclosed device and method may be used for remotely scanning the inside of the nose of the person to detect if the person has runny nose whether the nose of the person is concealed by a mask or not.

The size of raindrops (or equivalently, the body-fluids as a result of cough or runny-nose on the face or mask of the person) is around 0.5 mm to 4 mm, with size distribution of sharply decreasing after 2-2.5 mm [5]. Whereas, the resolution of a THz imaging system with 0.25 THz frequency (wavelength of 1.2 mm), numerical aperture (NA) of 0.35, and K-factor of 1 is 3.4 mm. Hence, for thorough detection of drops of body-fluids, the resolution of the THz imaging system needs to be enhanced. For enhancing the resolution, the disclosed device, and method, may further comprise of a resolution-enhancement technology, according to the principle of U.S. Pat. No. 10,783,612 by the present inventor where a novel method and system is disclosed for enhanced-resolution THz imaging whereby the enhanced-resolution image is developed by deconvolution of image that is developed using the signals that are manipulated in time-domain and/or in frequency-domain and a point spread function (PSF) that is developed according to an equation wherein said time-domain and/or frequency-domain signals are input parameters. By using this method and system, enhanced-resolution THz images with better quality and resolution than those of the conventional THz images are achieved. By implementing this method, finer features are observable in the resulted image and more accurate measurement is achieved. The resolution enhancement technology provides enhanced-resolution THz imaging for detecting small traces of contaminations and body fluids on the mask and face of the person.

To control the spread of COVID-19 people in the society are constantly being monitored for symptoms of COVID-19. During this pandemic large numbers of people in public spaces need to be evaluated. Hence, evaluation devices and methods with the following characteristics are needed to be developed to address the needs of public examinations of symptoms of COVID-19 during the ongoing pandemic: (a) rapid, (b) economical, (c) able to perform measurements remotely, (d) non-invasive. Infrared thermometer handheld devices are (a) rapid, (b) economical, (c) able to perform measurements remotely, (d) non-invasive. Infrared thermometer handheld devices are used to detect fever, which is a symptom of COVID-19. The disclosed device, and method, in this patent application detects additional symptoms of COVID-19, namely coughing and runny noise. The disclosed device, and method, in this patent application is: (a) rapid, (b) economical, (c) able to perform measurements remotely, (d) non-invasive. The disclosed device, and method, is able to detect the trace of coughing or runny nose whether the person under examination wears a face covering mask or not, without needing of removal of the mask. Using the disclosed THz device and method together with the handheld infrared thermometers result in detection of multiple symptoms of COVID-19, which is equivalent to a more concrete evaluation of a person. In addition, COVID-19 cases where fever does not exist at the time of examination can be diagnosed using the disclosed device and method.

Solution to the Problem of the Low Resolution of THz Imaging in Prior Art

For overcoming the diffraction and achieving super-resolution THz images, near-field THz imaging systems were proposed [4]. In near-field systems, the imaging beam is projected through an aperture with a very small diameter (implemented in nano-scale). The object is placed at a subwavelength distance from the aperture. Thus, the shortcoming of near-field THz imaging is the fact that imaging of the objects which are thicker than roughly a hundred micrometers is not possible [5]. In other words, evaluation of a mask wearing person for symptoms of COVID-19 is not possible using near-field THz imaging.

Regarding far-field THz imaging, Trofimov et al. have used correlation and edge sharpening algorithms for enhancing the quality of THz images [6], [7]. Schildknecht et al. have proposed blind-deconvolution of the THz image and a numerically estimated PSF. As a result, they could reveal traces of a slit as narrow as 1 mm in a metallic test structure by using beams of 0.5-0.75 THz [8]. Hu and Nuss have proposed the possibility of frequency-domain filtering by using DSP to process only higher THz frequencies for achieving higher resolution [9]. Burford et al. have found that applying high-pass error function filters in the frequency-domain leads to improving image clarity and minimizing distortion of the time-domain THz signal [10]. Zhang et al. have shown that THz images in frequency-domain might contain more information than THz images in the time-domain [11]. Menlo Systems GmbH offers complementary computer programs called "MenloSystems ImageViewer BETA" and "MenloSystems Image Loader BETA" for enhancing the quality of their THz imaging systems, wherein the time-domain THz signal is converted to frequency-domain and can be manipulated by using a variety of frequency-domain filters [12]. Thorlabs Inc offers physical THz Bandpass Filters which can be used for filtering out the low and high-frequency spectrum of the THz imaging beam [13]. BATOP GmbH is developing lenses with low absorptions and high Numerical Apertures for enhancing the resolution [14]. Chernomyrdin et al. have proposed a wide-aperture aspherical THz lens for high-resolution imaging. As a result, they could image two point objects spaced at a $0.95\lambda$, distance providing a contrast of 15% [15]. The latter group has also proposed a solid-immersion imaging technique for enhancing the resolution from 0.85 down to 0.35 factor of the wavelength [16]. Kulya et al. have proposed taking material dispersion into account for enhancing the quality of THz images [17].

SUMMARY

To control the spread of COVID-19 people in the society are constantly being monitored for symptoms of COVID-19. During this pandemic large number of people in public spaces need to be evaluated. Hence, evaluation devices and methods with the following characteristics are needed to be developed to address the needs of public examinations of symptoms of COVID-19 during the ongoing pandemic: (a) rapid, (b) economical, (c) able to perform measurements remotely, (d) non-invasive. Infrared thermometer handheld devices are: (a) rapid, (b) economical, (c) able to perform measurements remotely, (d) non-invasive. Infrared thermometer handheld devices are used to detect fever, which is a symptom of COVID-19. The disclosed device, and method, in this patent application detects additional symptoms of COVID-19, namely coughing and runny nose. The disclosed device, and method, in this patent application is: (a) rapid, (b) economical, (c) able to perform measurements remotely, (d) non-invasive. The disclosed device, and method, is able to detect the trace of coughing or runny nose whether the person under examination wears a face covering mask or not, without needing of removal of the mask. Using the disclosed THz device together with the handheld infrared thermometers result in detection of multiple symptoms of COVID-19, which is equivalent to a more concrete evaluation of a person. In addition, the COVID-19 cases where fever does not exist at the time of examination can be diagnosed using the disclosed device and method.

The disclosed device emits electromagnetic waves in the frequency range of THz. Electromagnetic waves in the frequency range of THz have these characteristics: (a) they penetrate most of the non-metallic materials (including ingredient materials of the face covering masks), (b) they show unique characteristics upon interaction with molecules of water [18], (c) they partially get reflected upon change of the refractive index in the path of travelling (part of the THz beam gets reflected as the THz beam penetrates the face mask). The mentioned characteristics of THz beams enable them to penetrate the face mask of the mask wearing person and detect if there is any trace of body fluids (which is an indication of runny nose or coughing) on the face of the mask wearer, or on the mask, without needing the person to remove the mask. Further, this device can be used to scan inside of the nose of the person to detect if the person has runny nose. In other words, this method and device detects existence of fluid or mucus inside the nose of the person.

Scanning of the throat and the mouth of the person by asking the person to open their mouth and positioning the emitter of the THz beam in front of the mouth of the person and moving the emitter and received in a 1D or 2D manner. For scanning the inside of the nose of the person, for detecting fluids, congestion, or mucus the emitter and the received shall be positioned in front of the openings of the nose, or nostril. Sine THz beams pass through the mask, the person may or may not wear a face covering mask during the examination of the mouth, throat, and nose. Wearing the mask helps the operator (healthcare workers) to stay safe since the mask shall cover the mouth and the mouth of the person who is under examination.

The size of raindrops (or equivalently, the body-fluids as a result of cough or runny-nose on the face or mask of the person) is around 0.5 mm to 4 mm, with size distribution of sharply decreasing after 2-2.5 mm [5]. Whereas, the resolution of a THz imaging system with 0.25 THz frequency (wavelength of 1.2 mm), numerical aperture (NA) of 0.35, and K-factor of 1 is 3.4 mm. Hence, for thorough detection of drops of body-fluids, the resolution of the THz imaging systems needs to be enhanced. For enhancing the resolution, the disclosed device, and method, may further comprise of a resolution-enhancement technology, according to the principle of U.S. Pat. No. 10,783,612 by the present inventor where a method and system for developing enhanced-resolution THz images is disclosed. By using this method and system, enhanced-resolution THz images with better quality and resolution than those of the conventional THz images are achieved. By implementing this method, finer features are observable in the resulted image and more accurate measurement is achieved. The resolution enhancement technology provides enhanced-resolution THz imaging for detecting small traces of contaminations or body fluids on the mask and face of the person.

Advantages

A hand-held device, and method, that is: (a) rapid, (b) economical, (c) able to perform measurements remotely, (d) non-invasive. This device, and method, is capable of detecting symptoms of COVID-19 such as runny nose, congestion, and cough. The person under examination may or may not wear a face covering mask. This device, and method, is capable of performing examination remotely and without needing the person to remove the mask. Using the disclosed device together with the handheld infrared thermometers result in detection of multiple symptoms of COVID-19 which is equivalent to a more concrete evaluation of a person. In addition, COVID-19 cases where fever does not exist, at the time of examination, can be diagnosed using the disclosed device and method. Since the resolution of THz imaging systems need to be enhanced in order to detect traces of body-fluids as small as a waterdrop on the mask or the face of the person, the disclosed device and method may further comprise of a resolution enhancement technology, according to the principle of U.S. Pat. No. 10,783,612 by the present inventor. The resolution enhancement technology provides enhanced-resolution THz imaging for detecting traces of contaminations on the mask and face of the person as small as a drop of water. Sine THz beams pass through the mask, the person may or may not wear a face covering mask during the examination of the mouth, throat, and nose. Wearing the mask helps the operator (healthcare workers) to stay safe since the mask shall cover the mouth and the mouth of the person who is under examination.

Accordingly, several advantages of one or more aspects of the resolution-enhancement technology are as follows: to provide a system and process for developing THz images with higher resolution, diagnosis of smaller defects in packaged objects and unpackaged items including detection of traces of body fluids or contaminations on the mask or the face of a mask wearing person, achieving higher accuracy in noninvasive measurements of the features inside packaged items and in unpackaged items and as a result diagnosing if an imaged feature is a drop of body fluid from the runny nose of the person whether the person is wearing a face covering mask or not, achieving noninvasive imaging of finer features inside packaged and in unpackaged items such as detecting fluid or mucus inside the nose of the person or inside the throat of the person whether the person is wearing a face covering mask or not, improving the certainty of authentication of items and detection of counterfeit items such as counterfeit face covering masks, improving the accuracy and certainty of medical diagnosis in THz imaging. Other advantages of one or more aspects will be apparent from a consideration of the drawings and ensuring description.

DRAWINGS-FIGURES

FIG. 1. Illustrates a screen shot captured from the website of CDC on Sep. 28, 2020 (https://www.cdc.gov/coronavirus/2019-ncov/symptoms-testing/symptoms.html). According to the guidelines published by CDC, cough, congestion or runny nose, are among the symptoms of COVID-19.

Figure 7:
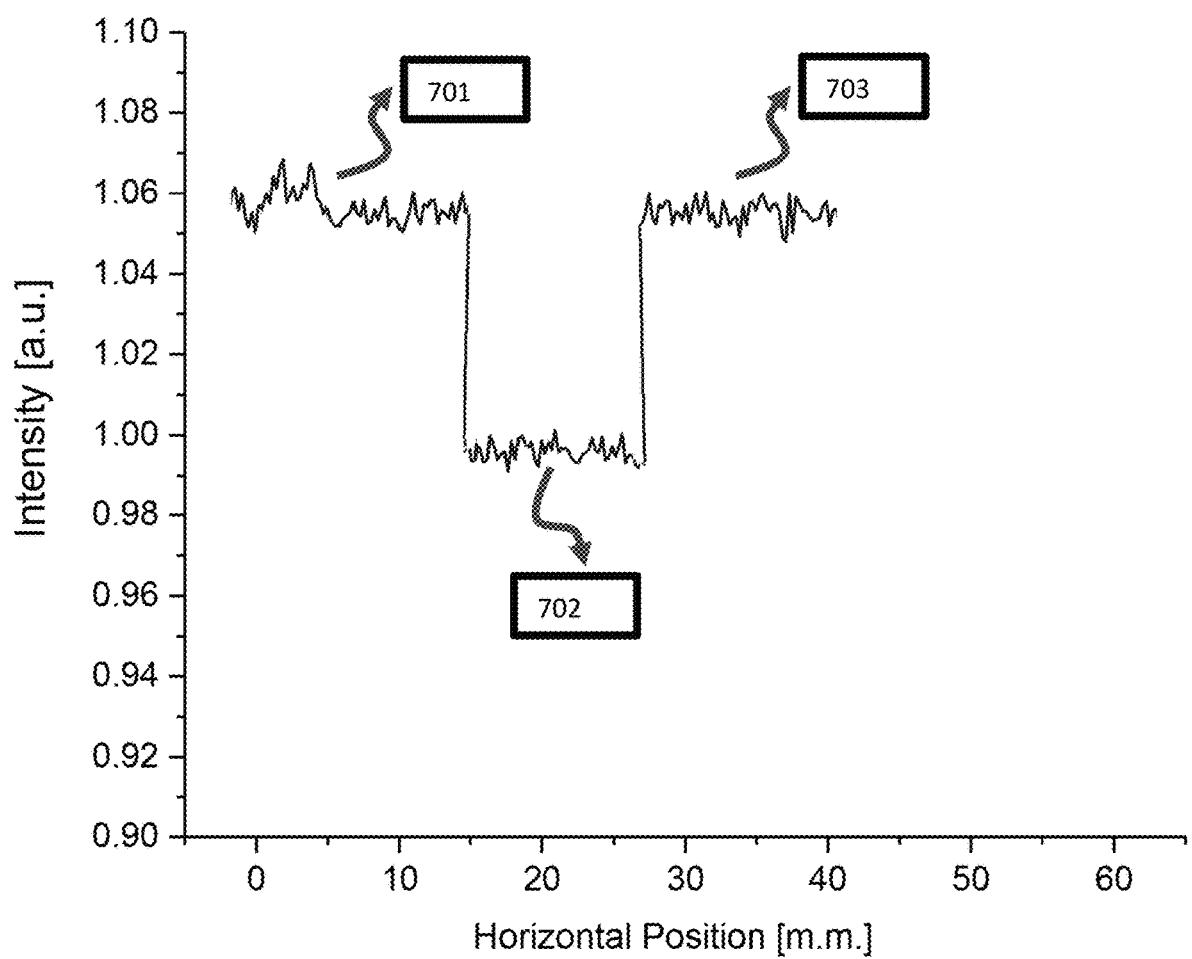

FIG. 7 illustrates the intensity of the reflected THz beam (on y-axis) against the scanned dimension (on x-axis); this graph is generated by mapping either of the first or second peaks (or combination of both) on the scanned length. For the case of continues-wave (CW) THz imaging systems, this graph is generated by mapping the intensity of the reflected THz beam on the scanned dimension. The lower intensity of the THz beam on 702 as compared with 701 and 703, is an indication of the existence of body fluids on the face and/or the mask.

Figure 8:
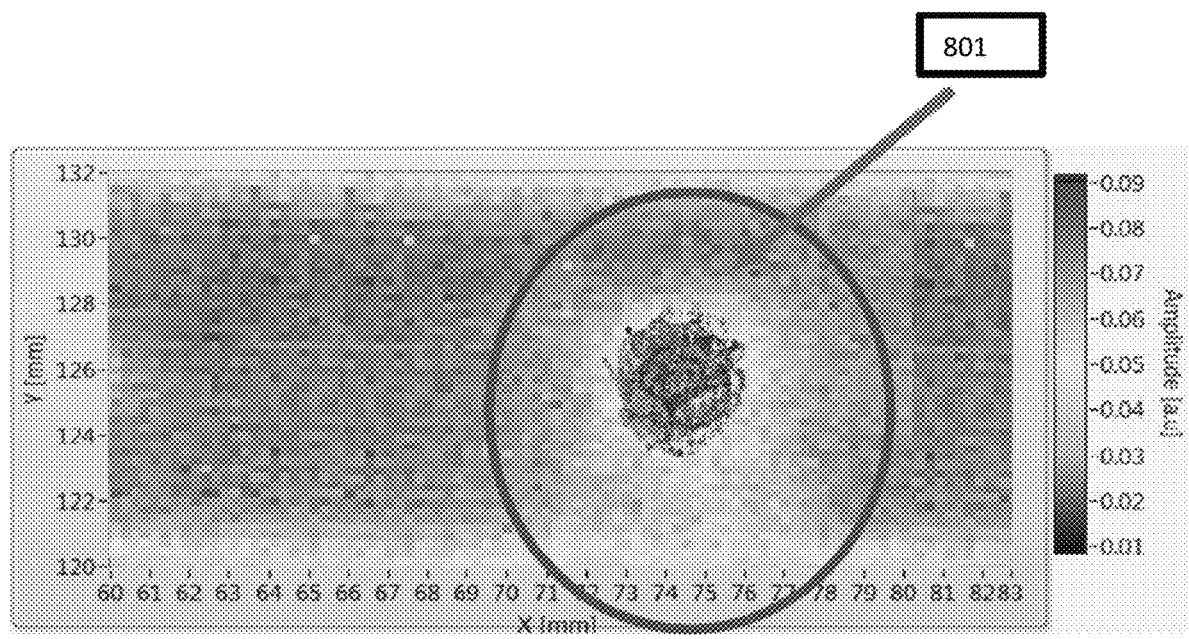
Figure 8:
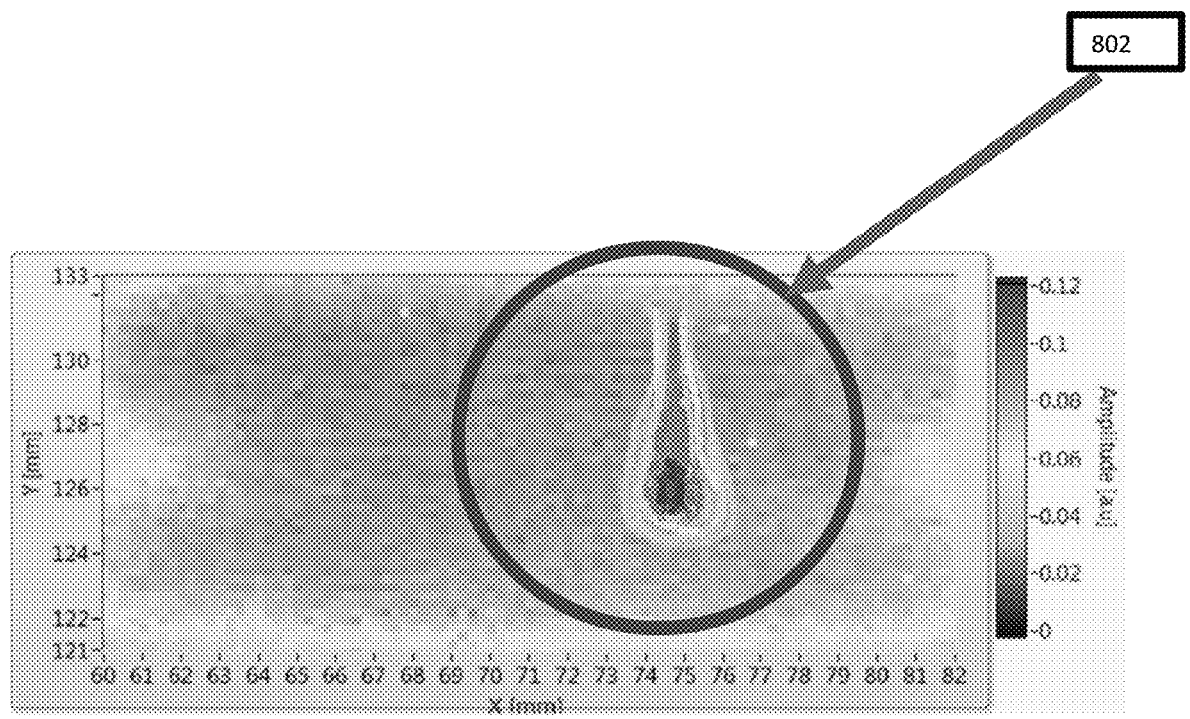
Figure 8:
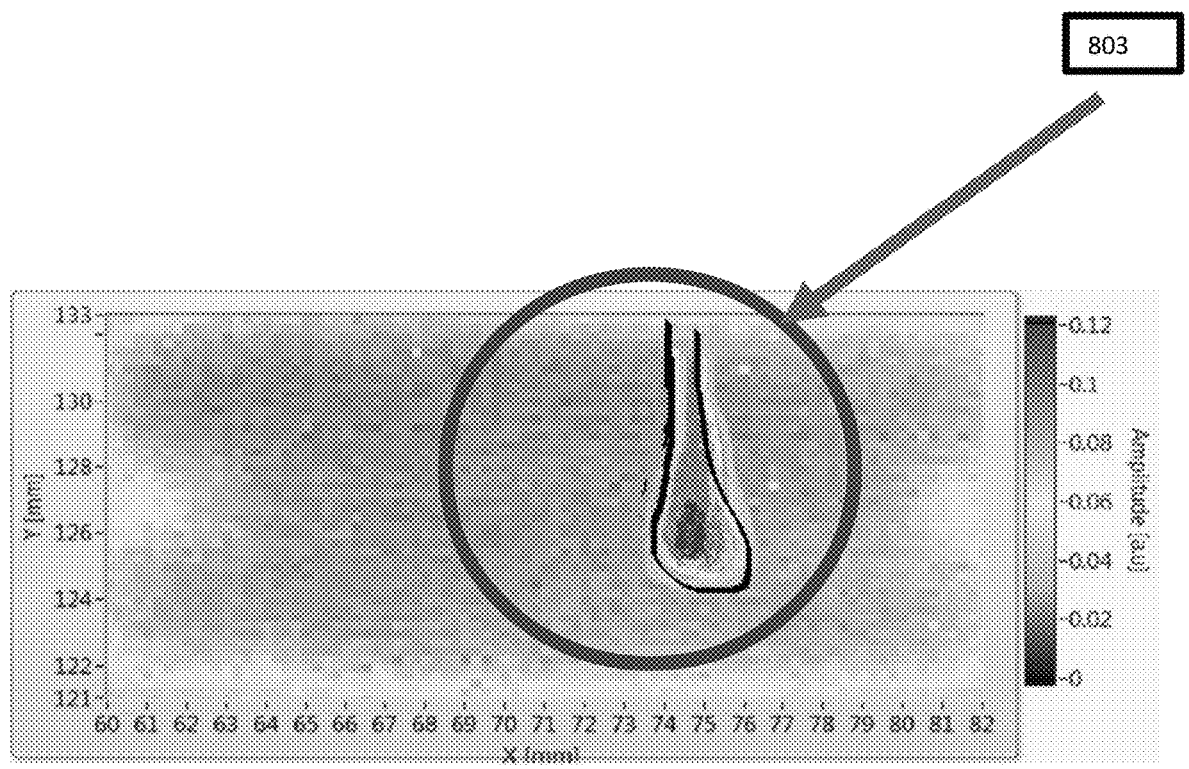

FIG. 8A illustrates the intensity of the reflected THz beam mapped on a 2-dimensional scanned area; the observed low intensity, 801, is an indication of existence of body-fluids on the face or the mask.

FIG. 8B illustrates the enhanced-resolution version of the THz image of FIG. 8A, 802 is the trace of a waterdrop leaked from the runny nose of a person identified on the enhanced-resolution THz image.

FIG. 8C illustrates the reconstructed version of the enhanced-resolution THz image of FIG. 8B, 803 is the reconstructed version of the trace of a waterdrop leaked from the runny nose of a person identified on the enhanced-resolution THz image.

Figure 9:
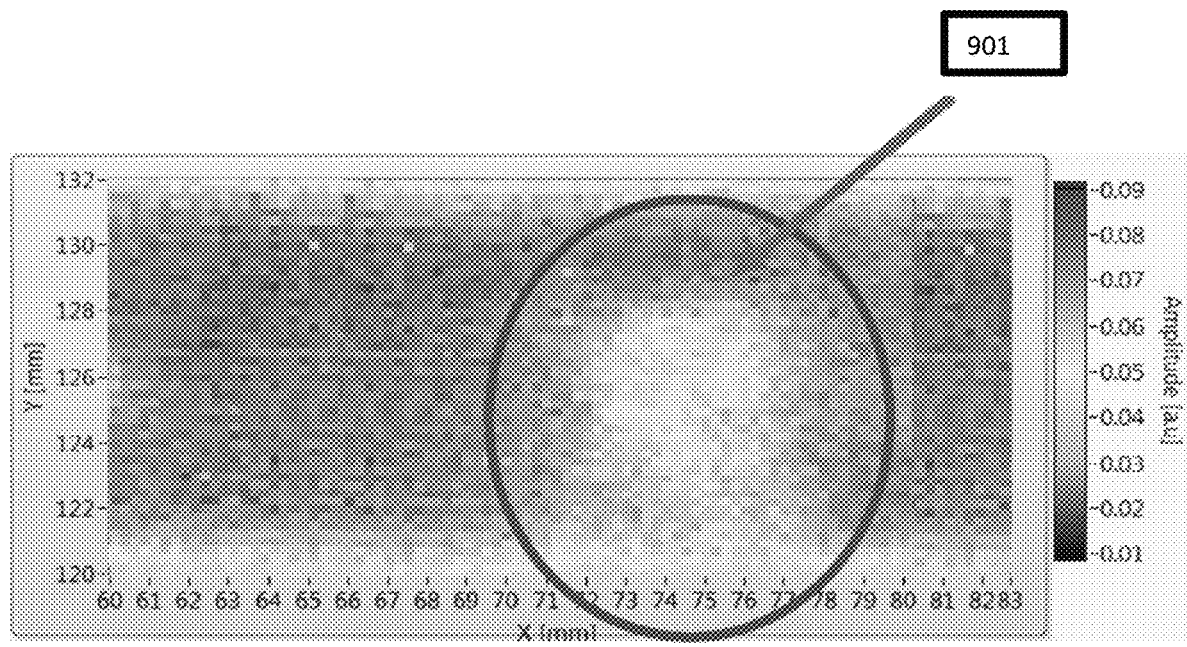

FIG. 9 illustrates the intensity of the reflected THz beam mapped on the 2-dimensional scanned area; the observed low intensity, 901, is an indication of existence of contamination on the face or the mask.

Figure 10:
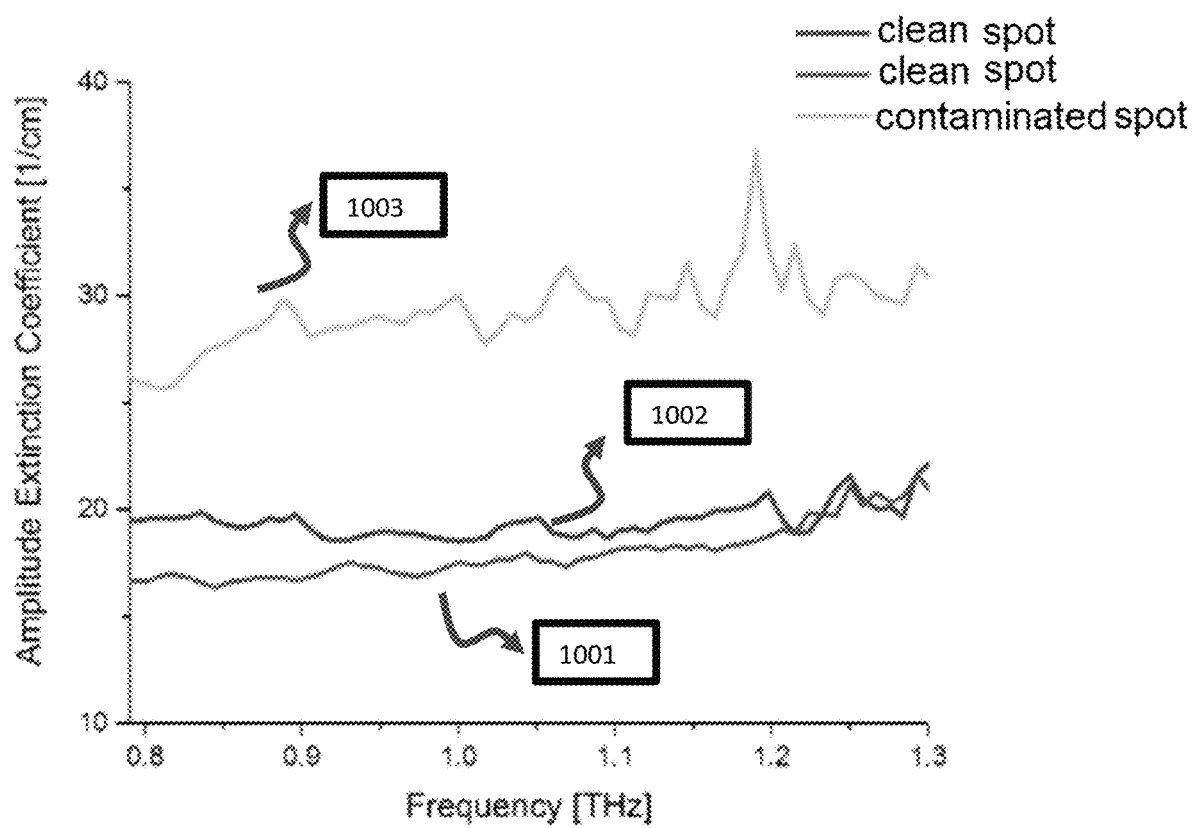

FIG. 10 illustrates the frequency-domain version of the reflected THz beam; the contaminated spot, 1003, show different frequency profile as compared with the clean spots, 1001 and 1002.

Figure 11:
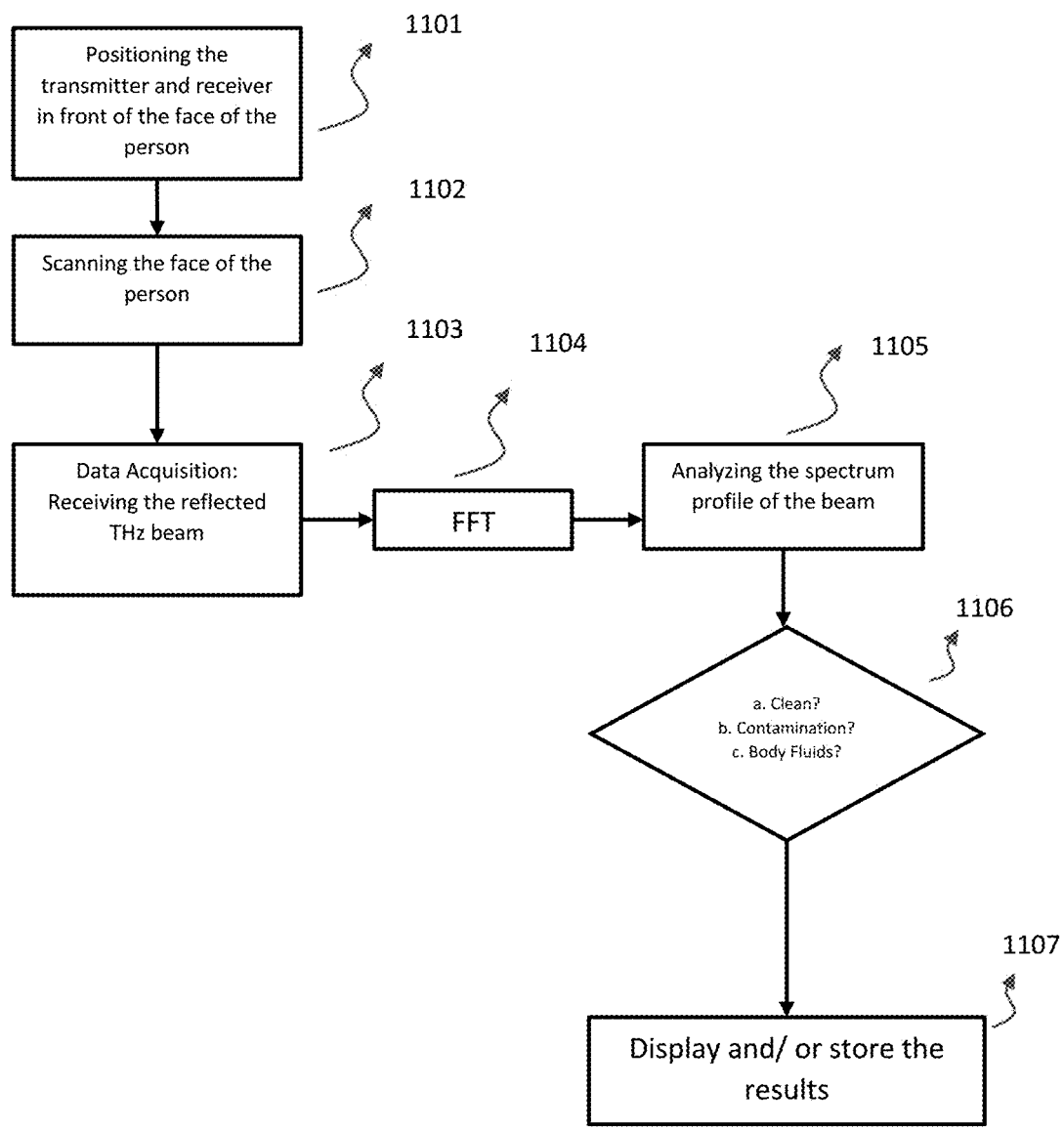

FIG. 11 illustrates the flowchart of the disclosed method and system.

FIG. 12A illustrates the flowchart of the disclosed method and system equipped with enhanced-resolution time-domain spectroscopy (TDS) THz imaging technology.

FIG. 12B illustrates flowchart of the disclosed method and system equipped with enhanced-resolution CW THz imaging technology.

Figure 13:
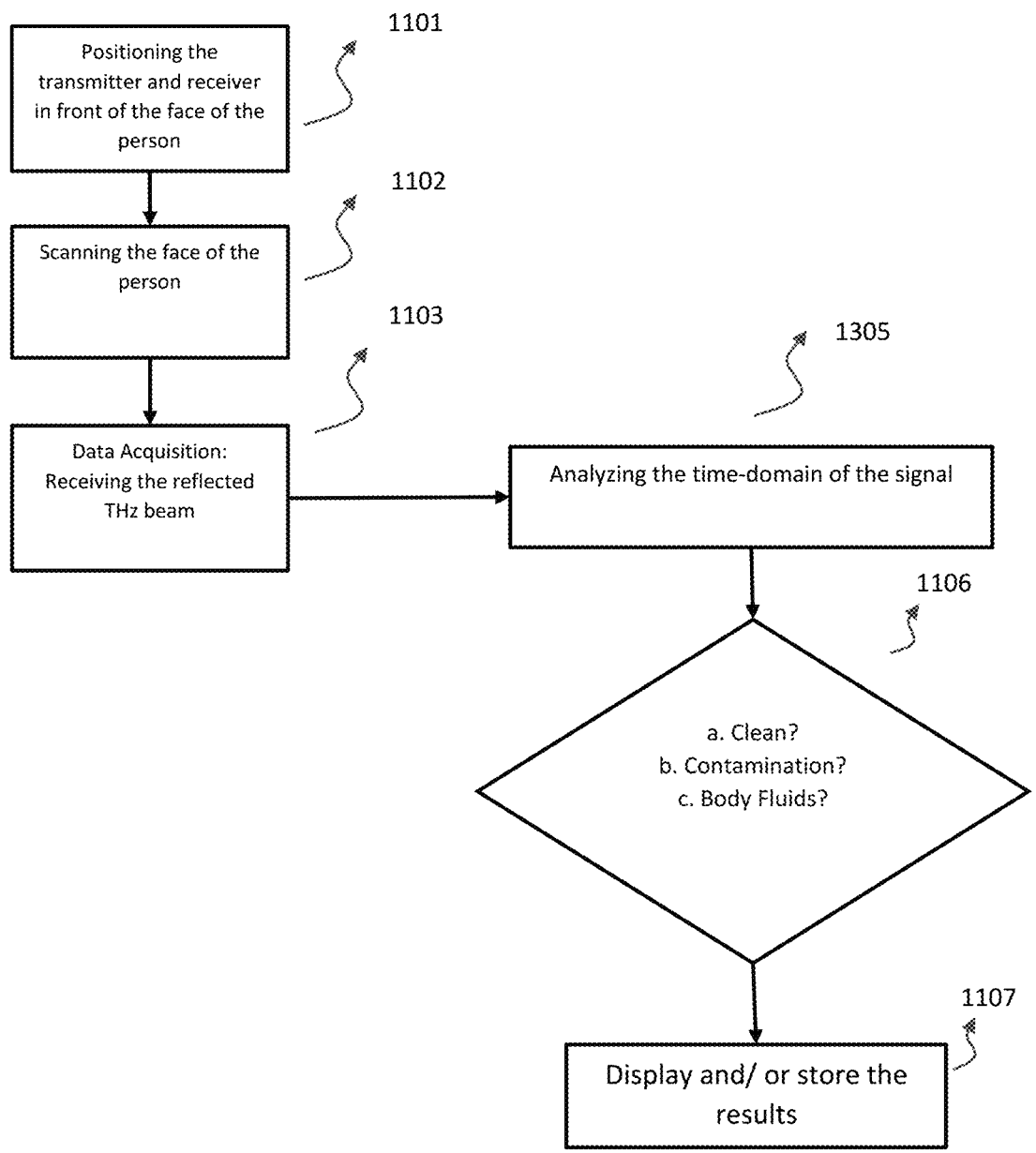

FIG. 13 illustrates flowchart of the disclosed method and system.

FIG. 14 Illustrates the measured PSF of a THz imaging system.

Figure 15:
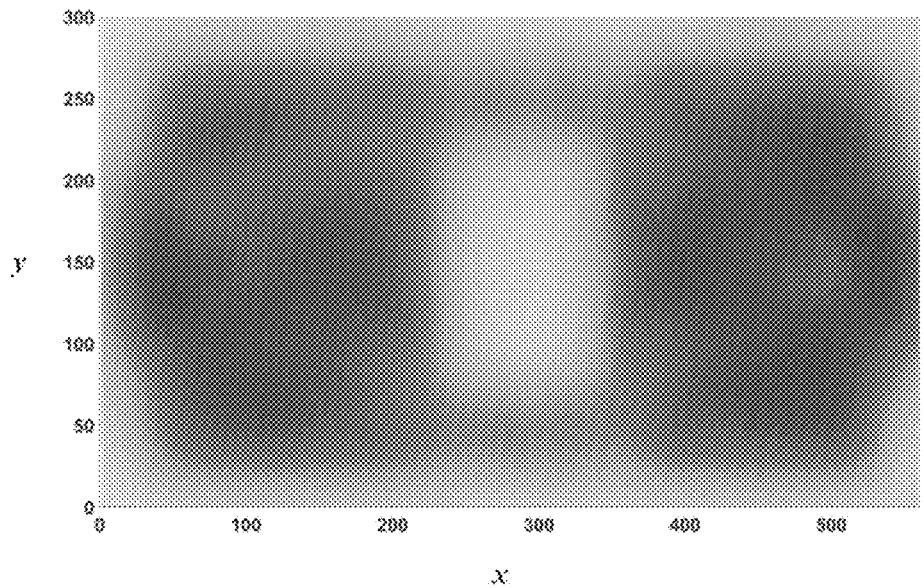

FIG. 15 Illustrates the conventional THz image of Sample 2 developed according to Equation (17).

Figure 16:
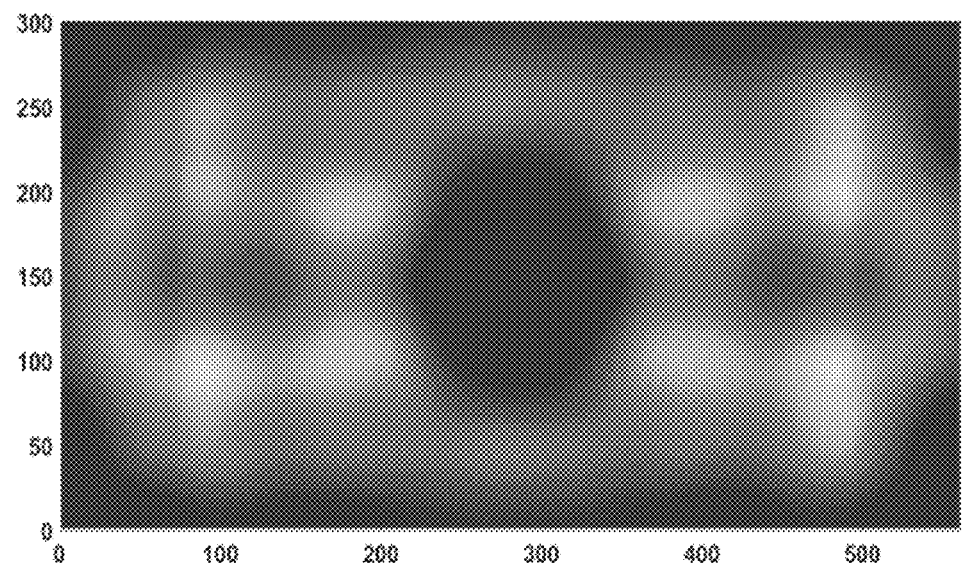

FIG. 16 Illustrates the resulted image from the deconvolution of said measured PSF and the conventional THz image of Sample 2.

FIG. 17 Illustrates the mathematically modeled PSF of the THz imaging system.

Figure 18:
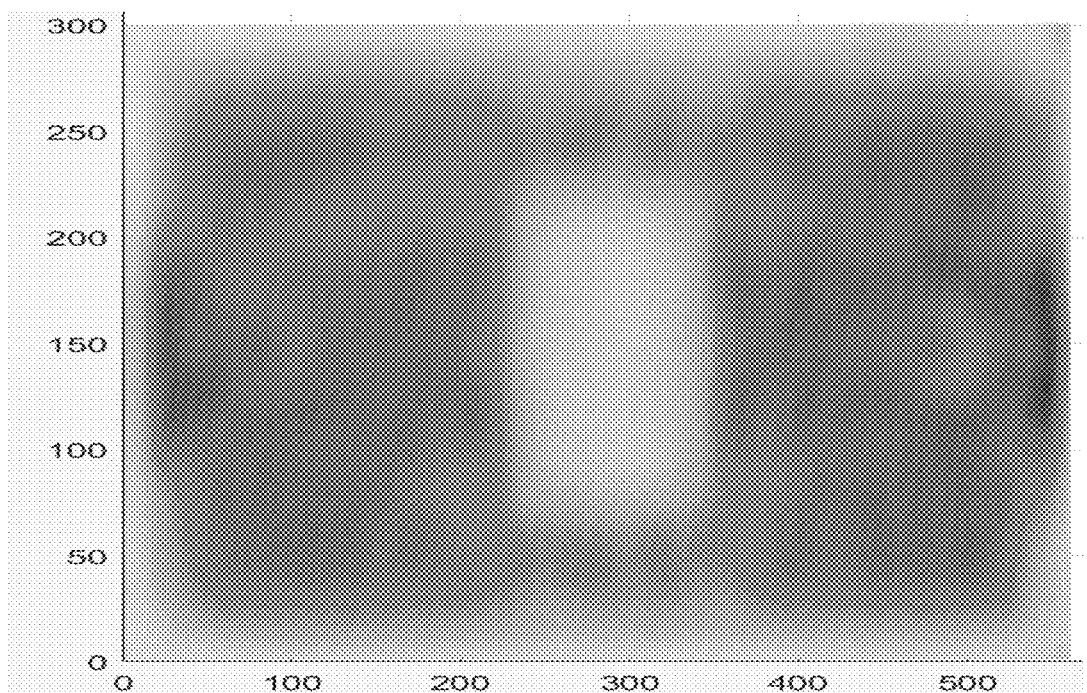
Figure 19:
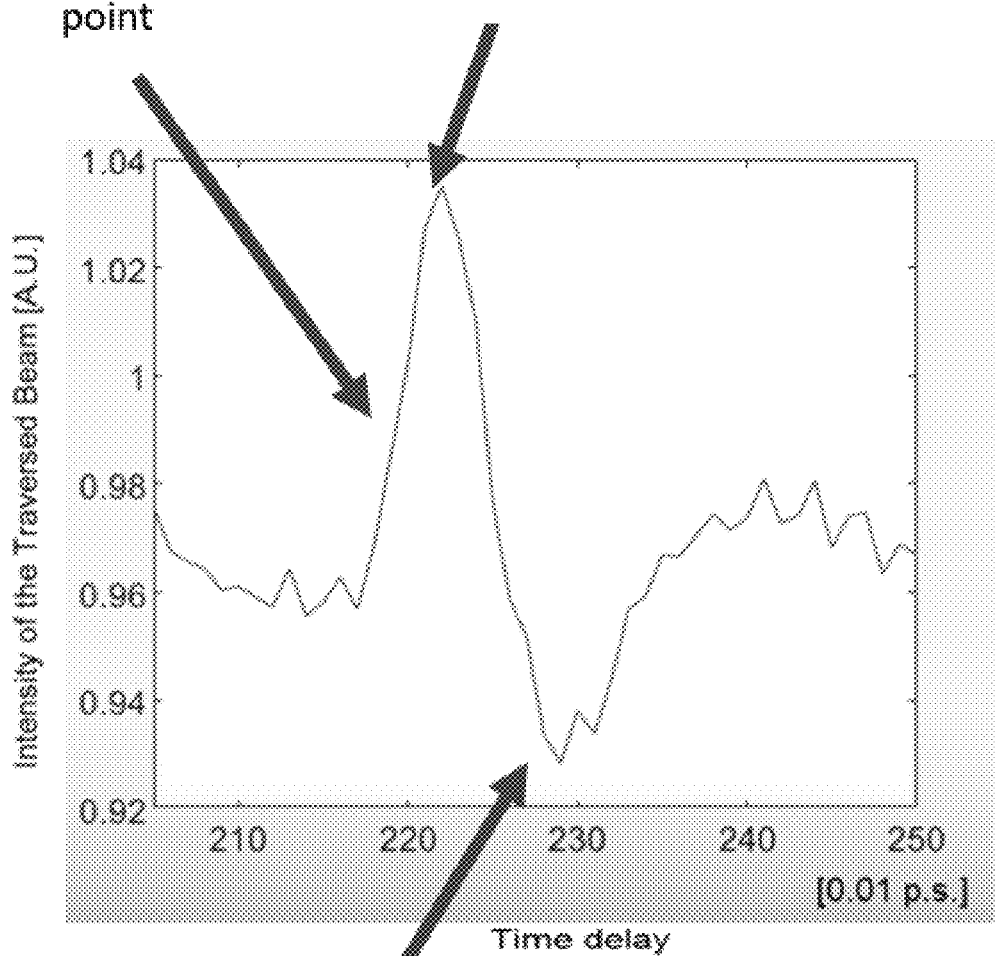

FIG. 18 Illustrates the resulted image from deconvolution of the mathematically modeled PSF and conventional THz image FIG. 19 Illustrates the principle of choosing magnitude of the THz signal at a time delay before the maximum of the THz signal, in accordance with Equation (18).

Figure 20:
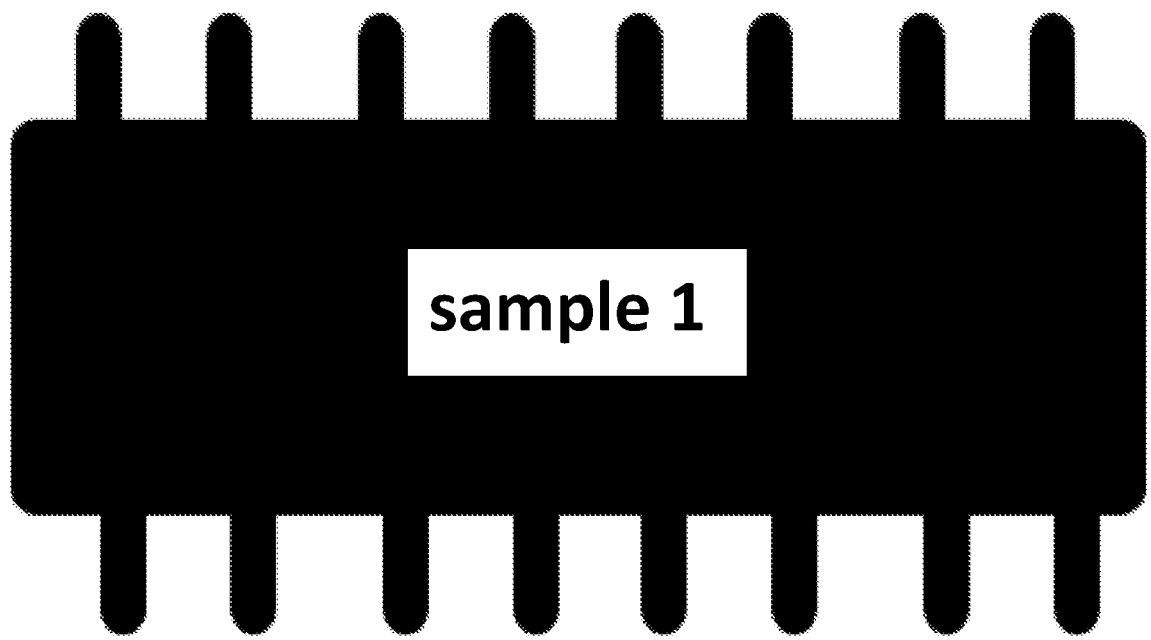
Figure 20:
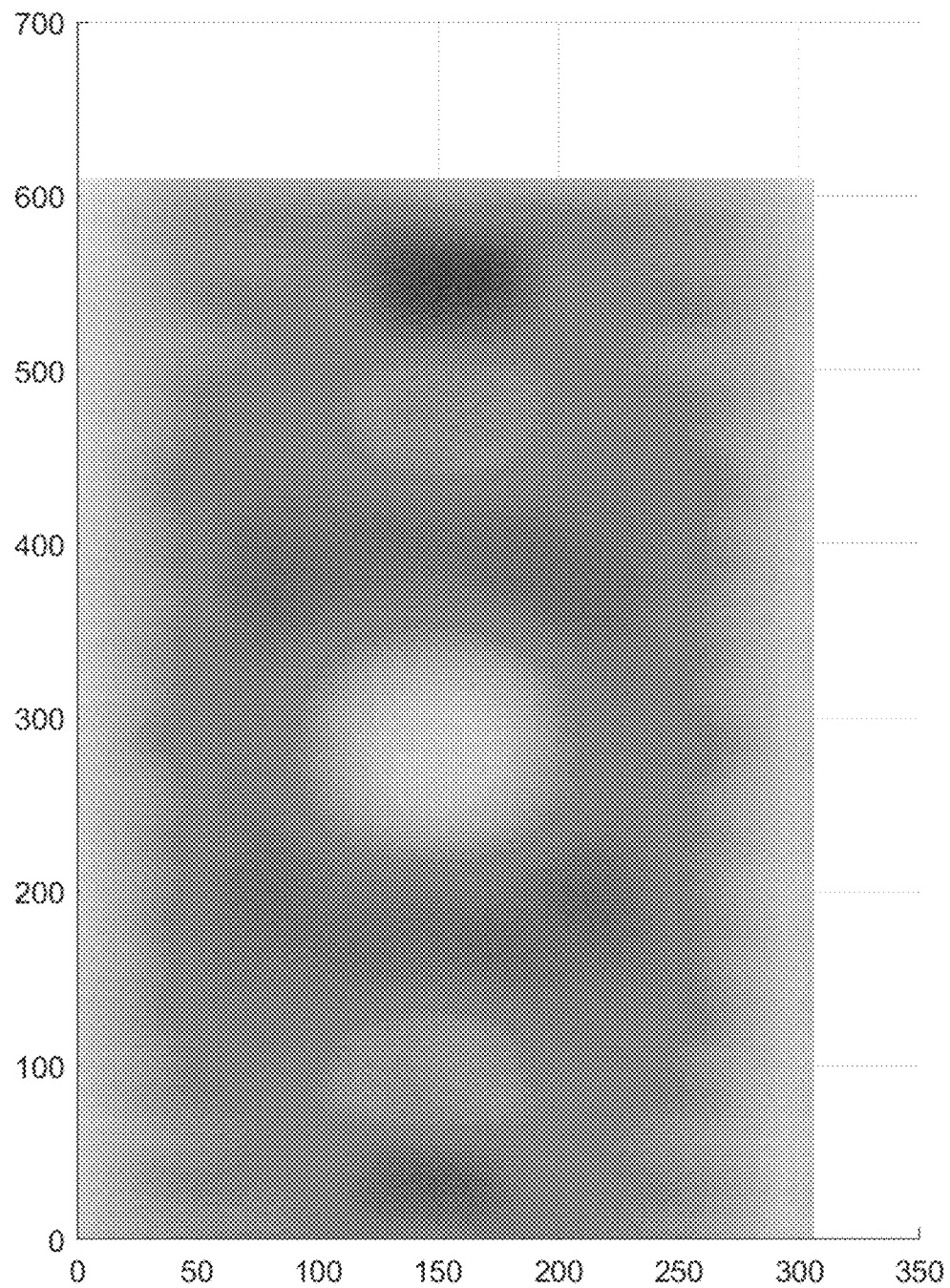
Figure 20:
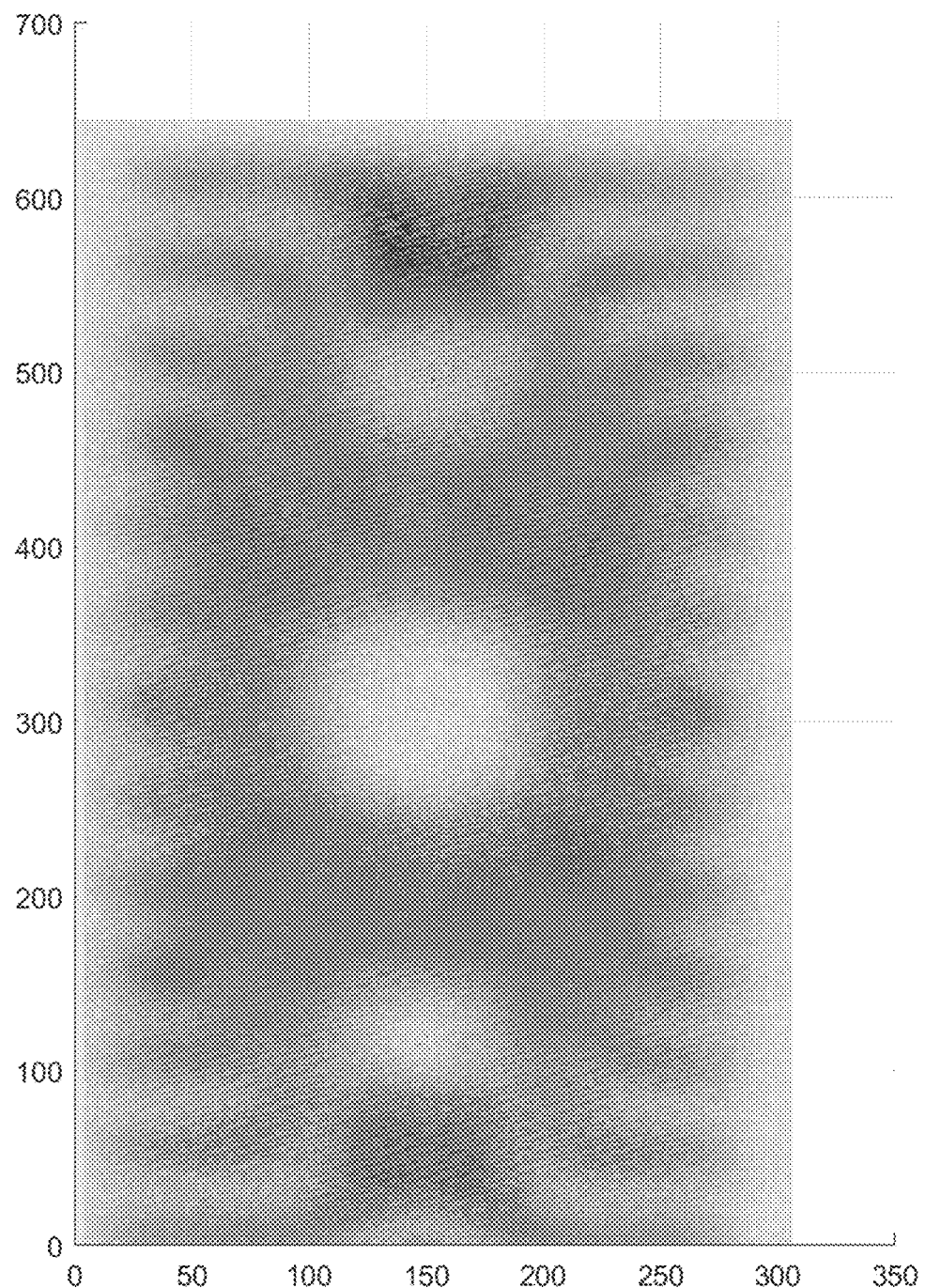
Figure 20:
Figure 20:
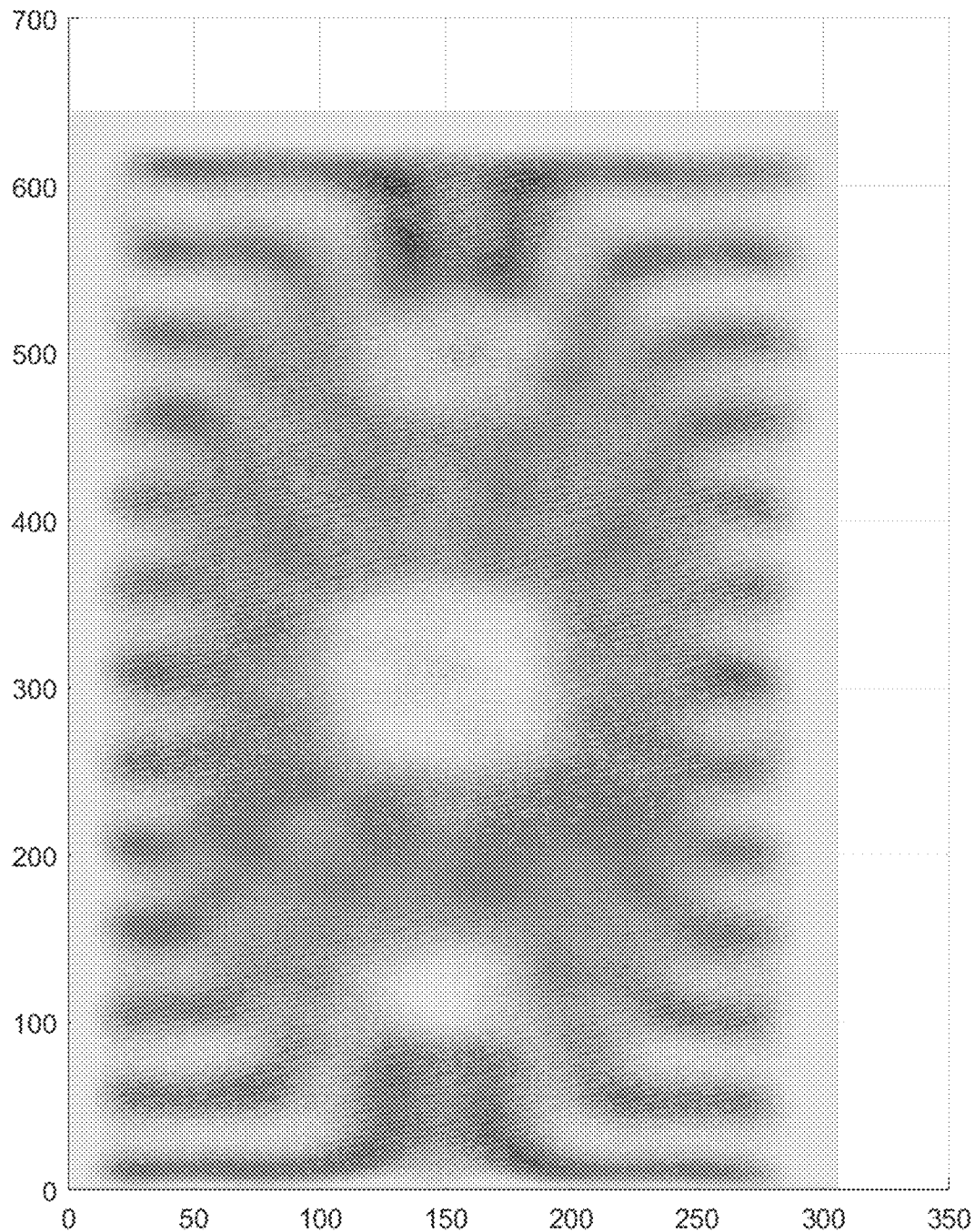
Figure 20:
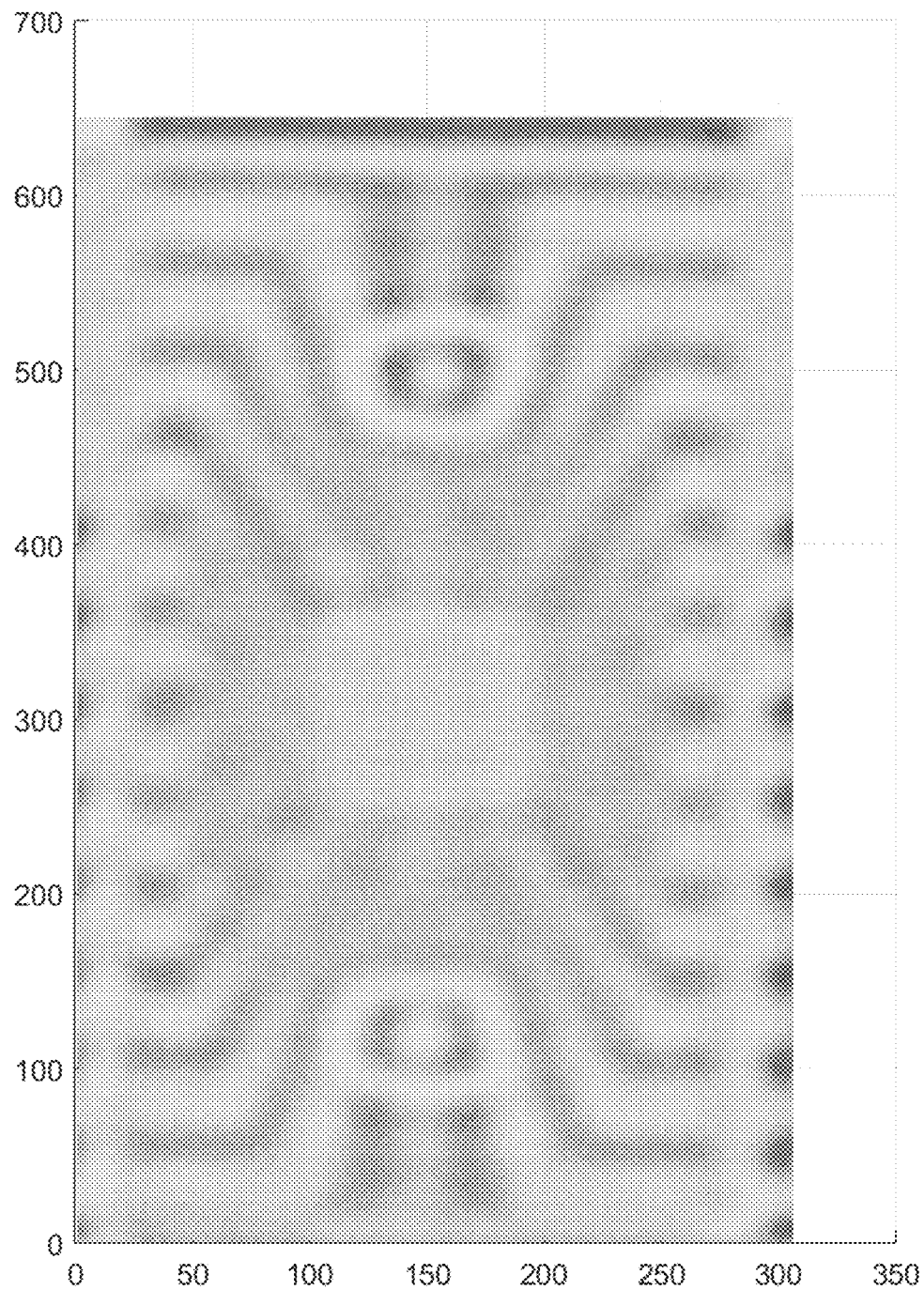
Figure 20:
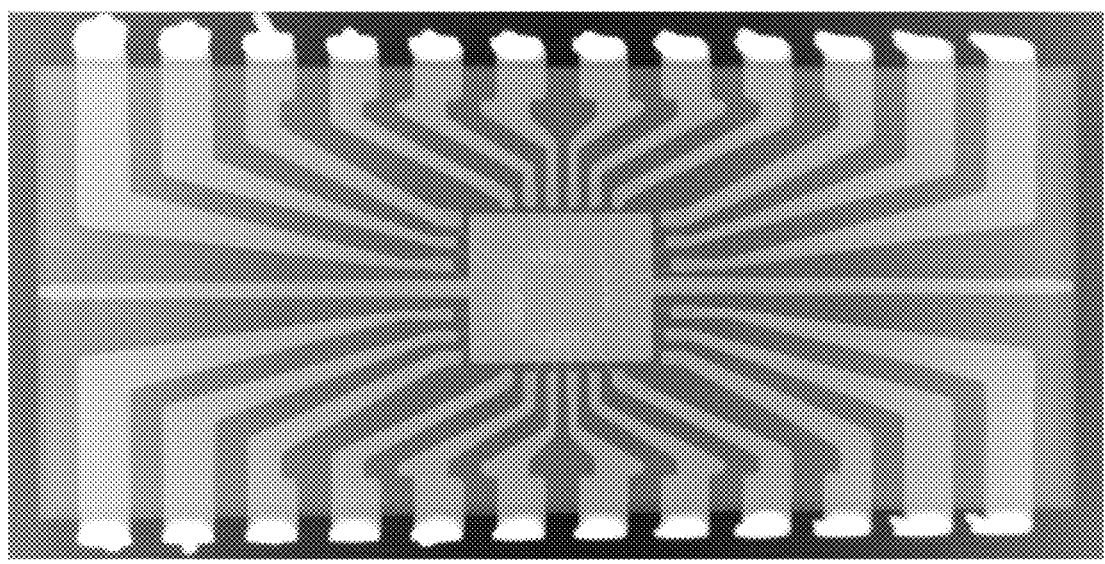
Figure 20:
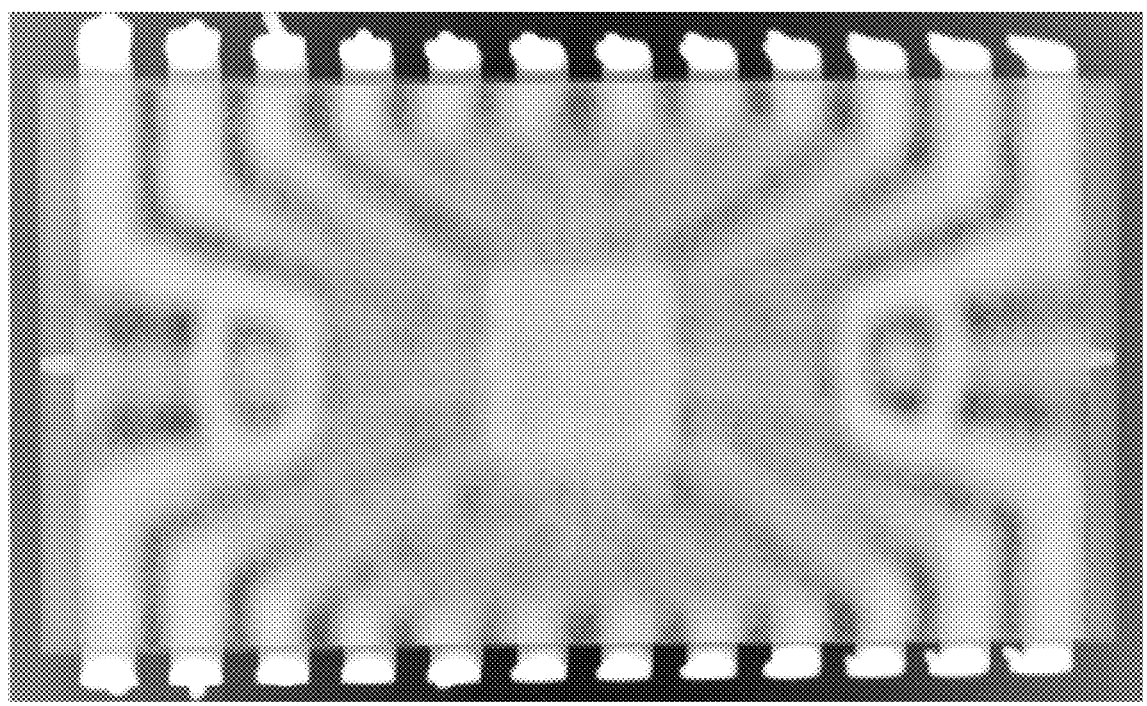
Figure 20:
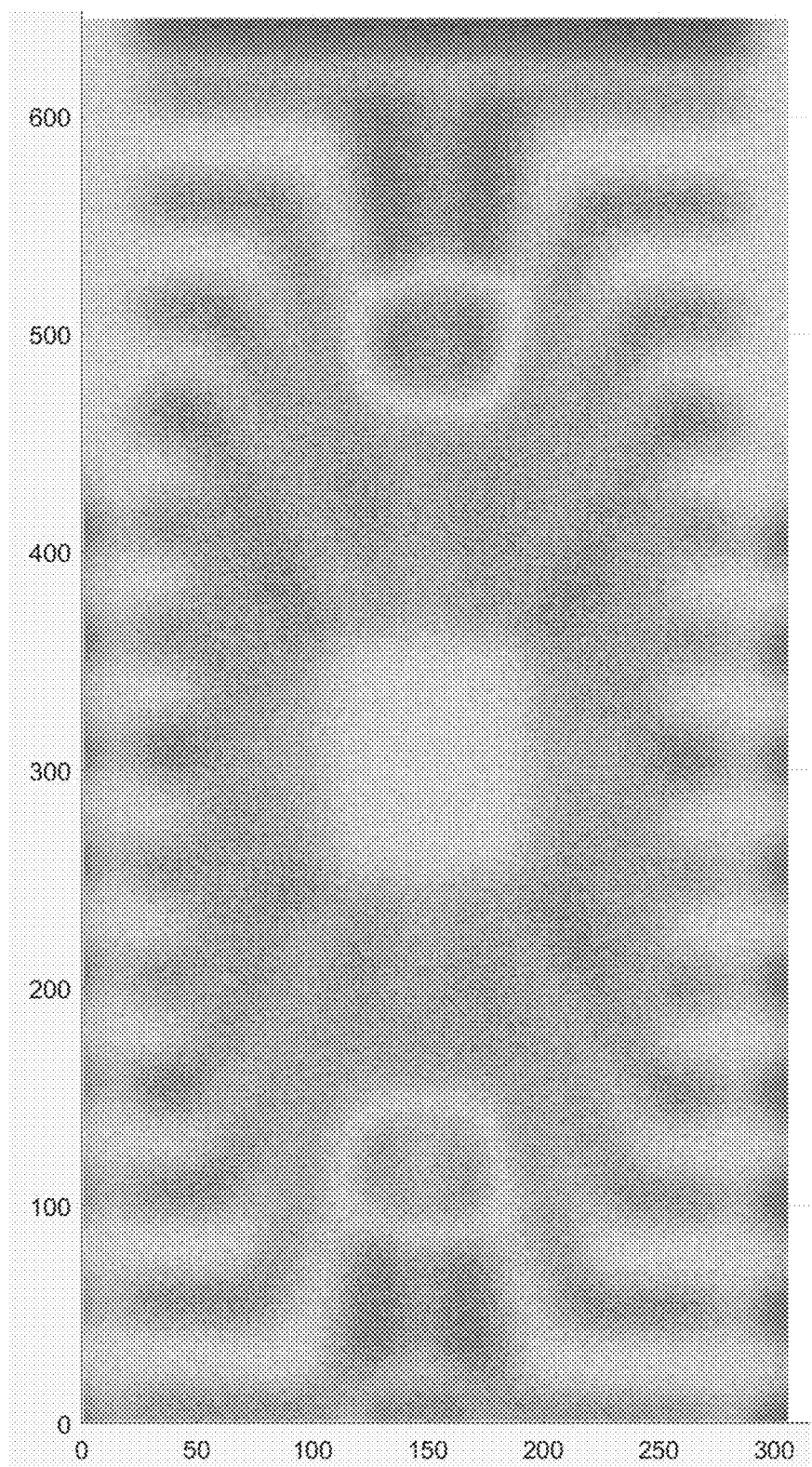
Figure 20:
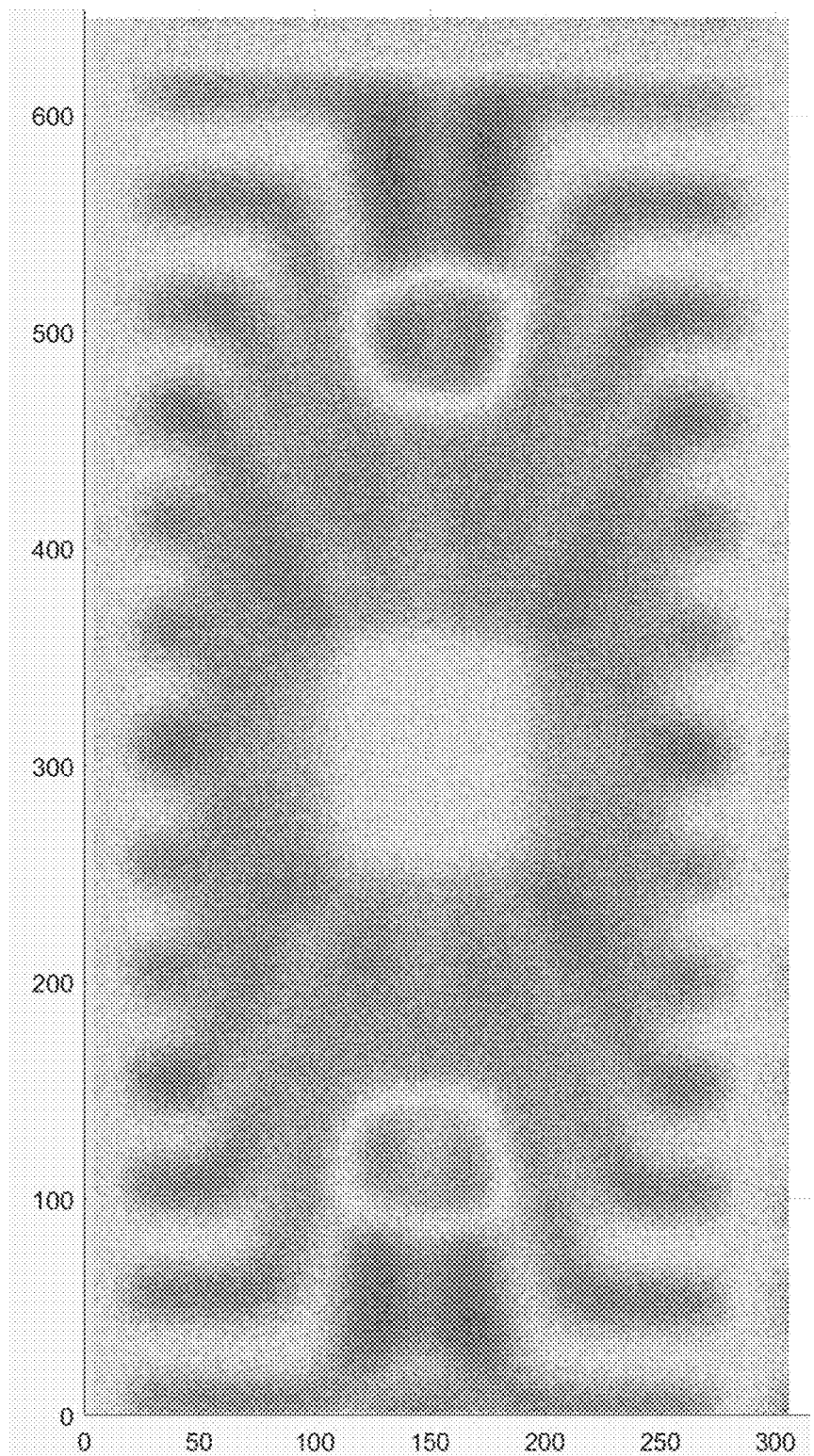

FIG. 20A. Illustrates the visible light image of Sample 1.

FIG. 20B. Illustrates the conventional THz image of Sample 1, developed by Equation (17).

FIG. 20C. Illustrates the THz image of Sample 1 developed by Equation (18).

FIG. 20D. Illustrates the output on 1215 for Sample 1.

FIG. 20E. Illustrates the output on 1215 in case BPF (Band-Pass Filtering) is not applied (only time-domain diffraction suppression (Equation 18) and deconvolution of the THz image and PSF are applied) for Sample 1.

FIG. 20F. Illustrates the output on 1215 in case Equation (17) is used in block 1210 instead of Equation (18): as can be seen in this image the quality of the image is lower and it contains artifacts compared with the image in FIG. 20D.

FIG. 20G. Illustrates the X-ray image of Sample 1.

FIG. 20H. Illustrates an image formed by overlaying said enhanced-resolution THz image (the image in FIG. 20D.) and X-ray image (the image in FIG. 20G.) of Sample 1: confirming the accuracy of the high-resolution THz image.

FIG. 20I. Illustrates the THz image of Sample 1 where only frequency-domain BPF (in 1205) is applied and Equation (17) is used for developing the image (deconvolution and time-domain diffraction suppression (Equation (18)) are not applied). The resolution and quality of this image is lower than the enhanced-resolution image in FIG. 20D where the entire system of FIG. 12A is used to develop the image.

FIG. 20J. Illustrates the THz image of Sample 1 where only BPF (in 1205) and time-domain diffraction suppression (Equation (18) in 1210) is used. The resolution and quality of this image is higher than the image in FIG. 20I where only BPF was applied. The resolution and quality of this image is lower than the enhanced-resolution image in FIG. 20D where the entire system of FIG. 12A was used to develop the image.

FIG. 21A. Illustrates the principle of choosing the magnitude of the THz signal at a time delay before the maximum of the THz signal, in accordance with Equation (21).

FIG. 21B. Illustrates the THz image of Sample 2 developed by using Equation (21).

Figure 22:
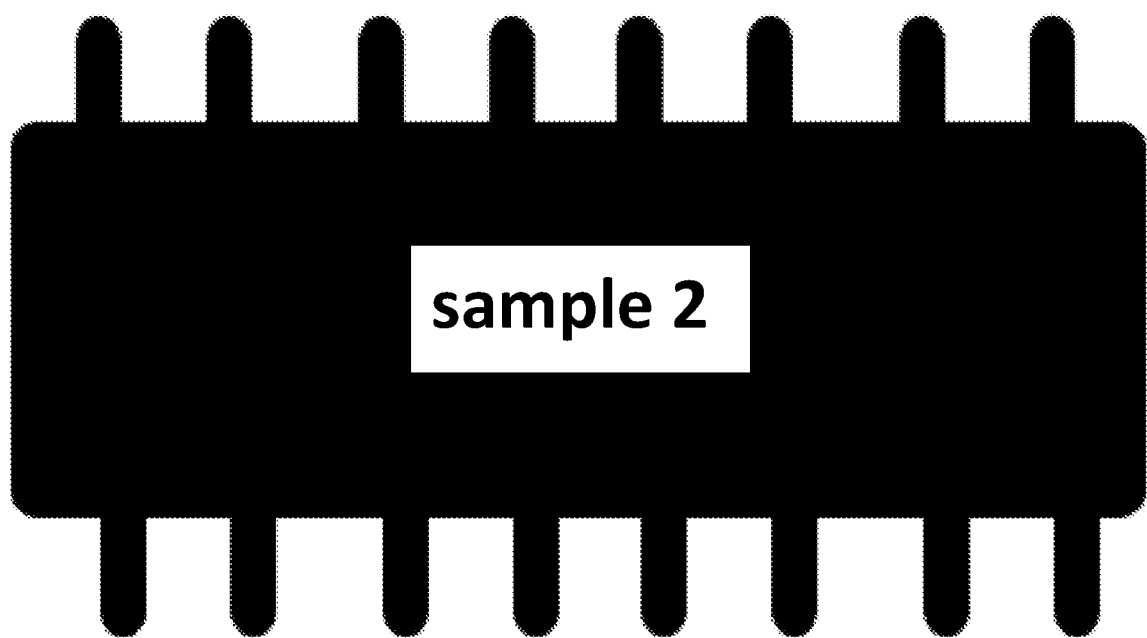
Figure 22:
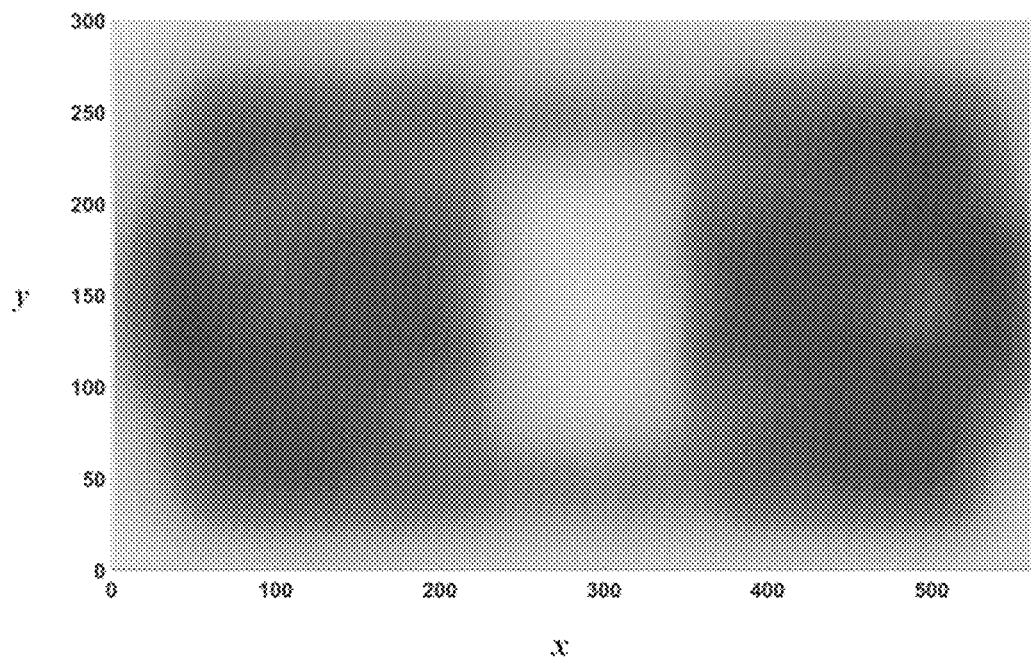
Figure 22:
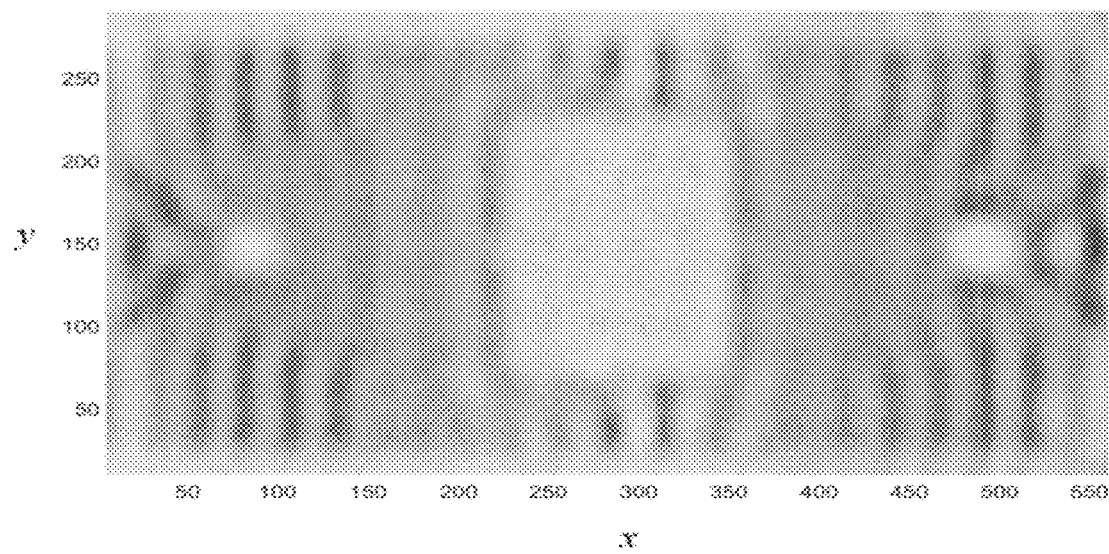
Figure 22:
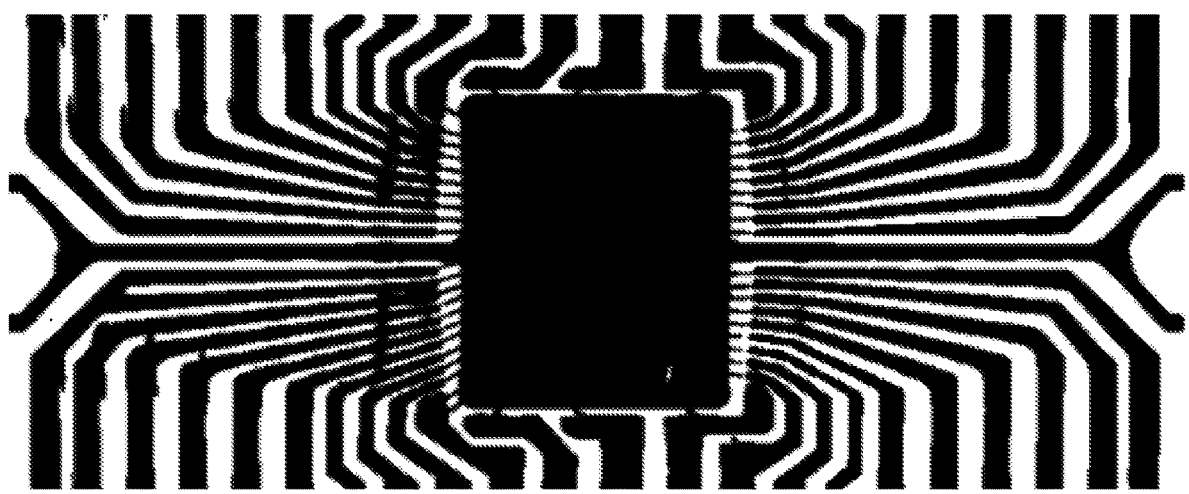
Figure 22:
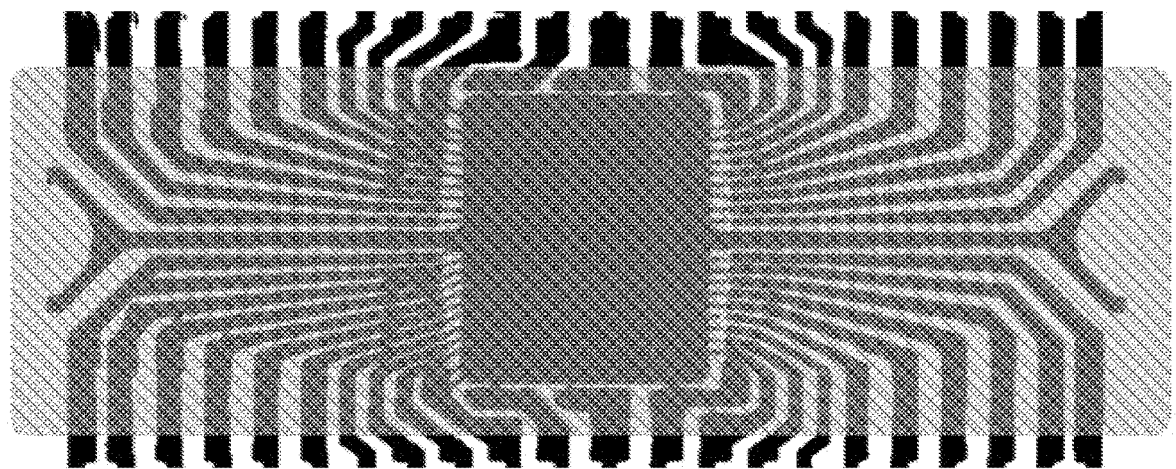
Figure 22:
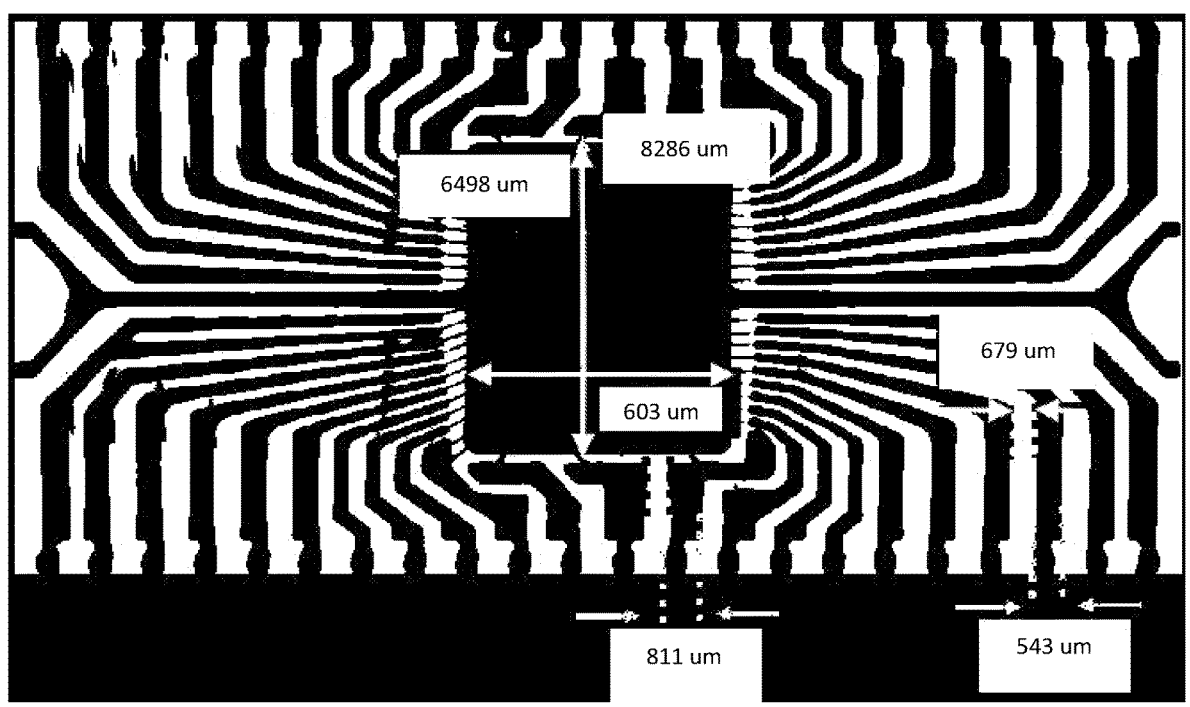
Figure 22:
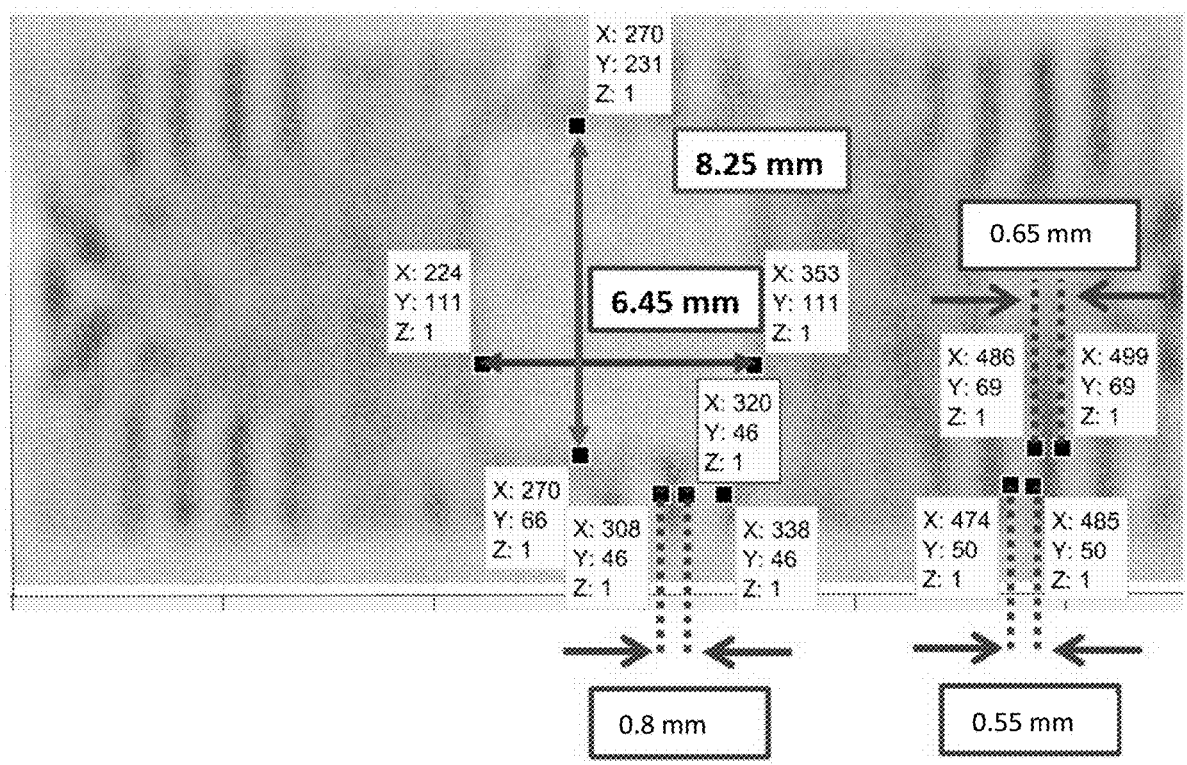
Figure 22:
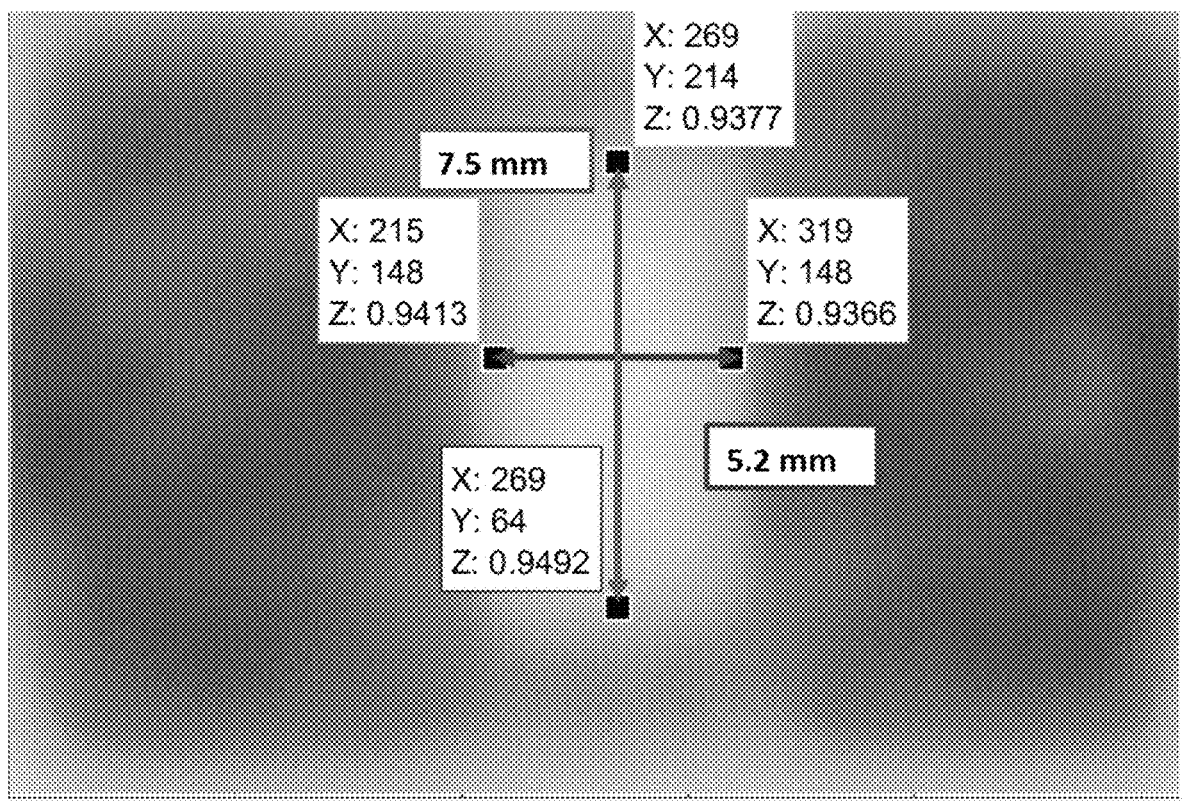
Figure 22:
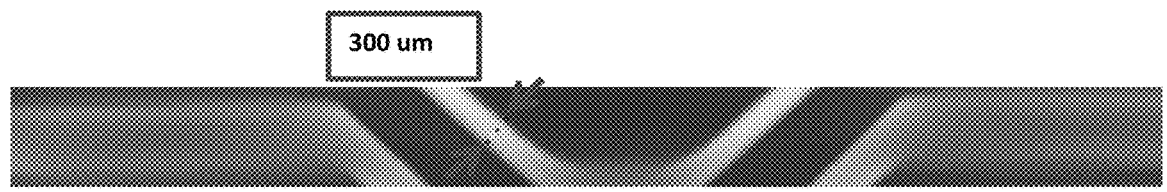
Figure 22:
Figure 22:

FIG. 22A. Illustrates the visible light image of Sample 2.

FIG. 22B. Illustrates the conventional THz image of Sample 2 developed according to Equation (17).

FIG. 22C. Illustrates the enhanced-resolution THz image of Sample 2 (the output of the system of FIG. 12A for Sample 2).

FIG. 22D. Illustrates the X-ray image of Sample 2.

FIG. 22E. Illustrates an image formed by overlaying said enhanced-resolution THz image (the image in FIG. 22C.) and X-ray image (the image in FIG. 22D.) of Sample 2: confirming the accuracy of the enhanced-resolution THz image.

FIG. 22F. Illustrate the X-ray image of Sample 2 with measured features on it.

FIG. 22G. Illustrates the enhanced-resolution THz image (output of the 1215 of system of FIG. 12A) for Sample 2 and measured features on it.

FIG. 22H. Illustrates the conventional THz image of Sample 1 (THz image of FIG. 22B.) with measured features on it.

FIG. 22I. Illustrates a fine wire in Sample 2 imaged by X-Ray.

FIG. 22J. Illustrates a fine wire in Sample 2 imaged by the system of FIG. 12A

FIG. 22K. Illustrates the conventional THz image of Sample 2: the fine wire observed in FIG. 22I. and FIG. 22J. cannot be observed here due to the poor resolution.

Figure 23:
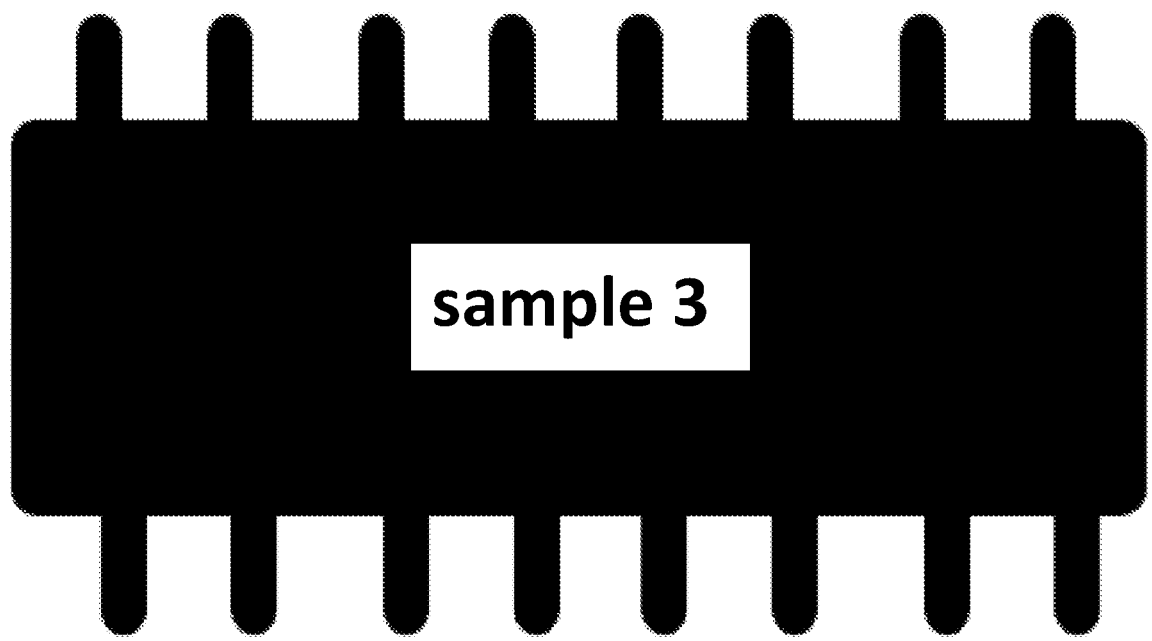
Figure 23:
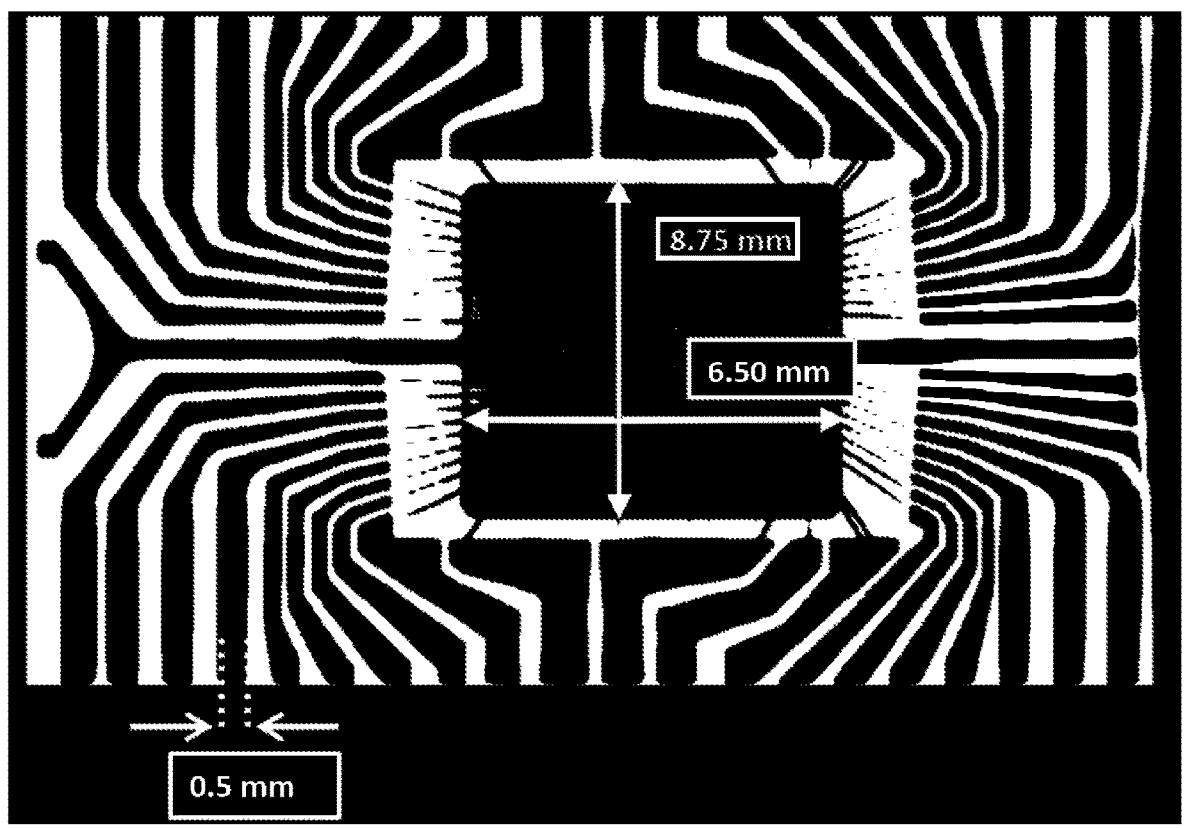
Figure 23:
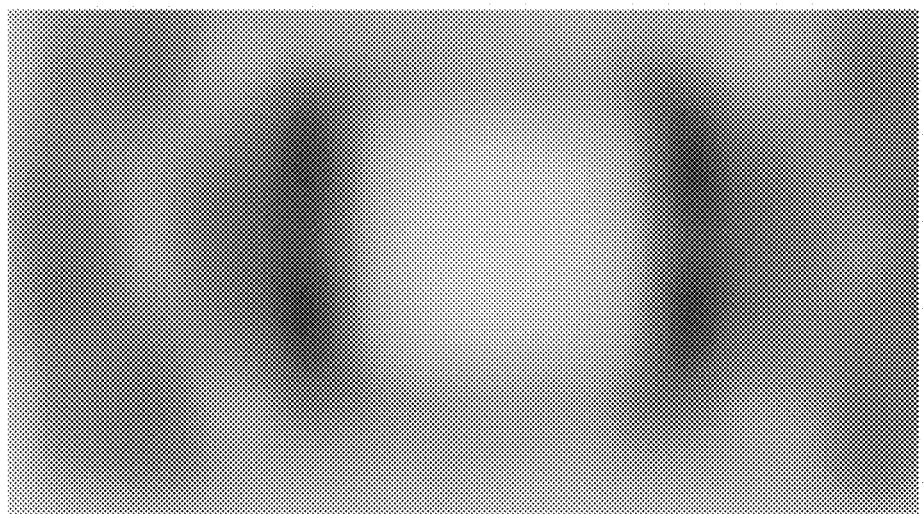
Figure 23:
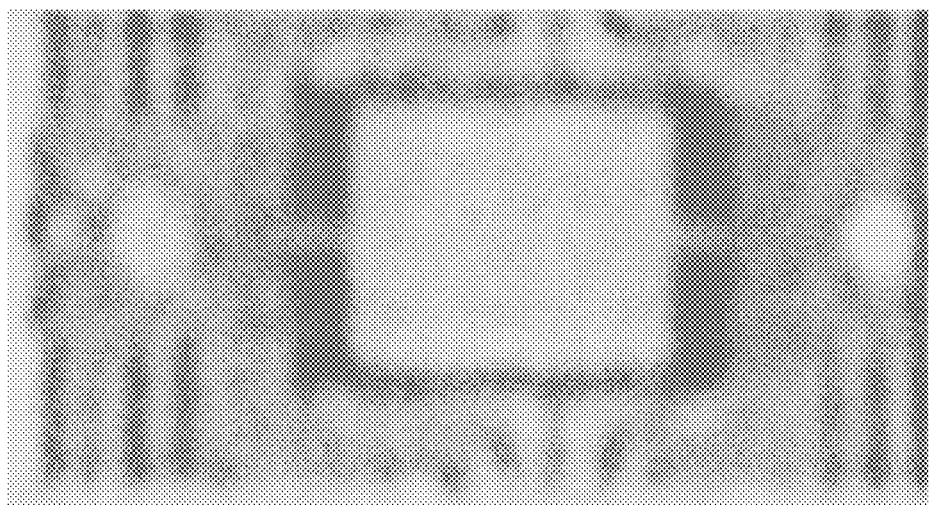
Figure 23:
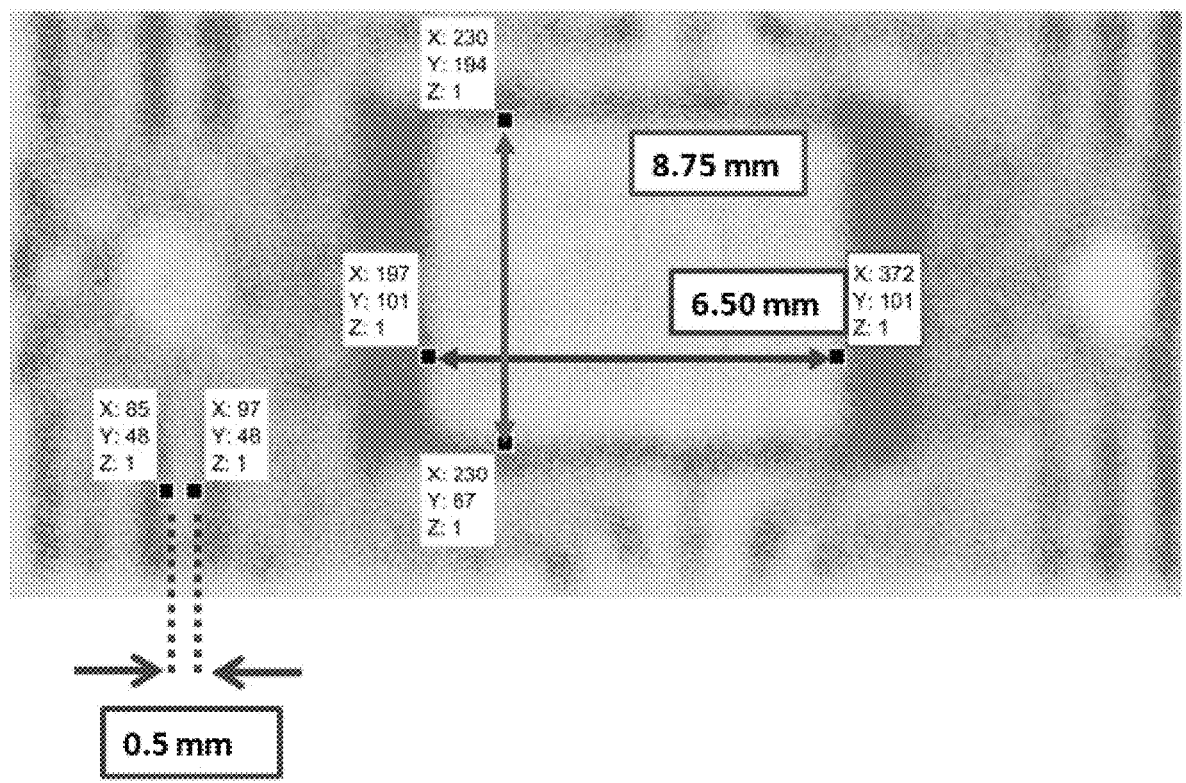

FIG. 23A. Illustrates the visible light image of Sample 3.

FIG. 23B. Illustrates the X-ray image of Sample 3 with measured features on it.

FIG. 23C. Illustrates the THz image of Sample 3 developed using the conventional method (using Equation (17)).

FIG. 23D. Illustrates the enhanced-resolution THz image of Sample 3 (the output of the system of FIG. 12A for Sample 3).

FIG. 23E. Illustrates the enhanced-resolution THz image of Sample 3 with measured features on it.

FIG. 24A. Illustrates a Graphical User Interface (GUI) prototype for operating the resolution-enhancement system of FIG. 12A implemented by digital computers wherein Sample 1 is processed.

FIG. 24B. Illustrates a Graphical User Interface (GUI) prototype for operating the resolution-enhancement system of FIG. 12A implemented by digital computers wherein Sample 2 is processed.

FIG. 24C. Illustrates a Graphical User Interface (GUI) prototype for operating the resolution-enhancement system of FIG. 12A implemented by digital computers wherein Sample 3 is processed.

DRAWINGS-REFERENCE NUMERALS

201 Face of a person who is wearing a face mask
202 The body of the disclosed device
203 Digital display and panel for receiving the input and commands from the user
204 Handle of the disclosed device
205 Emitter of THz beam
206 Receiver of THz beam
207 A Face mask worn by the person
301 Intensity of the emitted (reference) THz pulse from 205 vs. time

401 First peak (part of the emitted THz beam that is reflected from the face mask, 207) of the reflected THz beam received by 206 vs. time

402 Second peak (part of the emitted THz beam that is reflected from the face of the person, 201) of the reflected THz beam received by 206 vs. time

501 First peak (part of the emitted THz beam that is reflected from the face mask, 207) of the reflected THz beam received by 206 vs. time

502 Second peak (part of the emitted THz beam that is reflected from the face of the person contaminated with body fluids) of the reflected THz beam received by 206 vs. time; the intensity of 502 is less than that of 402 which is an indication of existence of body fluids on the face of the person

601 First peak (part of the emitted THz beam that is reflected from the face mask contaminated with body fluids) of the reflected THz beam received by 206 vs. time; the intensity of 601 is less than that of 401 which is an indication of existence of body fluids on the mask face

602 Second peak (part of the emitted THz beam that is reflected from the face of the person who wears a face mask contaminated with body fluids) of the reflected THz beam received by 206 vs. time; the intensity of 602 is less than that of 402 because the face mask is contaminated with body fluids; by additional computations it can be determined if the face of the person is also contaminated.

701 Intensity of the received THz beam reflected from parts of the face or the mask, or both, where no body fluid contamination exists

702 Intensity of the received THz beam reflected from parts of the face or the mask, or both, where body fluid contamination exists.

703 Intensity of the received THz beam reflected from parts of the face or the mask, or both, where no body fluid contamination exists.

801 A group of pixels on the THz image with intensities lower than the rest of the pixels which is an indication of body fluids.

802 The trace of a waterdrop leaked from the runny nose of a person identified on the enhanced-resolution THz image.

803 Reconstructed version of the trace of a waterdrop leaked from the runny nose of a person identified on the enhanced-resolution THz image.

901 A group of pixels on the THz image with intensities lower than the rest of the pixels but higher than that of 801 which is an indication of contamination or dried body fluids.

1001 Spectrum of the reflected THz signal reflected from a clean spot (either on the face or on the face mask).

1002 Spectrum of the reflected THz signal reflected from a clean spot (either on the face or on the face mask).

1003 Spectrum of the reflected THz signal reflected from a contaminated spot (either on the face or on the face mask).

1101 Positioning the emitter and the receiver in front of the face of the person, which can be done manually by an operator or automatically by a microcontroller and electrical motors.

1102 Scanning the face of the person, which can be done manually by an operator or automatically by a microcontroller and electrical motors.

1103 Receiving the reflected THz beam by the receiver of the THz beam, 205.

1104 Converting the received THz beam from time-domain to frequency-domain using FFT.

1105 Analyzing the spectrum profile of the beam for finding traces of contamination or body fluids.

1106 Determining if the scanned spot is cleaned, contaminated, or there is body fluid on it.

1107 Device for displaying and/or storing the results, for example a digital display or a digital memory.

1205 Band-pass filter (BPF)

1206 The unit that selects and gives the spectrum of the imaging pulse (Sample THz pulse and Reference THz pulse) to the PSF modeler

1207 Data input: Optical, Sample, and System Parameters

1208 Computation unit: PSF Modeler

1209 Computation unit: Inverse Fast Fourier transform (IFFT)

1210 Time-Domain Filter (TDF) Diffraction Suppression Unit wherein the intensity of the pixel at each coordinate (i,j) is computed according to the principle of Equation (18) or Equation (21)

1211 Unit whereby pixels are mapped on the digital image

1212 Logic unit for checking if the entire sample is processed

1213 Moving to the next pixel

1214 Computation unit: deconvolution

1215 Memory and/or Display Unit: Displaying and/or storing the enhanced-resolution THz image

1216 Unit whereby the digital image is processed for finding traces of contamination or body fluid

1217 Determining if the scanned spot is cleaned, contaminated, or there is body fluid on it

1218 Memory and/or Display Unit: Displaying and/or storing the results of the diagnosis

1305 Computation unit for analyzing the time domain of the signal

2401 Raw THz image developed by using Equation (17) where both reference and sample THz pulses are used to compute the intensity of pixels

2402 Conventional THz image of the sample developed by using Equation (17) where only sample THz pulses are used to compute the intensity of pixels

2403 THz image of the sample developed by using Equation (18) (used in block 1210)

2404 THz image of the sample developed by deconvolution of the THz image of block 2403 and PSF of block 2413

2405 THz image developed by frequency-domain filtered THz pulses where BPF in block 1205 is activated and Equation (18) in block 1210 is used

2406 Enhanced-resolution THz image (equivalent to the output of the system of FIG. 12A in block 1215)

2407 Equivalent to block 1207 whereby Optical, Sample, and System Parameters are entered to the system to be used in block 1208

2408 Cut-off frequencies of the BPF (in block 1205) are entered to the system by this block

2409 Time interval of the sample THz pulse is entered in this box

2410 The sample THz pulse

2411 The sample THz pulse that is used for developing the PSF, this block, together with the reference THz pulse, is equivalent of 1206 in the system of FIG. 12A

2412 Attenuation coefficient of the object developed according to Equation (12)

2413 PSF developed according to PSF Equation (16), where the BPF in 1205 is bypassed (the full spectrums of the THz beams are used as inputs to the PSF equation). This PSF is used to develop the image in 2404

2414 PSF developed according to PSF Equation (16), where the BPF in 1205 is not bypassed (the filtered spectrums of the THz beams are used as inputs to the PSF equation). This PSF is used to develop the enhanced-resolution image in 2406

DETAILED DESCRIPTION OF THE INVENTION

Figure 1:
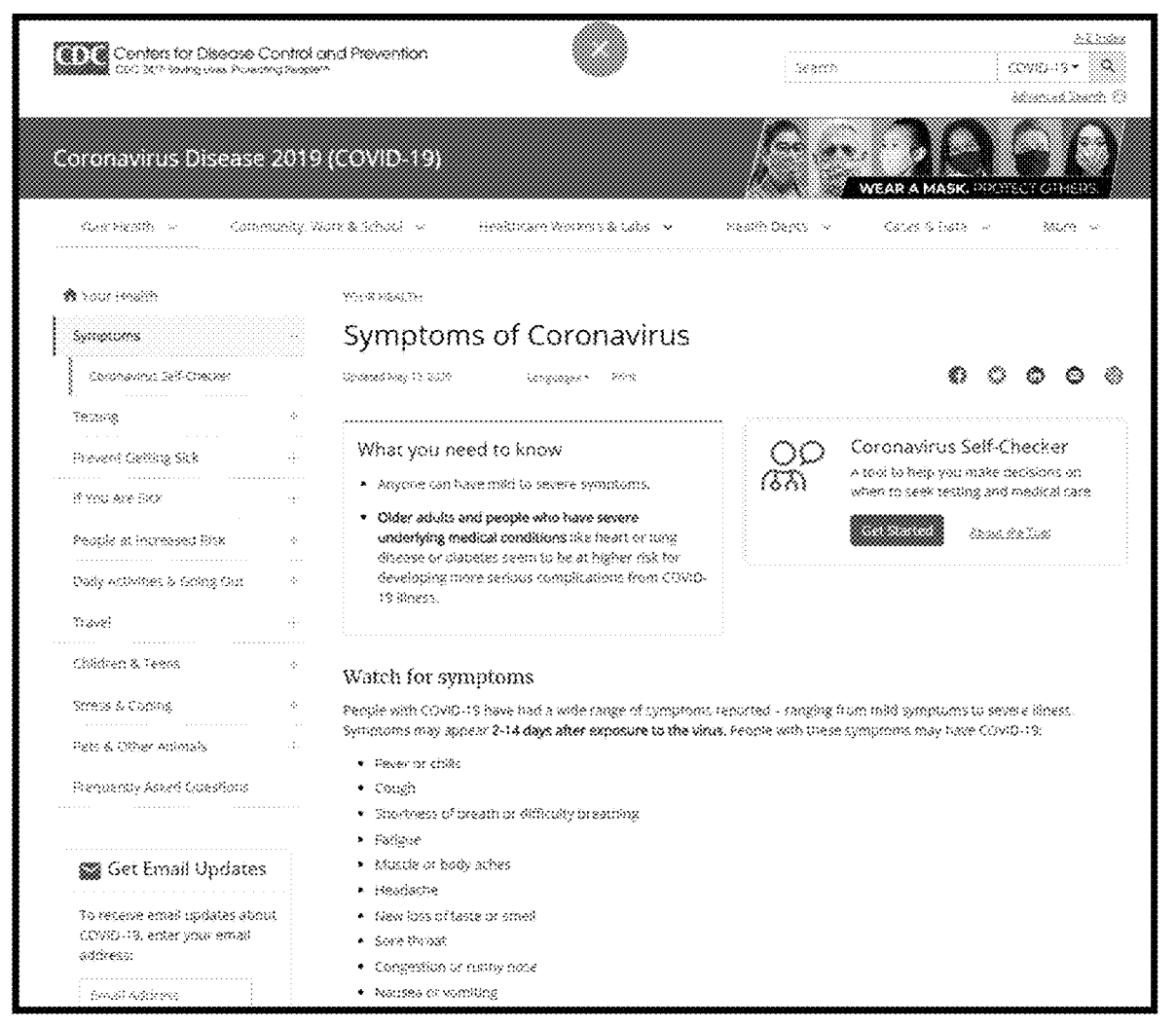

FIG. 1. Illustrates a screen shot captured from the website of CDC on Sep. 28, 2020 (https://www.cdc.gov/coronavirus/2019-ncov/symptoms-testing/symptoms.html) According to the guidelines published by CDC, cough, congestion or runny nose, are among the symptoms of COVID-19.

Toward prevention of the spread of COVID-19 virus and for suppressing the pandemic caused by this outbreak, many local governments, states within the Unites States, and countries around the globe have mandated wearing of face covering masks.

A mask covers the face of the mask wearer and thus, conceals some of the symptoms of COVID-19 such as runny nose or existence of body fluids on the face of the mask wearer. In addition, the inside surface of the mask, that is not visible while the person is wearing the mask, may be contaminated by the body fluids (as a result of coughing or runny nose).

In other words, although masks are mandated for prevention of the spread of COVID-19, they conceal some of the symptoms of this disease.

Billions are dedicated to new spending for public health imaging technology [1]. To prevent spread of COVID-19, people in the society are constantly being tested for symptoms of this disease. As an example, upon entering a person to a building, body temperature of the person is measured by using infrared thermometer handheld devices. However, according to the website of CDC, fever is only one of the symptoms of COVID-19 [2]. It is possible that a person contracted by COVID-19 does not show fever at the time of examination [3]. The more symptoms are measured, the higher the probability of detecting if a person has COVID-19 illness.

Figure 2:
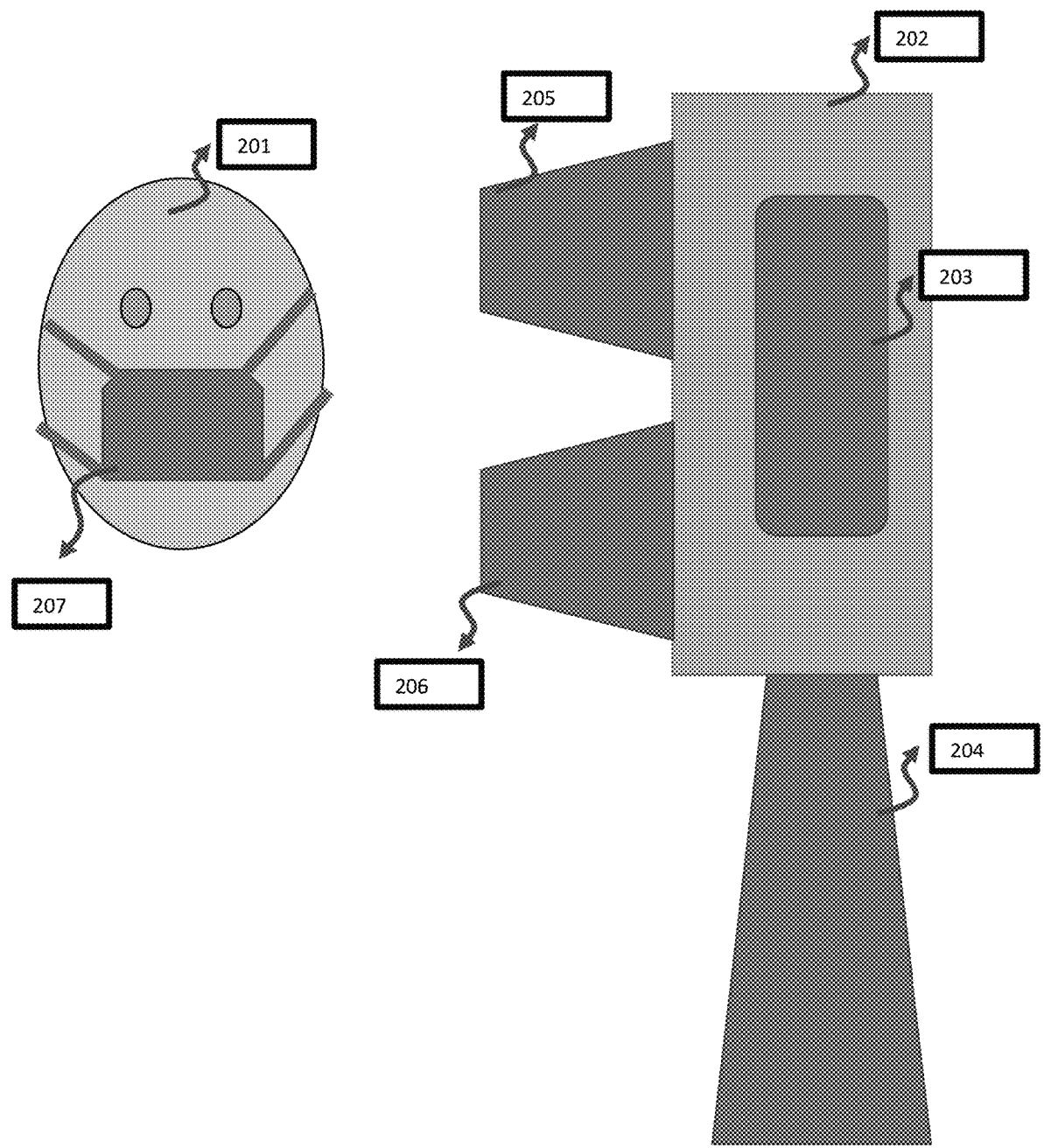
FIG. 2 illustrates the disclosed device positioned in front of the face of a person who is wearing a mask.

FIG. 2 illustrates a person, 201, under examination for symptoms of COVID-19, by the disclosed device, 202, positioned in front of the face of the person, 201, who is wearing a mask, 207. 203 is a digital display for displaying the results of examination and for displaying messages that the computer system of the disclosed device communicates to the operator of the device. 203 is also a panel for receiving the commands from the operator. 204 is the handle for holding the device in front of the face of the person, 201. 205 is an emitter that emits electromagnetic beams in the frequency range of THz. 206 is a receiver that detects electromagnetic beams in the frequency range of THz.

Figure 3:
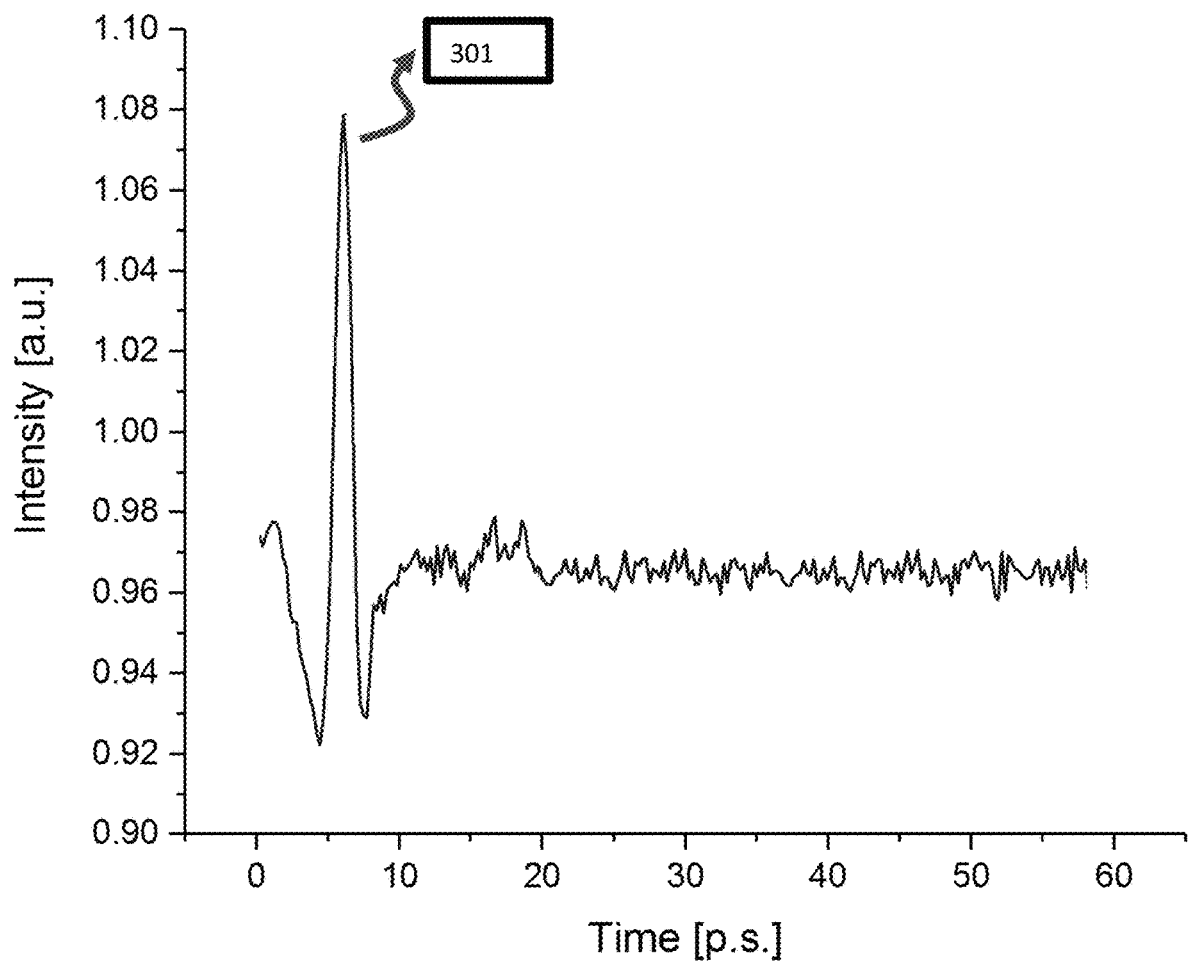
FIG. 3 illustrates the time-domain profile of the reference THz beam.
Figure 4:
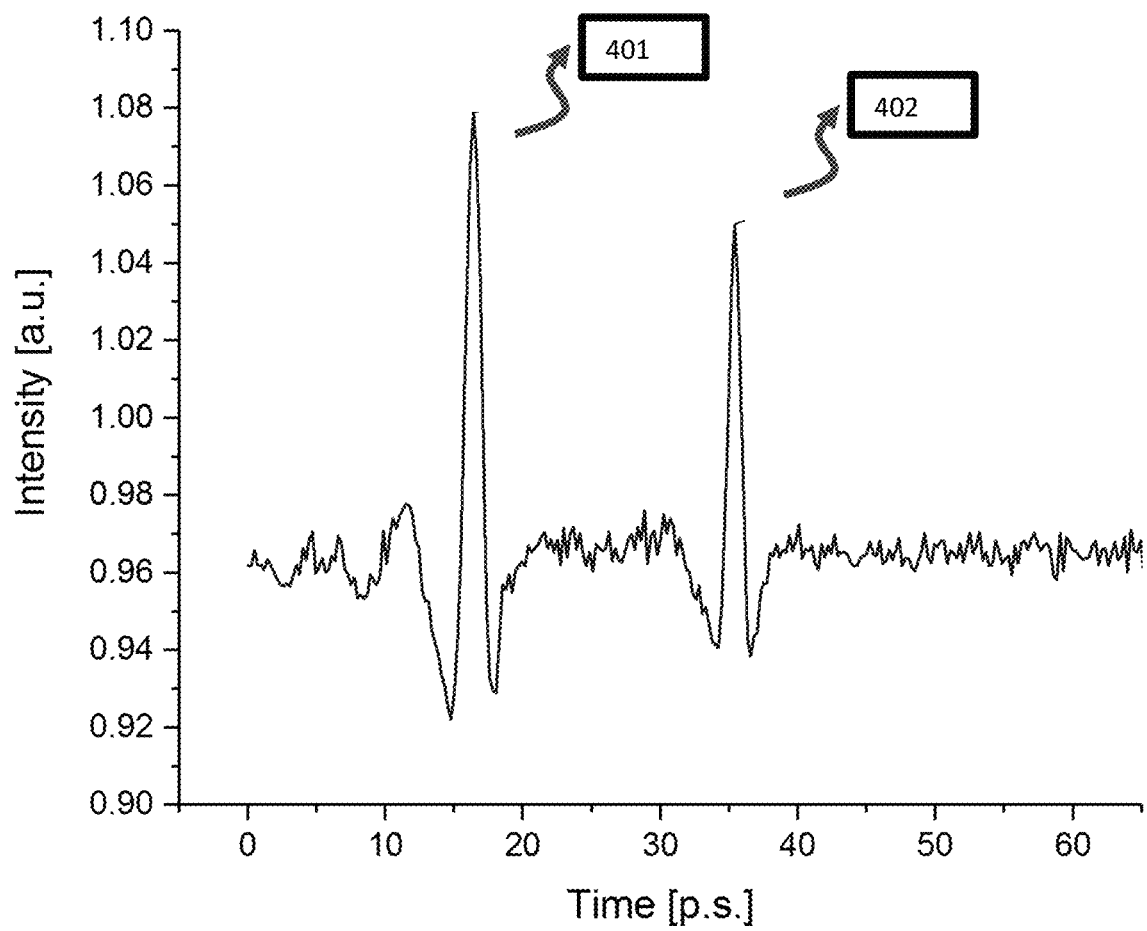
FIG. 4 illustrates the time-domain profile of the reflected THz beam. The first peak, 401, is part of the beam that is reflected from the mask and the second peak, 402, is part of the beam that is reflected from the face of the user.

FIG. 3 illustrates the time-domain profile of the reference THz beam emitted by 205. THz-TDS systems are capable of recording the time-domain profile of THz radiation. This profile includes a peak, 301, where the intensity of the reference THz beam is maximum. As the reference THz beam reaches the face covering mask, part of the beam passes through the face covering mask and part of the beam gets reflected (since the refractive index of the mask is different from that of the air) [19]. The part of the beam that gets reflected from the mask, 207, has less distance (as compared with the part of the beam that is reflected from the face of the person) to get to the THz receiver, 206. Hence, on the time-domain profile of the reflected THz beam, illustrated in FIG. 4, (reflected from a mask wearing person), there will be at least two peaks. The peak with less time delay, 401, is the part of the beam that is reflected from the mask, and the peak with higher time delay, 402, is the part of the beam that is reflected from the face of the person. Depending on the depth resolution in time-of-flight of the TDS-THz system, 401 might be composed of two separate peaks, one reflected from the outer surface of the mask and the other reflected from the inner surface of the mask.

Molecules of water show high absorption in THz frequency regime [18]. At the same time, THz beams (unlike beams of visible light) can pass through the face mask. This disclosure proposes using THz beams for scanning the inner surface of the mask and the face of a mask wearing person for detecting traces of runny nose, cough, and congestion, which are symptoms of COVID-19. Since THz beams (unlike beams of visible light) can pass through the face mask, the person does not need to remove the mask for this examination.

In addition to evaluating traces of molecules of water, detection of congestion and mucus may be performed by measuring the reflection of the THz beam, reflected from the mouth, throat, or nose of the person, received by the THz receiver and determining if the time delay is lower than expected (which is an indication of the fact that due to congestion the beam has been reflected earlier than getting to the end of the nose or throat). As will be described in the following, these symptoms can also be detected by evaluating the frequency-domain of the THz beam which provides insight about reflecting materials. As will be described in the following, these symptoms can also be detected by developing a THz image and evaluating the image for observing traces of runny nose, mucus and congestion.

Figure 5:
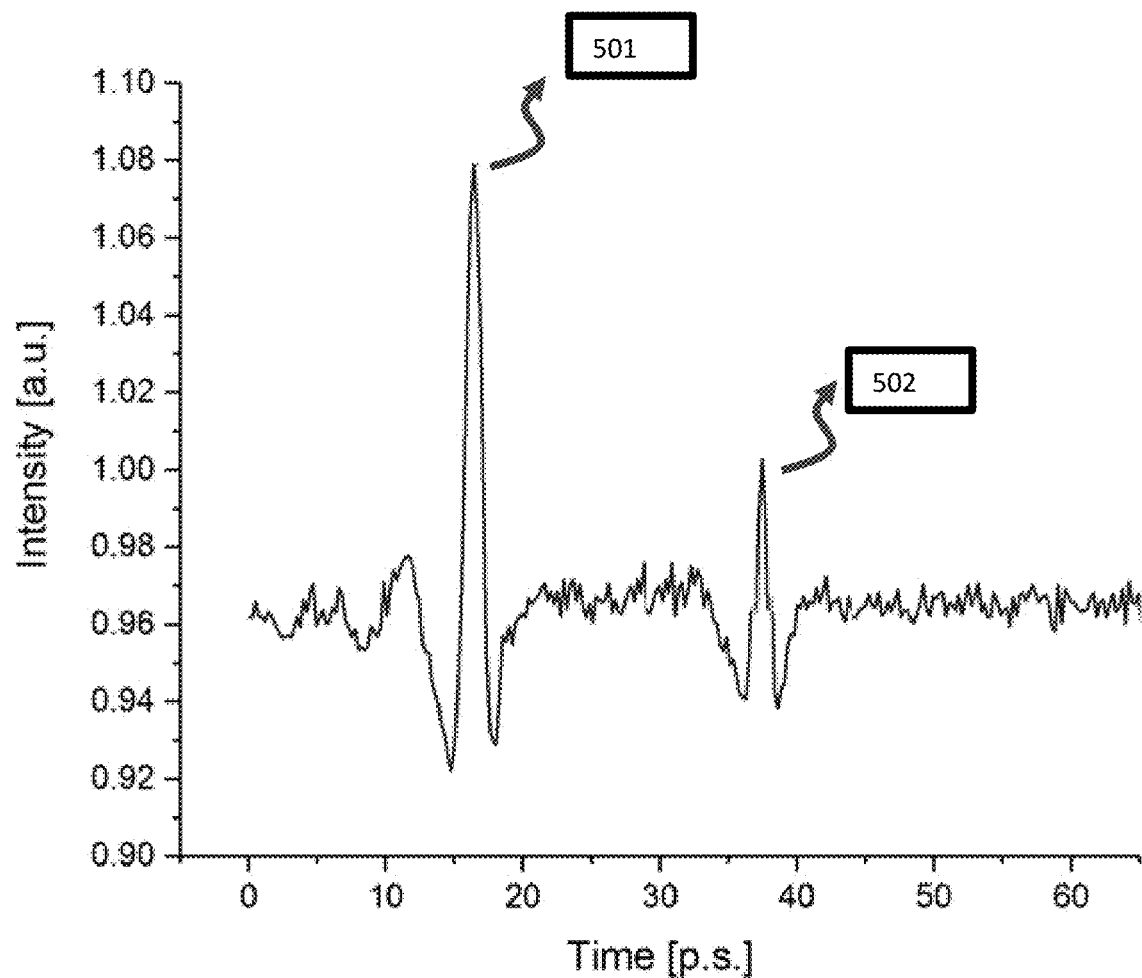
FIG. 5 illustrates the time-domain profile of the reflected THz beam where the THz beam encounters body fluids on the face of a mask wearer. Since absorption of THz beams in water is high, the second peak, 502, is suppressed drastically as compare to the second peak, 402, of FIG. 4.

FIG. 5 illustrates the time-domain profile of the reflected THz beam where the face of the person is contaminated with body fluids. Since Molecules of water have high absorption in THz frequency regime, the intensity of the part of the THz beam that is reflected from the face of the person that is contaminated with body fluids, 502, is suppressed as compared with 402. At the same time, since the mask is clean, the intensity of part of the beam that is reflected from the mask, 501, is identical to 401.

Figure 6:
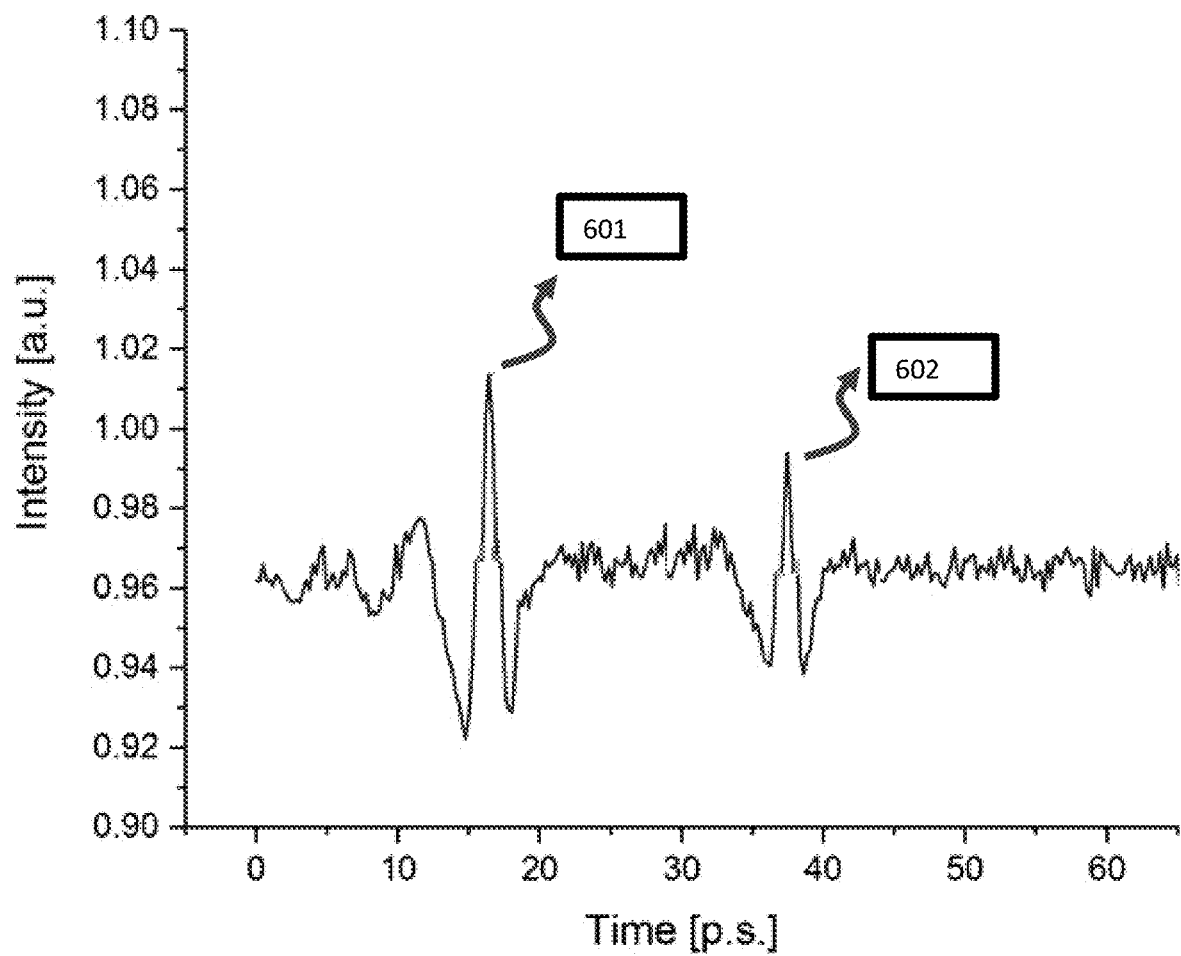
FIG. 6 illustrates the time-domain profile of the reflected THz beam where the beam encounters body fluids on the mask worn by a person. Since absorption of THz beams in water is high, both the first peak, 601, and the second peak, 602, are suppressed drastically as compare to the first peak, 401, and the second peak, 402, of FIG. 4.

FIG. 6 illustrates the spectrum of the reflected THz beam where the beam encounters fluids on the mask worn by a person. Where the mask is contaminated with body fluids, the first reflection, 601, has less intensity as compared to where the first reflection, 401, is reflected from a clean mask. This is due to the fact that molecules of water in body fluids on the mask absorb considerable portion of the THz beam. Since the part of the beam that passes through the contaminated mask goes through a higher absorption (FIG. 6) as compare to the part of the beam that passes through a clean mask (FIG. 4), the part of the beam that gets to the face of the person will have lower intensity. Hence, the second reflection, 602, which is reflected from the face of the person, will have lower intensity than 401. If the face of the person is also contaminated by body fluids, higher absorption will be observed in 602 than the case where only the mask is contaminated. Hence, by analyzing the profile of the reflected beam in time-domain it can be determined if: (a) the mask is clean or contaminated, (b) if the face of the person is clean or contaminated, (c) if both the face of the person and the mask are clean or contaminated.

For detecting traces of body fluids on the mask or face of the person, the device in FIG. 1 scans the face and the mask. The scanning may be done in only a line (1D direction) or an area may be scanned (2D or raster scanning). The scanning process may be done by the operator, or it may be done via electrical motors by moving the THz emitter, 205, and THz receiver, 206. FIG. 7 illustrates the intensity of the reflected THz beam (y-axis) on a 1D scanned dimension (x-axis). This graph is generated by mapping either of the first or second peaks, or combination of both, vs. the scanned direction. For the case of CW THz imaging systems, this graph is generated by mapping the intensity of the reflected THz beam on the scanned dimension. The lower intensity of the beam on 702 as compared with 701 and 703, is an indication of the existence of moisture on the face and/or the mask. The operator or a computer algorithm stored in a non-transitory computer-readable media that is executed by a microcontroller associated with the disclosed device, and method, may evaluate such profile. The computer algorithm may perform the evaluation by comparing the profile in FIG. 7 against the profile that would be obtained from a case where no contamination exists on the face or/and the mask of the person. If contamination is detected, the disclosed device may diagnose the person with symptoms of COVID-19 or other diseases such as flue. Since THz beams are invisible to the eye, a guiding laser light might be added to the disclosed device so that the operator knows where on the face or the mask is currently being scanned. If the scanning process is done in a 2D manner, THz image of the mask or the face can be developed by mapping the intensity of the first peak or the second peak respectively on a 2D image plane. If the scanning is done using CW-THz technology, both the mask and the face may be illustrated in one THz image.

Where contamination exists, the intensity of the THz image will differ from the clean areas. If the contamination is due to body fluids, since molecules of water have high absorption in THz frequency range, low intensity will be observed on the THz image. Such low intensity area is observed on the THz image of FIG. 8A and is indicated by 801. In FIG. 9, an area with low intensity is observed and is indicated by 901. The intensity of 901 is not as low as that of 801, which is an indication that the contamination associated with 901 does not contain water, or the amount (or thickness) of water in the contamination associated with 901 is less than that of 801. The operator may evaluate the THz image, or a computer algorithm stored in a non-transitory computer-readable media that is executed by a microcontroller associated with the disclosed device, and method, may process the images and detect traces of body fluids or contaminations in the images. Advanced algorithms based on machine learning may be integrated in the image processing algorithm for more accurate diagnosis. If contamination is detected, the disclosed device may diagnose the person with symptoms of COVID-19 or other diseases such as flue.

In a similar manner, ultrasound waves or infrared beams may be used for imaging the face and/or the mask of the person for detecting the traces of runny nose or coughing.

THz-TDS systems provide the time-domain profile of the THz beam. By techniques such as FFT, the time-domain of the signal may be converted to the frequency-domain. In frequency-domain, different materials show different characteristics in reaction with THz beams. Analyzing the frequency-domain of the THz beam reflected from a composite reveals information about ingredients of that composite. Hence, for more accurate analysis of the contaminations on the face or the mask of the person and detecting traces of contaminations or body fluids, this patent application discloses a method comprising scanning a location using THz beams, computing FFT of the reflected THz beams (in case the mask is only evaluated, transmitted THz beams, instead of reflected THz beams, may also be used) for converting the time-domain THz signals into frequency-domain signals, evaluating the frequency-domain signals for contaminations and body fluids. Inside the nose, mouth, and throat of the person may also be scanned and the frequency-domain of the reflected THz beams from these areas may be evaluated detecting contaminations, body fluids, congestion, or mucus. Sine THz beams pass through the mask, the person may or may not wear a face covering mask during the examination of the mouth, throat, and nose. FIG. 10 illustrates the frequency-domain of the intensity of the reflected THz beam from three different positions; the contaminated spot show different frequency profile, 1003, as compared with the profile of the measurement from clean spots, 1001 and 1002. The operator may evaluate the frequency-domain signals or a computer algorithm stored in a non-transitory computer-readable media that is executed by a microcontroller associated with the disclosed device may process the frequency-domain signals and detect traces of body fluids or contaminations in the frequency-domain signals. Advanced algorithms based on machine learning may be integrated in the algorithm for more accurate diagnosis. Once the evaluation is performed, the disclosed device, and method, may diagnose the person with symptoms of COVID-19 or other diseases such as flue.

FIG. 11 illustrates a flowchart of the disclosed method and system. The process starts by positioning the transmitter and receiver of THz beams in front of the face of a mask wearing person; this step is illustrated in 1101. Scanning may be performed in 1D or 2D manner. After positioning the transmitter and receiver of THz beams in front of the face of a mask wearing person, as 1102 illustrates, scanning a location on the face of a mask wearing person is executed by sending THz beam via THz emitter, 205, and receiving the reflection of the THz beam via THz receiver, 206. Scanning of the throat and the mouth of the person may be performed by asking the person to open their mouth and positioning the emitter and receiver of the THz beam in front of the mouth of the person and moving the emitter and receiver in a 1D or 2D manner. For scanning the inside of the nose of the person, the emitter and the received shall be positioned in front of the openings of the nose, or nostril. Since THz beams pass through the mask, the person may or may not wear a face covering mask during the examination of the face, mouth, throat, and nose. Wearing the mask helps the operator (healthcare workers) to stay safe since the mask shall cover the nose and the mouth of the person who is under examination. The process of receiving the reflected THz beam is illustrated in block 1103. The system may include analysis of frequency-domain of the THz beams. For converting the time-domain THz signal to a frequency-domain signal, FFT is computed in block 1104. As a result, the frequency-domain signal, or spectrum of the THz beam (what is illustrated in FIG. 10) is achieved. By analyzing the spectrum of the beam, type of contaminations in the mouth, nose, on the face or the mask is revealed. The analysis is done in block 1105. Block 1106 represents decision making process based on the result of analyzing the spectrum of the THz beam. This block determines if the mask or the face, or both, is clean, contaminated, or dirty with body-fluids. If the throat, mouth, or nose are scanned, this block determines the result of evaluations for these organs. Further, the materials in the contamination may be identified by comparing the spectrum of the reflected beam against a database where the profile of different materials is stored. Advanced algorithms such as machine learning may also be used to enhance the accuracy of the identification. Once the identification is executed, the results will be shown to the operator via a digital display and/or will be stored on a digital memory unit as illustrated in 1107.

If the THz emitter and receiver are not equipped with TDS technology (are not capable of recording the time-domain of THz beam, in other words they are operating in CW), the FFT block, 1104, will be bypassed. Such case is illustrated in FIG. 13. The intensity of the beam (similar to what is illustrated in FIG. 7 for 1D and in FIG. 8A and FIG. 9 for 2D scanning) will be analyzed for finding traces of contamination or body fluids on the face and the mask. Such analysis is done in block 1305.

The disclosed device and method may further comprise a resolution enhancement technology, according to the principle of U.S. Pat. No. 10,783,612 by the present inventor. The resolution enhancement technology provides enhanced-resolution THz imaging for detecting smaller traces of contamination on the mask and/or face (or in the mouth, nose, throat) of the person. The size of raindrops (in this case, traces of body-fluids as indications of cough and runny nose) is around 0.5 mm to 4 mm, with size distribution of sharply decreasing after 2-2.5 mm [20]. Whereas, the resolution of a THz imaging system with 0.25 THz frequency (wavelength of 1.2 mm), numerical aperture (NA) of 0.35, and K-factor of 1 is 3.4 mm. Hence, for thorough detection of drops of body-fluids, the resolution of the THz imaging system needs to be enhanced. FIG. 12A-B illustrates the disclosed device, and method, being equipped with the resolution enhancement technology, according to the principle of U.S. Pat. No. 10,783,612 by the present inventor whereby traces of 0.3 mm features in a packaged item has been identified using beams generated by THz-TDS.

Once the enhanced resolution THz image is developed in 1214, the image is either displayed to the operator for manual detection of traces of body fluids or contaminations on the mask and/or the face of the person, or is evaluated automatically by 1216 and 1217. The mouth, nose, throat may also be scanned and evaluated for mucus, congestion or runny nose. Further image reconstructions may be applied to the enhanced resolution THz image to reconstruct the shape of the trace of the body-fluids or contaminations on the enhanced resolution THz image. For example, FIG. 8C, illustrate enhanced-resolution THz image of FIG. 8A, whereon the waterdrop (which may be dropped or leaked from the nose of the person) is reconstructed on the image and marked with black color so that the operator can detect it on the image easier. The automated evaluation method may comprise of an image processing algorithm equipped with machine learning wherein the processed enhanced-resolution image is evaluated for detection of traces of contamination, runny nose or cough. The machine learning algorithm may have been trained with a large number of ground-truth images (training dataset) where traces of contamination, runny-nose or cough in the THz image of the mask or the face of the person are identified on the enhanced-resolution THz image. The machine learning algorithm compares the obtained enhanced-resolution THz image against the training dataset and determines if a feature observed in the enhanced resolution image is associated with traces of runny nose or cough. The result of the automated evaluation is displayed to the operator on a digital display and/or is stored on a digital memory illustrated in 1218.

FIG. 8B illustrate the enhanced-resolution version of the THz image in FIG. 8A whereon the trace of the drop of body fluid from nose on the skin of the face is clear. The tail of the waterdrop has less thickness as compared with the main body of the waterdrop. Hence, the tail absorbs less amount of THz beam. Thus, the tail of the waterdrop is associated with pixels with more intensity as compared with the main body of the waterdrop as illustrated in 802. FIG. 8C, illustrates enhanced-resolution THz image, whereon the waterdrop on the image is reconstructed and marked with black color so that the operator can detect it on the image easier.

The THz image of an object is developed by raster scanning the object and mapping the intensity of the traversed THz beam on a 2-dimensional image plane. The raster scanning process of the sample by the THz imaging beam is mathematically modeled as a two-dimensional convolution of the object function and the PSF, as expressed in Equation (1).

$$i(x,y) = PSF(x,y) * o(x,y) \qquad (1)$$

Where i is the image and o is the object function. The object function can be computed reversely from Equation (1) if the PSF is known.

$$o(x,y) = i(x,y) *^{-1} PSF(x,y) \qquad (2)$$

PSF can be measured directly. A pinhole is placed in front of the THz receiver to limit the added uncertainty due to the diameter of the receiver of the THz beam. Such measured PSF is shown in FIG. 14. Since the diameter of the pinhole cannot be zero and has to be large enough to pass through sufficient intensity of the beam for triggering the THz receiver, measured PSF will not be free of uncertainty. In addition, measuring the PSF inside the packaged object is impossible. In Equation (2) the PSF at a z-depth inside the sample where the layer that is being imaged is located is needed.

FIG. 15 illustrates the result of the deconvolution of the conventional THz image of a sample and the measured PSF. In FIG. 16 it is observed that the quality of the resulted image is even poorer than that of the conventional THz image (illustrated in FIG. 15) due to the mentioned uncertainties in the measured PSF. To avoid uncertainties that are added to the measured PSF due to the diameter of the pinhole, noise, and to have the PSF inside the packaged object, the mathematical equation for PSF has been developed and proposed to be used in Equation (2) by the present inventor [21]. FIG. 17 illustrates the modeled PSF and FIG. 18 illustrates the result of the deconvolution of the modeled PSF and the conventional THz image of Sample 2. It is observed in FIG. 18 that the quality of the resulted image is improved (the image is sharper and traces of the inside wires of the sample are observable) as compared with the conventional THz image (illustrated in FIG. 15).

What follows is the principle of developing the equation for PSF as developed and proposed by the present inventor [22] with some additional modifications. In order to describe the transmission imaging process, a three-dimensional mathematical function is needed where z-direction is also included. The inclusion of z is represented by integrating (1) over z.

$$i(x, y) = \int_{z_t}^{z_d} \int_{x'} \int_{y'} o(x-x', y-y', z_i) PSF(x', y', z_i) dx' dy' dz \qquad (3\text{-}a)$$

Where $z_t$ is the location of the THz transmitter and $z_d$ is the location of the THz detector on the z-axis.

In typical THz imaging systems, the center frequency and bandwidth are comparable. As a result, the beam cannot be treated as a monochromatic beam. For including the full spectrum, the PSF is reconstructed by the superposition of the monochromatic beams over the entire frequency band.

$$PSF = \int PSF(f) df \quad (3\text{-}b)$$

Jepsen and Keiding have shown that the output of PCA based THz-TDS systems include side-lobes. In this respect, THz focused PSF can be considered as a Bessel beam or an Airy disk [23]. In the same publication, Jepsen and Keiding have also proved that the main lobe in the output of such systems has a Gaussian profile. In addition, according to Sagan, when the truncation ratio (the ratio of the diameter of the Gaussian beam to the diameter of the truncating aperture) is set to 1, the sidelobes become negligible and the beam profile becomes purely Gaussian [24].

The source of the beam is a circular aperture lens-coupled antenna which output is approximated by Gaussian illumination distribution [25]. This illumination distribution remains Gaussian after exiting the circular aperture and cylindrical lenses of the imaging system [26]. PSFs with smaller diameters can be achieved by increasing the truncation ratio, W. However, the side lobes of the PSF grow larger as W increases. Side lobes contribute to the degradation of the resolution [24]. The fraction of the intensity of the central lobe is reported to be more than 95% of the total beam power where W=1 [27]. Thus, apertures in most of the imaging systems, including the experimental system which is used in this work, are chosen accordingly to achieve W≈z1. As a result, the PSF of the typical THz imaging systems can be approximated by a $TEM_{00}$ mode Gaussian beam.

The spot size diameter of the Gaussian beam is defined to be where the intensity drops to $1/e^2$ of the peak value of the beam intensity. The radius of the spot at distance z from the beam waist is given by (4) [28].

$$w(z, f) = w(0, f) \sqrt{1 + \left(\frac{\lambda z}{\pi w^2(0, f)}\right)^2} \quad (4)$$

Where w(0,f) is the spot radius at the beam waist and f is the frequency of the beam. As mentioned, the THz beam spreads over the frequency band of a few THz and thus the center frequency of the beam is comparable to its bandwidth. Consequently, the bandwidth of the beam has to be incorporated as a variable into the PSF equation. In this respect, the intensity profile of the THz beam is represented by the Gaussian distribution in (5).

$$I(\rho, z, f) = I_0 \exp(-2\rho^2/w(z,f)^2) \quad (5)$$

Where $O_0 = I(0,z,f)$ is the intensity at the center of the beam and ρ is the radial position from the center of the beam on the corresponding z-plane at a distance z from the beam waist.

$$\rho^2 = x^2 + y^2 \quad (6)$$

The full width at half maximum (FWHM) for Gaussian distribution in (5) is given by:

$$FWHM(z,f) = \sqrt{2\ln 2}\, w(z,f) \quad (7)$$

On the other hand, FWHM of diffraction-limited focused spot is given by:

$$FWHM(0, f) = 1.13 k\lambda F\# = 0.565 \frac{k}{NA} \frac{c}{f} \quad (8)$$

Where k-factor depends on the truncation ratio and level of the irradiance, F# is the ratio of the focal length and the diameter of the focusing lens, and NA is the numerical-aperture [24]. Substituting (8) into (7) yields the relation of the beam waist and the physical parameters of the system:

$$w(0, f) = \frac{FWHM(0, f)}{\sqrt{2\ln 2}} = \frac{0.565}{\sqrt{2\ln 2}} \frac{k}{NA} \frac{c}{f} \quad (9)$$

Now, substituting (9) into (4) gives the relation between w(z,f) and the physical parameters of the system:

$$w(z, f) = \frac{0.565}{\sqrt{2\ln 2}} \frac{k}{NA} \frac{c}{f} \sqrt{1 + \left(\frac{2\ln 2}{c\pi}\left(\frac{NA}{0.565k}\right)^2 fz\right)^2} \quad (10)$$

Substituting (10) into (5), yields the mathematical model of the beam profile.

$$I(\rho, z_{df}, f) = \quad (11)$$

$$I_0 \exp\left(-2\rho^2 \Bigg/ \left(\frac{0.565}{\sqrt{2\ln 2}} \frac{k}{NA} \frac{c}{f} \sqrt{1 + \left(\frac{2\ln 2}{c\pi}\left(\frac{NA}{0.565k}\right)^2 fz_{df}\right)^2}\right)^2\right)$$

To avoid confusion between the depth of the layer inside the sample and the distance from the beam waist (or defocus), we indicated the distance from the beam waist in (11), and following equations by $z_{df}$ or $z_{defocus}$. The attenuation of the beam in the object is frequency-dependent. Since the imaging beam is not monochromatic, the frequency-dependency of the attenuation needs to be taken into account. Assuming that the measurement is done in a vacuum environment, the attenuation factor of the sample can be calculated by using Equation (12).

$$\alpha_{sample}(f) = -\frac{1}{z_{thickness}} \ln \frac{I_{sample}(\rho, z_{detector}, f)}{I_{ref}(\rho, z_{detector}, f)} \quad (12)$$

Where $I_{ref}(\rho, z_{detector}, f)$ is the intensity of the reference beam at the THz detector plane, without the, presence of the sample in the THz imaging system, $I_{sample}(\rho, z_{detector}, f)$ is the intensity of the beam at the THz detector plane with the presence of the sample in the THz imaging system, and $z_{thickness}$ is the thickness of the sample. Since the attenuation factor can be obtained by using (12), the intensity of the beam at any depth $z_{ds}$ inside the sample can be obtained by substituting the attenuation factor into (13) assuming that the measurement is done in a vacuum environment.

$$I(\rho, z_{ds}, f) = e^{-z_{ds}\alpha(f)} I_{ref}(\rho, z_{detector}, f) \quad (13)$$

Substituting (13) into (11) yields:

$$I(\rho, z, f) = I_{ref}(0, z_{detector}, f) \exp\Bigg(-z_{ds}\alpha(f) - \quad (14)$$

$$2\rho^2 \Bigg/ \left(\frac{0.565}{\sqrt{2\ln 2}} \frac{k}{NA} \frac{c}{f} \sqrt{1 + \left(\frac{2\ln 2}{c\pi}\left(\frac{NA}{0.565k}\right)^2 fz_{df}\right)^2}\right)^2\Bigg)$$

The digitalized version of integral over the spectrum in (3) can be implemented by (15).

$$PSF(z, f) = \sum_f I_{ref}(0, z_{detector}, f)$$

$$\exp\left(-z_k b\alpha(f) - p^2/2\left(0.44\frac{ka}{NA}\frac{c}{f}\sqrt{1+\left(\frac{147}{c\pi}\left(\frac{NA}{k}\right)^2 fz_{df}\right)^2}\right)^2\right)$$ (15)

Where a and b are the adjustment factors. The inclusion of z is necessary since THz images are developed via the transmission of the imaging beam through the sample. Samples could be thick and as a result, not all the layers happen to be on the focal plane. For the same reason and the fact that beams with higher frequencies go through higher attenuations inside the sample, not all the layers are imaged via imaging beams with identical spectrums. Accordingly, $z_{ds}$ and $z_{df}$ in (15) accommodate attenuation and divergence of the beam in the sample respectively. Finally, substituting (15) into (1) yields the THz imaging equation which can be used for simulating the THz images.

$$i(x, y) = \sum_f I_{ref}(0, z_{detector}, f)\exp\left(-z_{ds} b\alpha(f) - \right.$$

$$\left. \rho^2/2\left(0.44\frac{ka}{NA}\frac{c}{f}\sqrt{1+\left(\frac{1.47}{c\pi}\left(\frac{NA}{k}\right)^2 fz_{df}\right)^2}\right)^2\right) * o(x, y, z)$$ (16)

Equation (16) can be further completed to include refraction effects (as the refractive index of the sample and ambient air or vacuum are different), aberration, scattering of the beam at edges and etc. This PSF equation can also be further modified, simplified, and prepared to be implemented by digital computers. In case the reflection images are being developed, the angle of the incident beam needs to be included in (16) as well. Accordingly, PSF is developed in block 1208. As an additional advantage, the PSF can be used for developing a simulated terahertz image. By substituting the PSF from equation (16) and the object function, which can be an X-ray image of the package sample, the simulated THz image of the packaged item will be achieved. In the prior art the maximum of the THz pulse or the range of it (the difference between the maximum and minimum) have been used for developing the intensity of the pixel as indicated in Equation (17):

Intensity of Pixel at coordinate $(i,j)$=(maximum of
THz pulse at $(i,j)$)−(minimum of THz pulse at
$(i,j)$) (17)

Diffracted beams are diverged, they need to travel through a longer distance, and hence they need more time to arrive at the detector plane. As a result, we can expect that filtering out the beams with higher time delays will result in an image with less diffraction distortion. Accordingly, this disclosure reveals that using the magnitude of the THz pulse at a time-delay before the maximum of the THz pulse leads to a better resolution. As FIG. 19 illustrates the minimum of the THz pulse has a higher time delay than the maximum of the THz pulse. In other words, the amount of diffraction in beams that are forming the minimum of the THz pulse is higher than the amount of the diffraction in beams that are forming the pulse where the time-delay is lower than that of the minimum point. Consequently, we can expect to achieve an image with less diffraction distortion if the magnitude of the THz pulse at a point with less time delay than that of the minimum of the pulse is used to develop the THz image. In Equation (18) instead of the minimum of the THz pulse, the magnitude of the THz pulse at a point before (with less time-delay than) the maximum of the THz pulse is used:

Intensity of Pixel at coordinate $(i,j)$=(maximum of
THz pulse at $(i,j)$)−(amplitude of THz pulse at a
time-advance before that of the maximum of
the THz pulse at $(i,j)$) (18)

Equation (18) is used in block 1210 for developing the intensity of the pixels in the disclosed system of this invention. FIG. 20C. and FIG. 20D. are developed by using Equation (18) in block 1210, these two images show less blur and artifacts compared with their counterparts shown respectively in FIG. 20B. and FIG. 20F. developed by the conventional method represented in Equation (17). The timed-advance in Equation (18) can be found numerically by starting from an estimated value until the sharpest image is achieved. In addition, rigorous calculations can be performed to compute the time-advance according to equations of diffraction as proposed and demonstrated by the present inventor [29]. For example, such calculations is performed here for Sample 2. The dimension of the main lobe of the diffraction pattern can be approximated as:

$$W_x(0, 0) = \frac{\lambda d}{D_x}$$ (19-a)

$$W_y(0, 0) = \frac{\lambda d}{D_y}$$ (19-b)

The difference between the distances that the beam needs to travel to the center of the main lobe and the side of the main lobe on y-axis can be calculated as:

$$\Delta d_y = \sqrt{d_{cl}^2 + W_y^2} - d_{cl}$$ (20)

In (20), $d_{cl}$ is the distance between the sample and the focusing/collimating lens along with the z-axis.

Sample 2 is a 28 mm by 14 mm, 44 pins packaged IC. The separation between the pins of the IC can be measured by a Vernier caliper as $D_x$=0.7 mm the length of these separations inside the packaging can also be approximated as $D_y$=7 mm. For Sample2 dimensions in (19a) and (19b) are calculated to be $W_x$=15.42 mm and $W_y$=1.54 mm. Thus, the smallest time difference between the time-delay for the beam to get to the edge of the main lobe at $W_y$ with reference to the time-delay that the beam needs to travel directly on the center of the main lobe is calculated to be $t_d$=0.7 ps. In other words, filtering the beams with delays of $t_d$ and higher (not using them for developing the image), will result in an image with less diffraction distortion. Accordingly, Equation (21) can be used in block 1210.

$$I(i,j)=s(t-td)\ (i,j)-s(t_{floor})(i,j)$$ (21)

Equation (21) can be read as:

Intensity of Pixel at coordinate $(i,j)$=(magnitude of
THz pulse at $(i,j)$) with a time-advance of $t_d$
with respect to the time delay of the maximum
of the THz pulse at $(i,j)$)−(amplitude of THz
pulse at its floor at $(i,j)$) (22)

Figure 21:
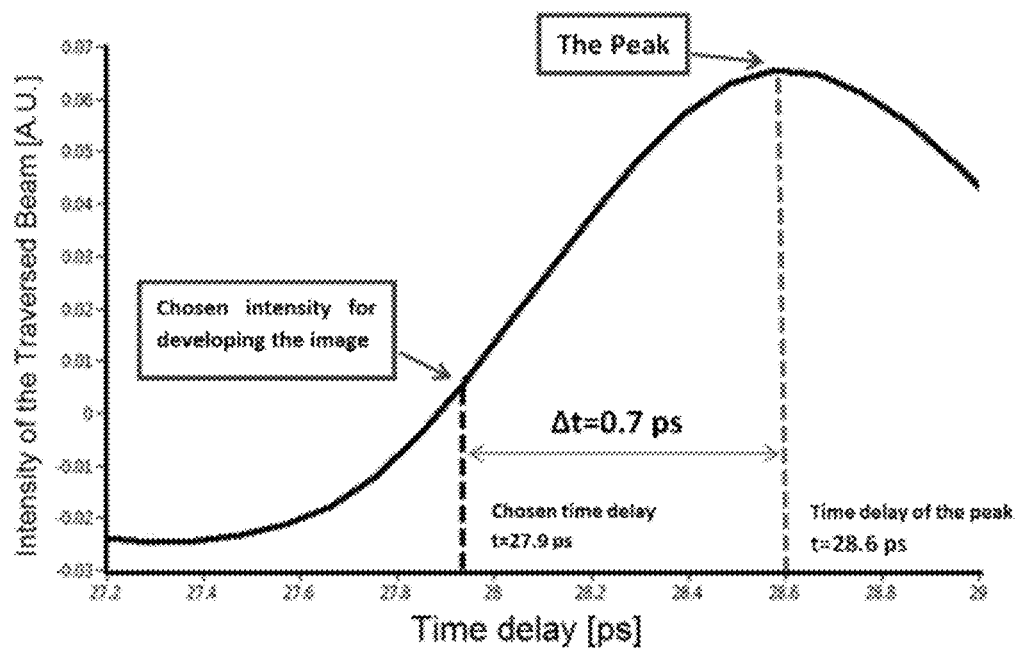
Figure 21:
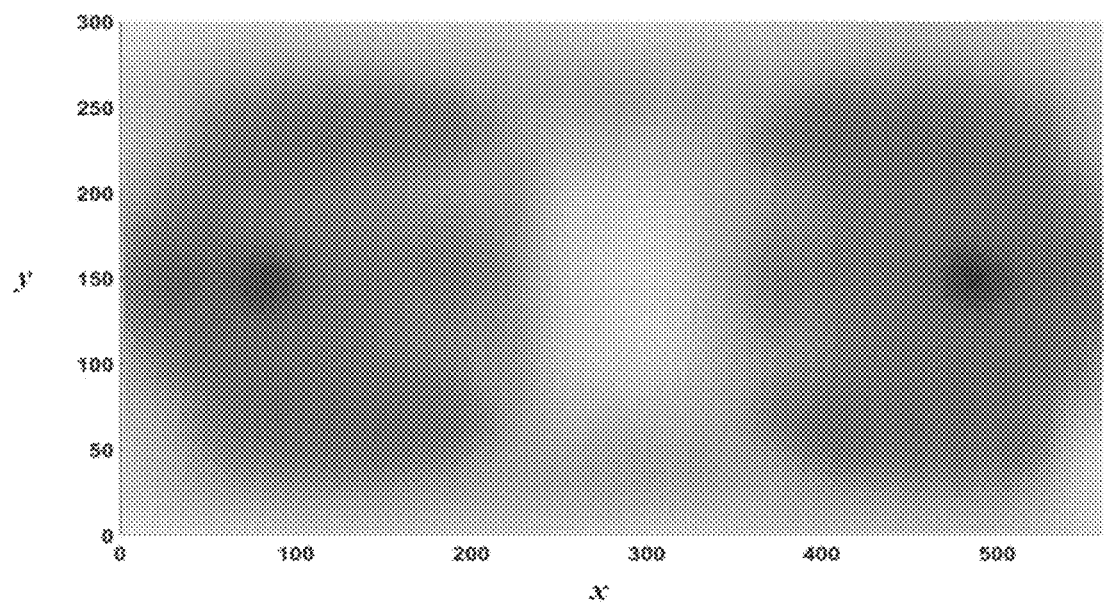

FIG. 21. A. illustrate the magnitude of the terahertz pulse at a time-advance of 0.7 ps before the maximum of the terahertz pulse. This magnitude is used in Equation (21) for developing the THz image. FIG. 21. B. illustrates the resulted THz image developed by means of Equation (21). This image is sharper than its counterpart developed by means of Equation (17) illustrated in FIG. 15. Traces of the inside wires can be observed on the image of FIG. 21. B. while traces of the inside wires are not observable on the image of FIG. 5B.

Diffraction increases as the frequency of the beam decreases. The low-frequency of the THz signal is filtered-out in 1205 to lower the blurring effect of diffraction. High-frequency noise is also filtered out in 1205.

The output signal of 1205 is given to 1209 where it is converted back to time-domain by inverse FFT. In case that the BPF in 1205 is bypassed by setting its low and high cut-off frequencies to respectively 0 and infinity, the deconvolution (performed in 1214) of the modeled PSF (developed in 1206) and THz image (developed in 1211) will result in the image illustrated in FIG. 20E. where time-domain diffraction suppression filter (Equation (18)) in 1210 has also been activated. 1211 maps and stores the pixels of the image until the sample is entirely processed. 1212 determines if the process of the sample is completed and all the pixels of the image are developed in 1211. If yes, 1215 computes the deconvolution of the image and the PSF. 1215 sends the resulted enhanced-resolution image to the display and/or the memory units. The final enhanced-resolution image is shown in FIG. 20D. for Sample 1, FIG. 22G. for Sample 2, and FIG. 23D. for Sample 3. As shown in FIG. 22J. and FIG. 22G. features as small as 300 µm, and features with separations of 550 µm are observable in the resulted enhanced-resolution image. The size and locations of the features are confirmed by overlaying the resulted enhanced-resolution THz images on the high-resolution X-ray images. In FIG. 20G. and FIG. 22F. X-ray images of Sample 1 and Sample 2 are illustrated respectively. In FIG. 20H. and FIG. 22E the enhanced-resolution images and X-ray images of Sample 1 and Sample 2 are overlayed to prove the accuracy of the results. In FIG. 22J. the 300 µm feature which is observed in the enhanced-resolution THz image is shown. In FIG. 22I. the x-Ray image of the same feature is shown to prove the accuracy of the results. In FIG. 22K. the conventional THz image is shown; the resolution of the conventional THz image is not sufficient to observe the feature.

Since in Continuous-Wave (CW) THz imaging systems the THz imaging beam is not recorded as a time-domain signal, the system of FIG. 12A needs to be reduced to the system of FIG. 12B to process the THz images captured by CW THz imaging systems. In FIG. 12B, block 12001 (which is equivalent of 1206 in FIG. 12. A) provides an estimation of the spectrum of the THz imaging beams to block 1208. Block 1207 provides Optical, System and Sample Parameters to block 1208. In block 1208 the PSF of the THz beam is modeled (or estimated). 12004 is providing the THz image or Video captured by a Continuous-Wave (CW) THz imaging system. In 1208 said PSF is deconvolved to the THz image captured by a CW THz imaging system. 1215 is a memory and/or display wherein the resulted enhanced-resolution THz image is stored and/or displayed. The dashed line between 1215 and 1208 is an optional feedback line providing feedback to the PSF modeler for adjusting the PSF until the sharpest image is achieved. A similar feedback line can be included in the system of FIG. 12A as well.

Figure 24:
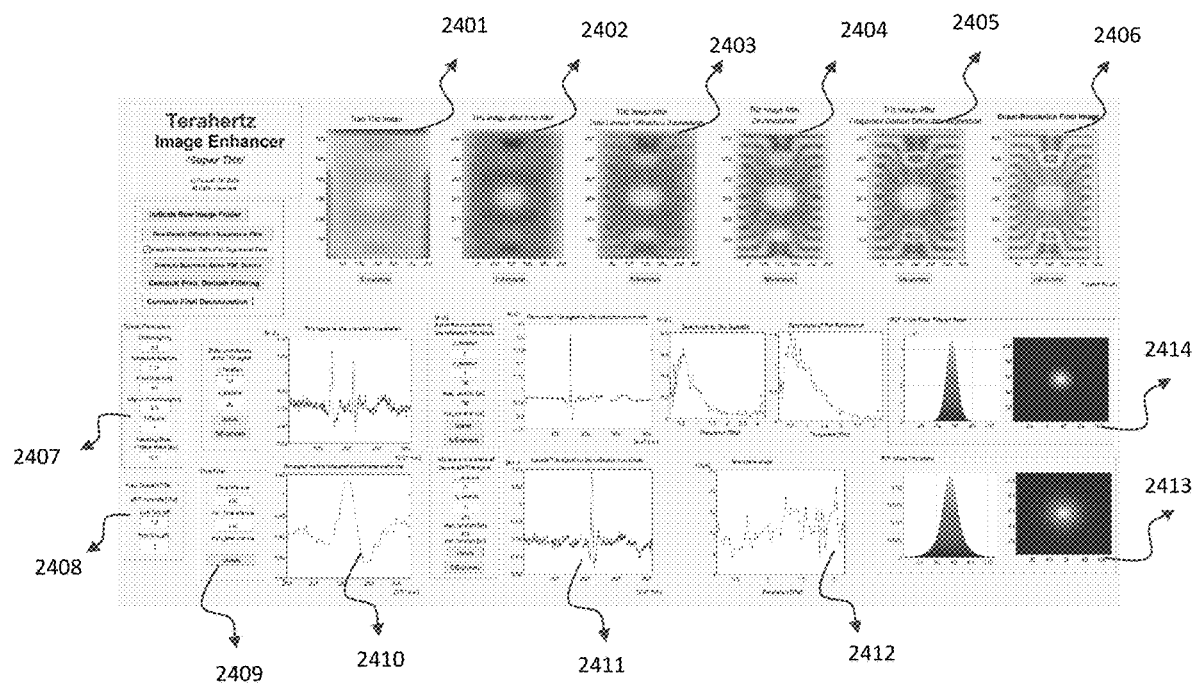
Figure 24:
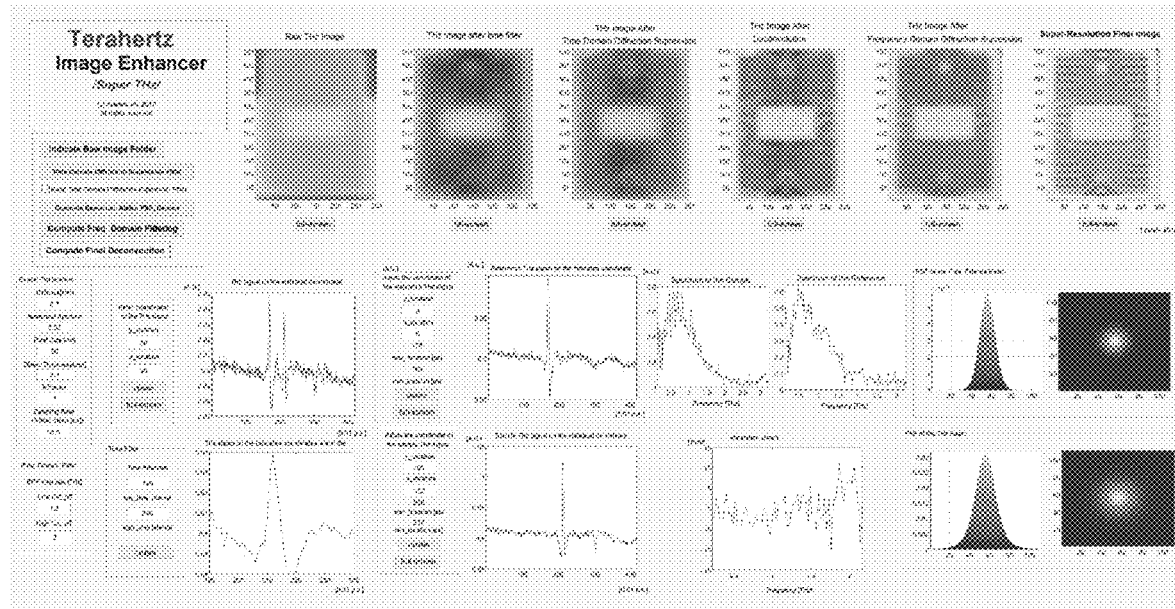
Figure 24:
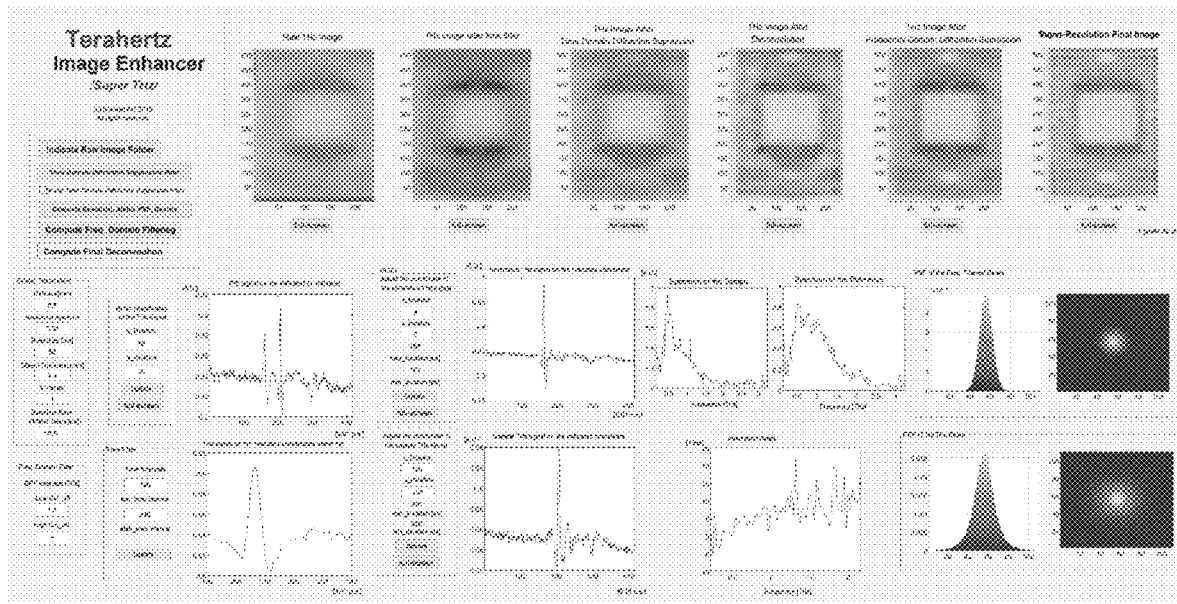

The disclosed systems and processes of FIGS. 2, 11, 12A, 12B, 13 may be implemented by computer programs and standalone specifically designed circuitry with digital microcontrollers, digital signal processors (DSP), and analog circuit components to perform the process and computations. The process may be stored in a non-transitory computer-readable media that is executed by a microcontroller. FIG. 24. A, B, C illustrate a Graphical User Interface (GUI) prototype of the resolution-enhancement system of FIG. 12A. implemented by digital computers processing images of Samples 1, 2, and 3 respectively.

No measurement in this patent applications has been performed on a live specimen, namely a person or an animal. Images and graphs in FIGS. 3-10 are artificially developed for sake of demonstration of the concepts disclosed in this patent application.

While the above description contains many specifications, these should not be construed as limitations on the scope of any embodiment, but as exemplification of the presently preferred embodiments thereof. Many other ramifications and variations are possible within the teachings of the various embodiments. For example, as a demonstration of the feasibility of the invention, the process is performed and the results are shown for three samples as examples and for THz systems. Thus, the scope of the invention should be determined by the appended claims and their legal equivalents and not by the examples given.

Conclusion

In this disclosure, a novel method and device for detection of the symptoms of COVID-19, namely runny nose, mucus and congestion, and cough, in the nose, throat and mouth, and on the face and mask of a mask wearing person without needing the person to take off the mask using beams in the frequency range of THz has been disclosed. Further a resolution enhancement method and system for enhancing the resolution of THz imaging systems for improving the diagnosis of the symptoms has been disclosed. The PSF of the imaging beam has been modeled by incorporating the spectrum of the imaging beam and the absorption coefficient of the object, or equivalently, the spectrum of the beam that has passed through the object (or the beam that has been reflected from the object in case of the reflection mode imaging), into a Gaussian beams distribution. The frequency-domain and time-domain filtering of the beam has also been incorporated as building blocks into the system. The deconvolution of the image and the modeled PSF has been computed. A novel method and system has also disclosed for simulation of THz imaging systems wherein the PSF is modeled and convolution of the modeled PSF and the object function is computed, the output of this system is a simulated THz image.

CITATION LIST

[1] "The COVID-19 pandemic triggers billions in new spending for public health imaging technology." [Online]. Available: https://www.cnbc.com/advertorial/2020/09/23/the-covid-19-pandemic-triggers-billions-in-new-spending-for-public-health-imaging-technology.html. [Accessed: 28Sep. 2020].

[2] "Symptoms of Coronavirus|CDC." [Online]. Available: https://www.cdc.gov/coronavirus/2019-ncov/symptoms-testing/symptoms.html. [Accessed: 28Sep. 2020].

[3] "Trump's physician says he is fever-free and not currently on oxygen—CBS News." [Online]. Available: https://www.cbsnews.com/news/trump-covid-19-update-physician-says-president-is-fever-free-and-not-on-oxygen-2020-10-03. [Accessed: 06Oct. 2020].

[4] S. Hunsche, M. Koch, I. Brener, and M. Nuss, "THz near-field imaging," *Opt. Commun.*, vol. 150, no. 1-6, pp. 22-26, May 1998.

[5] F. Blanchard, A. Doi, T. Tanaka, and K. Tanaka, "Real-Time, Subwavelength Terahertz Imaging," *Annu. Rev. Mater. Res.*, vol. 43, no. 1, pp. 237-259, July 2013.

[6] V. A. Trofimov, V. V. Trofimov, and I. E. Kuchik, "Resolution enhancing of commercially available passive THz cameras due to computer processing," 2014, p. 91990P.

[7] V. A. Trofimov and V. V. Trofimov, "New algorithm for the passive THz image quality enhancement," 2016, p. 98560M.

[8] C. Schildknecht, T. Kleine-Ostmann, P. Knobloch, E. Rehberg, and M. Koch, "Numerical image enhancement for THz time-domain spectroscopy," in *THz 2002-2002 IEEE 10th International Conference on Terahertz Electronics, Proceedings*, 2002, vol. 1, no. 1, pp. 157-160.

[9] B. B. Hu and M. C. Nuss, "Imaging with terahertz waves," *Opt. Lett.*, vol. 20, no. 16, p. 1716, August 1995.

[10] N. M. Burford and M. O. El-Shenawee, "Enhancement of terahertz imaging of packaged power electronic devices," in *2015 IEEE International Symposium on Antennas and Propagation & USNC/URSI National Radio Science Meeting*, 2015, vol. 2015-October, pp. 1300-1301.

[11] Z. Zhang, Y. Zhang, G. Zhao, and C. Zhang, "Terahertz time-domain spectroscopy for explosive imaging," *Opt.-Int. J. Light Electron Opt.*, vol. 118, no. 7, pp. 325-329, July 2007.

[12] "Terahertz Time Domain Solutions|Menlo Systems.".

[13] "THz Bandpass Filters: 10 µm-590 µm Center Wavelength.".

[14] "THz lenses.".

[15] N. V. Chernomyrdin et al., "Wide-aperture aspherical lens for high-resolution terahertz imaging," *Rev. Sci. Instrum.*, vol. 88, no. 1, p. 014703, 2017.

[16] N. V. Chernomyrdin et al., "Solid immersion terahertz imaging with sub-wavelength resolution," *Appl. Phys. Lett.*, vol. 110, no. 22, p. 221109, 2017.

[17] M. S. Kulya, N. S. Balbekin, I. V. Gredyuhina, M. V. Uspenskaya, A. P. Nechiporenko, and N. V. Petrov, "Computational terahertz imaging with dispersive objects," *J. Mod. Opt.*, vol. 64, no. 13, pp. 1283-1288, July 2017.

[18] K. Ahi, N. Jessurun, M.-P. Hosseini, and N. Asadizanjani, "Survey of terahertz photonics and biophotonics," *Opt. Eng.*, vol. 59, no. 06, p. 1, May 2020.

[19] W. L. Chan, J. Deibel, and D. M. Mittleman, "Imaging with terahertz radiation," *Reports on Progress in Physics*, vol. 70, no. 8. pp. 1325-1379, 2007.

[20] G. M. McFarquhar, "Raindrop size distribution and evolution," in *Rainfall: State of the Science*, Wiley Blackwell, 2010, pp. 49-60.

[21] K. Ahi, S. Shahbazmohamadi, and N. Asadizanjani, "Quality control and authentication of packaged integrated circuits using enhanced-spatial-resolution terahertz time-domain spectroscopy and imaging," *Opt. Lasers Eng.*, vol. 104, pp. 274-284, May 2018.

[22] K. Ahi, "Developing next generation of electric grids for fulfilling deficiencies of conventional grids in supporting today's requirements," in *International Conference on Power Engineering, Energy and Electrical Drives*, 2011.

[23] P. U. Jepsen and S. R. Keiding, "Radiation patterns from lens-coupled terahertz antennas.," *Opt. Lett.*, vol. 20, no. 8, pp. 807-809, 1995.

[24] S. Sagan, "Optical Systems for Laser Scanners," in *Handbook of Optical and Laser Scanning, Second Edition*, CRC Press, 2011, pp. 69-132.

[25] E. R. Brown, "Fundamentals of Terrestrial Millimeter-Wave and THz Remote Sensing," *Int. J. High Speed Electron. Syst.*, vol. 13, no. 04, pp. 995-1097, 2003.

[26] B. E. A. Saleh and M. C. Teich, "Fundamentals of Photonics , 2nd Edition," *Wiley*. p. 1200, 2007.

[27] H. T. Yura and T. S. Rose, "Gaussian beam transfer through hard-aperture optics.," *Appl. Opt.*, vol. 34, no. 30, pp. 6826-6828, 1995.

[28] S. Fathololoumi et al., "Beam Pattern Investigation of Terahertz Quantum Cascade Lasers," *PIERS Online*, vol. 4, no. 2, pp. 267-270, 2008.

[29] K. Ahi, "A method and system for enhancing the resolution of terahertz imaging," *Meas. J. Int. Meas. Confed.*, vol. 138, pp. 614-619, May 2019.

The invention claimed is:

1. A method for improving resolution of terahertz imaging of a sample, comprising:
(a) using terahertz time-domain signals acquired by a terahertz time-domain spectroscopy system for acquiring a terahertz image,
(b) using a computer comprising a memory and a central processing unit for storing data and performing time-domain and frequency-domain processes on said time-domain terahertz signals,
(c) converting said time-domain terahertz signals to frequency-domain signals,
(d) processing said frequency-domain signals by means of a frequency-domain filter or a plurality of frequency-domain filters to achieve processed frequency-domain signals,
(e) converting said processed frequency-domain signals back to time-domain to achieve processed time-domain signals,
(f) developing a terahertz image using said processed time-domain signals,
(g) developing an enhanced-resolution terahertz image by computing deconvolution of said terahertz image and a point spread function,
(h) displaying or storing, or displaying and storing, said enhanced-resolution terahertz image,
(i) evaluating said enhanced-resolution terahertz image by determining if traces of symptoms of COVID-19 are present, wherein determining traces of symptoms for COVID-19 includes determining if there are traces of a runny nose, congestion, mucus, or cough.

2. The method of claim 1, further comprising using a time-domain filter for suppressing diffraction wherein for developing said terahertz image intensity of said processed time-domain signals at a time delay smaller than the time delay of the peak value of said terahertz time-domain signals is used.

3. The method of claim 1, wherein said point spread function is modeled by means of a mathematical equation.

4. The method of claim 3, wherein at least one optical parameter, or estimation of at least one optical parameter, of the imaging system of said terahertz time-domain spectroscopy system is used as an input for said mathematical equation for developing said point spread function.

5. The method of claim 4, wherein at least one parameter, or estimation of at least one parameter, of said terahertz time-domain spectroscopy system, such as the spectrum of the terahertz pulse of said terahertz time-domain spectroscopy system, is used as an input for said mathematical equation for developing said point spread function.

6. The method of claim 5, wherein said estimated point spread function is tuned iteratively until said enhanced-resolution terahertz image is achieved.

7. The method of claim 1, wherein the evaluating said enhanced-resolution terahertz image for finding traces of symptoms of COVID-19 such as traces of runny nose, congestion, mucus, or cough is performed by detecting traces of body-fluids on said enhanced-resolution terahertz image.

8. The method of claim 1, wherein the evaluating said enhanced-resolution terahertz image is performed according to principles of image processing and is executed by a digital microcontroller.

9. The method of claim 8, wherein said enhanced-resolution terahertz image is evaluated using a machine learning method.

10. The method of claim 1, wherein said sample is part of clothing, accessories, or an organ of a person.

11. The method of claim 10, wherein said person is wearing a face covering mask.

12. A method for diagnosing symptoms of COVID-19 comprising:
   (a) using a THz emitter to send an electromagnetic beam in the frequency range of THz,
   (b) using a THz receiver to receive the reflection of said electromagnetic beam in the frequency range of THz,
   (c) scanning a person using said electromagnetic beam in the frequency range of THz by positioning said THz emitter in front of said person, emitting said electromagnetic beam in the frequency range of THz on said person, positioning said THz receiver in front of the path of the reflection of said electromagnetic beam in the frequency range of THz, receiving said reflection of said electromagnetic beam in the frequency range of THz by said THz receiver,
   (d) evaluating reflection of said electromagnetic beam in the frequency range of THz received by said THz receiver by determining if traces of symptoms of COVID-19 are present, wherein determining traces of symptoms for COVID-19 includes determining if there are traces of a runny nose, congestion, mucus, or cough.

13. The method of claim 12, wherein said evaluating reflection of said electromagnetic beam in the frequency range of THz received by said THz receiver comprises converting the time-domain signal of said beam to a frequency-domain signal and analyzing said frequency-domain signal for finding traces of contamination or body fluid.

14. The method of claim 12, wherein said evaluating reflection of said electromagnetic beam in the frequency range of THz received by said THz receiver comprises comparing intensity of reflection of said electromagnetic beam in the frequency range of THz received by said THz receiver against expected intensity of a clean spot for finding traces of contamination or body fluids.

15. The method of claim 12, wherein said scanning is executed in a 2-dimensional manner and said evaluating reflection of said electromagnetic beam in the frequency range of THz received by said THz receiver comprises developing a THz image by mapping the intensity of reflection of said electromagnetic beam in the frequency range of THz received by said THz receiver and detecting traces of symptoms of COVID-19 in said THz image.

16. The method of claim 12, wherein said evaluating reflection of said electromagnetic beam in the frequency range of THz received by said THz receiver comprises a machine learning method, executed by a digital computer, for finding traces of symptoms of COVID-19 in data obtained from said electromagnetic beam in the frequency range of THz received by said THz receiver.

17. A device for diagnosing symptoms of COVID-19 comprising:
   (a) a THz emitter to send an electromagnetic beam in the frequency range of THz,
   (b) a THz receiver to receive the reflection of said electromagnetic beam in the frequency range of THz,
   (c) a computer comprising a memory and a central processing unit for storing data and performing processes on said reflection of said electromagnetic beam in the frequency range of THz,
   whereby for finding traces of symptoms of COVID-19 a person is scanned by said electromagnetic beam in the frequency range of THz emitted by said THz emitter, such that said reflection of said electromagnetic beam in the frequency range of THz is received by said THz receiver, and is stored in said memory, so that said central processing unit performs evaluating reflection of said electromagnetic beam in the frequency range of THz received by said THz receiver by determining if traces of symptoms of COVID-19 are present, wherein determining traces of symptoms for COVID-19 includes determining if there are traces of a runny nose, congestion, mucus, or cough.

18. The device of claim 17, wherein said evaluating reflection of said electromagnetic beam in the frequency range of THz received by said THz receiver comprises converting the time-domain signal of said beam to a frequency-domain signal and analyzing said frequency-domain signal for finding traces of contamination or body fluid.

19. The device of claim 17, wherein said scanning is executed in a 2-dimensional manner and said evaluating reflection of said electromagnetic beam in the frequency range of THz received by said THz receiver comprises developing a THz image by mapping the intensity of said reflection of said electromagnetic beam in the frequency range of THz received by said THz receiver and detecting traces of symptoms of COVID-19 in said THz image.

20. A method for improving the resolution of terahertz imaging of a sample, comprising:
   (a) using terahertz data acquired by a continuous-wave terahertz imaging system for acquiring a terahertz image,
   (b) using a computer comprising a memory and a central processing unit for storing data and performing processes on said terahertz data,
   (c) developing a terahertz image using said terahertz data,
   (d) developing an enhanced-resolution terahertz image by computing deconvolution of said terahertz image and a point spread function,
   (e) displaying or storing, or displaying and storing, said enhanced-resolution terahertz image,
   (f) evaluating said enhanced-resolution terahertz image by determining if traces of symptoms of COVID-19 are present, wherein determining traces of symptoms for COVID-19 includes determining if there are traces of a runny nose, congestion, mucus, or cough.

21. The method of claim 20, wherein said point spread function is modeled by means of a mathematical equation.

22. The method of claim 21, wherein at least one optical parameter, or estimation of at least one optical parameter, of the imaging system of said continuous-wave terahertz imaging system or at least one parameter, or estimation of at least one parameter, of said continuous-wave terahertz imaging system, such as the spectrum of the terahertz beam of said continuous-wave terahertz imaging system, is used is used as an input parameter for said mathematical equation for developing said point spread function.

23. The method of claim 20, wherein said point spread function is tuned iteratively until said enhanced-resolution terahertz image is achieved.

* * * * *